(12) United States Patent
Tamura et al.

(10) Patent No.: US 8,952,215 B2
(45) Date of Patent: Feb. 10, 2015

(54) ANTIBODY-PRODUCING TRANSGENIC SILKWORMS AND METHODS FOR PRODUCING THE SAME

(75) Inventors: Toshiki Tamura, Tsukuba (JP); Isao Kobayashi, Tsukuba (JP); Toshio Kanda, Tsukuba (JP); Keiro Uchino, Tsukuba (JP); Katsuhiro Katayama, Koriyama (JP); Tatsuya Ohashi, Koriyama (JP); Iwao Kiyokawa, Koriyama (JP); Hisae Arai, Kashiwa (JP); Noriyuki Funahashi, Kashiwa (JP)

(73) Assignees: Nitto Boseki Co., Ltd., Fukushima (JP); National Institute of Agrobiological Sciences, Ibaraki (JP)

( * ) Notice: Subject to any disclaimer, the term of this patent is extended or adjusted under 35 U.S.C. 154(b) by 1444 days.

(21) Appl. No.: 12/090,702

(22) PCT Filed: Oct. 18, 2006

(86) PCT No.: PCT/JP2006/320775
§ 371 (c)(1),
(2), (4) Date: Sep. 16, 2010

(87) PCT Pub. No.: WO2007/046439
PCT Pub. Date: Apr. 26, 2007

(65) Prior Publication Data
US 2011/0021757 A1    Jan. 27, 2011

(30) Foreign Application Priority Data
Oct. 18, 2005   (JP) .................................. 2005-302906

(51) Int. Cl.
| | | |
|---|---|---|
| C12N 15/00 | (2006.01) | |
| C07H 21/04 | (2006.01) | |
| C07K 16/00 | (2006.01) | |
| A01K 67/033 | (2006.01) | |
| A01K 67/04 | (2006.01) | |
| C07K 14/435 | (2006.01) | |
| C12N 15/85 | (2006.01) | |

(52) U.S. Cl.
CPC ........... C07K 16/00 (2013.01); C12N 2830/003 (2013.01); A01K 67/0335 (2013.01); A01K 67/04 (2013.01); A01K 2217/05 (2013.01); A01K 2227/703 (2013.01); A01K 2267/01 (2013.01); C07K 14/43586 (2013.01); C07K 2317/10 (2013.01); C07K 2317/20 (2013.01); C07K 2319/02 (2013.01); C12N 15/8509 (2013.01); C12N 2830/002 (2013.01)
USPC ............ 800/22; 800/21; 536/23.53; 536/24.1

(58) Field of Classification Search
CPC ...................... C12N 15/8509; C12N 2830/002; C12N 2830/003; A01K 67/00; A01K 67/0335; A01K 67/04

USPC .......................... 800/22, 21; 536/23.53, 24.1
See application file for complete search history.

(56) References Cited

U.S. PATENT DOCUMENTS

| | | |
|---|---|---|
| 2002/0182208 A1 | 12/2002 | Page et al. |
| 2005/0177877 A1* | 8/2005 | Hiramatsu et al. |
| 2006/0070132 A1 | 3/2006 | Tamura et al. |
| 2006/0143725 A1* | 6/2006 | Iijima et al. |
| 2009/0104660 A1 | 4/2009 | Jung et al. |
| 2010/0216239 A1 | 8/2010 | Xiong et al. |

FOREIGN PATENT DOCUMENTS

| | | |
|---|---|---|
| CN | 1399685 | 2/2003 |
| CN | 1516734 | 7/2004 |
| EP | 1176195 | 1/2002 |
| EP | 1391509 A1 | 2/2004 |
| EP | 1947180 | 7/2008 |
| JP | 2002315580 A | 10/2002 |
| JP | 2003512051 T | 4/2003 |
| JP | 2004081199 A | 3/2004 |
| JP | 2004135528 A | 5/2004 |
| JP | 2005/095063 | 4/2005 |
| JP | 2005095063 A | 4/2005 |
| JP | 2006/137739 | 6/2006 |
| JP | 2006137739 A | 6/2006 |
| KR | 20050036517 A | 4/2005 |
| WO | 0129204 A2 | 4/2001 |
| WO | 2005/038031 A1 | 4/2005 |
| WO | 2006/041225 A1 | 4/2006 |
| WO | 2008/117646 | 10/2008 |
| WO | 2009/150858 | 12/2009 |

OTHER PUBLICATIONS

Houdebine, L-M., 2002, Journal of Biotechnology, vol. 98, p. 145-160.*
Mercier et al., 1997, "The modification of milk protein composition through transgenesis: progress and problems," In: Transgenic Animals: Generation and use, Ed. Houdebine LM, Harwood Academic Publishers, The Netherlands pp. 473-482.*
Goldman et al., 2004, Med Sci Monit, vol. 10, No. 11, RA274-285.*
Sigmund, C., Jun. 2000, Arterioscler. Thromb. Vasc. Biol., p. 1425-1429.*
Skolnick et al., 2000, Trends in Biotech, vol. 18, p. 34-39.*
Tomasinsig et al., 2005, Current Protein and Peptide Science, vol. 6, p. 23-34.*
Smallwood et al., 2002,, Virology, vol. 304, p. 135-145.*
Chattopadhyay et al., 2004, Virus Research, vol. 99, p. 139-145.*
Hara et al., 1996, JP 08080163, Abstract.*
Tsubota et al., 2013, Insect Molecular Biology, published on line on Nov. 15, 2013.*

(Continued)

Primary Examiner — Shin Lin Chen
(74) Attorney, Agent, or Firm — Nixon Peabody LLP

(57) ABSTRACT

The present inventors produced transgenic silkworms which comprise a promoter of a DNA encoding a protein specifically expressed in the silk gland and a DNA encoding a recombinant antibody whose expression is regulated directly or indirectly by the promoter, and which secrete the recombinant antibody into the silk gland. The recombinant antibodies produced from the silk gland of the transgenic silkworms were confirmed to be active.

3 Claims, 14 Drawing Sheets

(56) References Cited

OTHER PUBLICATIONS

Horard et al., 1997, Molecular and Cellular Biology, vol. 17, No. 3, p. 1572-1579.*

Takiya et al., 2011, Insect Biochemistry and Molecular Biology, vol. 41, p. 592-601.*

Kiyokawa et al., U.S. Appl. No. 12/521,701, filed Feb. 16, 2010, entitled "Method for production of TRACP5b."

Imamura et al., "Targeted Gene Expression Using the GAL4/UAS System in the Silkworm *Bombyx mori*," Genetics 165:1329-40 (2003).

International Search Report for International Patent Application No. PCT/JP2006/320775 (Dec. 26, 2006).

Kiyokawa et al., "Production of Hexokinase and Anti-Human Transferrin Antibody for Clinical Diagnostic Reagent Using Transgenic Silkworm," 7th International Workshop on the Molecular Biology and Genetics of the Lepidoptera p. 94 (Aug. 20-26, 2006).

Suzuki, "The Forefront of Antibody Engineering," CMC Publishing, Tokyo pp. 78-88 (2004).

Tamura, "Methods for Producing Transformed Silkworms Using a Transposon," Abstracts of the 7th Workshop on Insect Function pp. 10-22 (1999).

Tamura, "Establishment of Methods for Producing Transgenic Silkworms—Expected to be Applied to Production of Fibers with Novel Functions," Chemistry and Biology 42(10):634-6 (2004).

Tamura, "Introduction of Useful Genes in Silkworm Development," Reports of the 21st Symposium on Basic Breeding: Advancement of Developmental Engineering in Molecular Breeding of Animals and Plants pp. 23-29 (2000).

Tamura et al., "Production of a Middle Silk Gland-Specific Gene Expression System that Uses the Yeast GAL4/UAS System," Abstracts of the Meeting of the Japanese Society of Sericultural Science p. 51 (2004).

Tamura, "Production of Transgenic Silkworms and Useful Substances," The Society of Polymer Science, Japan pp. 45-68 (2004).

Tamura, "Production of Useful Substance Using Transgenic Silkworm and Prospect of Future Utilization," Bio Industry 21(3):28-35 (2004).

Tamura, "Transgenic Silkworms: Current Status and Prospects," The Journal of Sericultural Science of Japan 69 (1):1-12 (2000).

Tamura et al., "Transgenic Silkworm Research in Japan: Recent Progress and Future," Prospects for the Development of Insect Factories, Proceedings of a Joint International Symposium of Insect COE Research Program and Insect Factory Research Project pp. 77-82 (Oct. 22-23, 2001).

Tomita et al., "Transgenic Silkworms Produce Recombinant Human Type III Procollagen in Cacoons," Nature Biotechnology 21:52-6 (2003).

Tamura et al., "Germline Transformation of the Silkworm *Bombyx mori* L. Using a piggyBac Transposon-Derived Vector," Nature Biotechnology 18:81-84 (2000).

Written Opinion of the International Searching Authority for International Patent Application PCT/JP2006/320775.

Douris et al., "Expression of Polydna Virus Genes in Lepidopteran Insect Cell Lines," J. Insect Science (Abstracts from the Sixth International Workshop on the Molecular Biology and Genetics of Lepidoptera) 3.36:3 (2003).

Motohashi et al., "Efficient Large-scale Protein Production of Larvae and Pupae of Silkworm by *Bombyx mori* Nuclear Polyhedrosis Virus Bacmid System," Biochem. Biophys. Res. Commun. 326:564-569 (2005).

Supplementary European Search Report for European Patent Application No. EP 06 81 1968 (Mar. 16, 2009).

Reis et al., Overseas Agronomy Serloulture, 59:44-45 (1994). "Production of antibody in the cells and body of *Bombyx mori* by using double recombinant *Bombyx mori* nuclear polyhadrosis virus."

Press release by Immuno-Biological Laboratories (http://www.ibl-japan.co.jp/news_img/prerelease_20101104.pdf).

Printed piece of the web-page of Proteomics Systems (http://proteo.jp/workflow04.html).

Office Action issued for JP2005-095063.

Reis et al., "Antibody Production in Silkworm Cells and Silkworm Larvae Infected with a Dual Recombinant *Bombyx mori* Nuclear Polyhedrosis Virus," Bio/Technol. 10:910-912 (1992).

Eizirik et al., Journal of Heredity, 92(2):212-9 (2001). "Molecular dating and biogeography of the early placental mammal radiation."

Grimaldi et al., Evolution of the Insects, Cambridge University Press, 558; May 2005.

Jarvis et al., Biotechnology, 8(10):950-5 (1990). "Use of early baculovirus promoters for continuous expression and efficient processing of foreign gene products in stably transformed lepidopteran cells."

Guttieri et al., Hybrid Hybridomics, 22(3):135-45 (2003). "Cassette vectors for conversion of Fab fragments into full-length human IgG1 monoclonal antibodies by expression in stably transformed insect cells."

Baim et al., PNAS USA, 88(12):5072-6 (1991). "A chimeric mammalian transactivator based on the lac repressor that is regulated by temperature and isopropyl beta-delta-thiogalactopyranoside."

Bello et al., Development 125:2193-2202 (1998). "Spatial and temporal targeting of gene expression in *Drosophila* by means of a tetracycline-dependent transactivator system."

Lycett et al., Genetics, 167:1780-1790 (2004). "Conditional expression in the malaria mosquito *Anopheles stephensi* with tet-on and tet-off systems."

McGuire et al., Trends in Genetics, 20(8):384-91 (2004). "Gene expression systems in *Drosophila*: a synthesis of time and space."

No et al., PNAS USA, 93:3346-3351 (1996). "Ecdysone-inducible gene expression in mammalian cells and transgenic mice."

Pollock and Clackson, Curr Opin Biotechnol, 13(5):459-67 (2002). "Dimerizer-regulated gene expression."

Zhu et al., Cell & Developmental Biology, 13:121-128 (2002). "Tetracycline-controlled transcriptional regulation systems: advances and application in transgenic animal modeling."

Kretzschmar et al. Journal of Immunological Methods, 195:93-101 (1996). "High-level expression in insect cells and purification of secreted monomeric single-chain Fv antibodies."

* cited by examiner

1. MARKER
2. pUASFvaTf                                              Pos. Cont.
3. GAL4/UAS STRAIN    DAY 5 OF THE 5TH INSTAR
4. GAL4/UAS STRAIN    DAY 1 OF SPINNING
5. GAL4/UAS STRAIN    DAY 2 OF SPINNING
6. Ser1GAL4 STRAIN    DAY 5 OF THE 5TH INSTAR    Neg. Cont.

FIG. 12
IgL
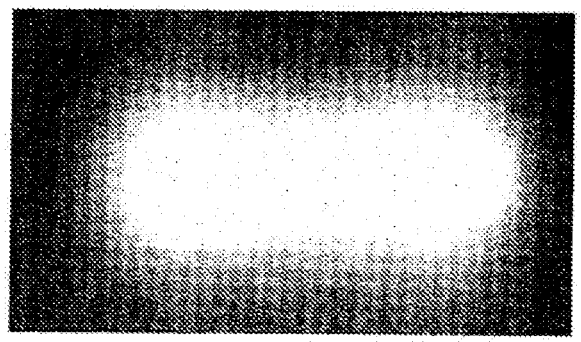
IgH
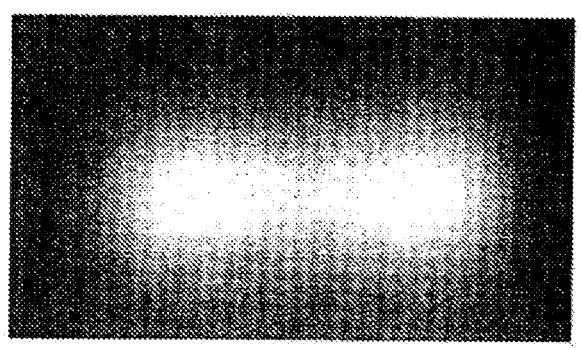
GAL4
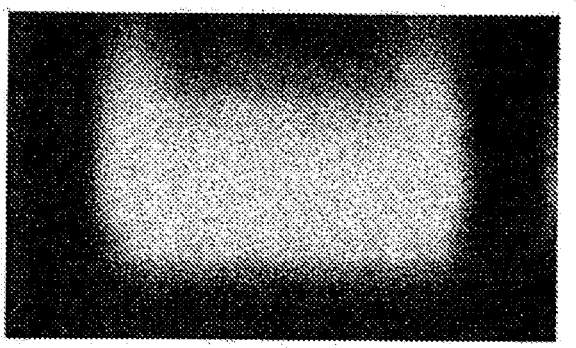
ACTIN
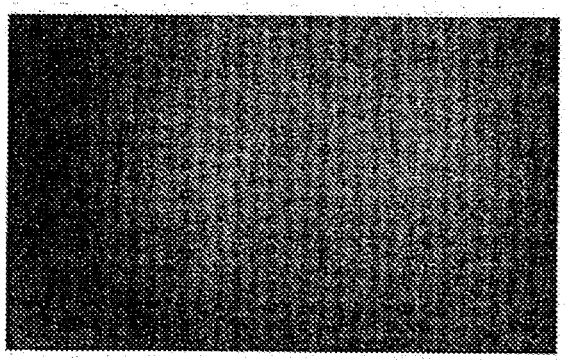

ANTIBODY-PRODUCING TRANSGENIC SILKWORMS AND METHODS FOR PRODUCING THE SAME

TECHNICAL FIELD

The present invention relates to methods for producing recombinant antibodies using silkworms, which allow large-scale production of antibodies similar to those produced by mammals. The present invention also relates to transgenic silkworms that produce the recombinant antibodies.

BACKGROUND ART

Recently, in the field of pharmaceuticals and diagnostic agents, large amounts of highly specific antibodies are needed for treatment and diagnosis of diseases. Antibodies are usually produced using mammals such as mice, rats, and rabbits, but they have recently been produced using cells of microorganisms or mammals, transgenic animals, transgenic plants and such. Characteristics of recombinant antibodies are that they can be produced at the same quality in large amounts and they are safe since viral diseases and the like are not incorporated and such; therefore, they are expected to become more important in the future.

On the other hand, recombinant antibodies also have many problems. For example, in microorganisms such as *E. coli*, only part of an antibody is produced and since glycosylation and phosphorylation of produced antibodies are insufficient, they are not sufficiently suitable for use as pharmaceuticals or diagnostic agents. Furthermore, human antibodies are generally known to be insoluble when produced by *E. coli* and such. Accordingly, purification of such antibodies requires the steps of solubilizing proteins with denaturants such as SDS and recovering activities of the proteins by gradually removing the denaturants in solution by dialysis or such.

Furthermore, when mammalian cells are used, production cost increases and thus large-scale production is difficult. Therefore, antibody production using transgenic animals and plants has been attempted, but it is still being studied. When other eukaryotic cells are used, a special signal is necessary to secrete an antibody out of the cells.

Silkworms have an organ called the silk gland, and a single silkworm has the ability to produce a maximum of 0.5 g of protein. In recent years, production techniques of transgenic silkworms have been developed, and methods for introducing foreign genes and for regulating expression of transgenes have advanced. Thus, it has now become possible to express transgenes in the silk gland and produce recombinant proteins. Since silkworms are eukaryotes, they can produce proteins similar to mammalian proteins compared to plants or microorganisms such as *E. coli*. In addition, silkworms can be reared on an artificial diet under clean conditions, and large-scale rearing at the level of several tens of thousands of silkworms can be easily carried out.

[Patent Document 1] Japanese Patent Application Kokai Publication No. (JP-A) 2006-137739: Tamura T. et al. "Method of protein production using a silkworm middle silk gland-specific gene expression system", filed by National Institute of Agrobiological Sciences on Mar. 15, 2005

[Non-patent Document 1] Tamura T., Sezutsu H., Kobayashi I., Kojima K., Kanda T., and Uchino K. (1999) "Methods for producing transformed silkworms using a transposon" Abstracts of the 7th Workshop on Insect Function, p. 10-22

[Non-patent Document 2] Tamura, T., Thibert, C., Royer, C., Kanda, T., Abraham, E., Kamba, M., Komoto, N., Thomas, J.-L., Mauchamp, B., Chavancy, G., Shirk, P., Fraser, M., Prudhomme, J.-C., and Couble, P. (2000) "A piggyBac element-derived vector efficiently promotes germ-line transformation in the silkworm *Bombyx mori* L." Nature Biotechnology 18, 81-84

[Non-patent Document 3] Tomita M, M. H., Sato T, Adachi T, Hino R, Hayashi M, Shimizu K, Nakamura N, Tamura T, Yoshizato K. (2003) "Transgenic silkworms produce recombinant human type III procollagen in cocoons." Nat Biotechnol 21, 52-56

[Non-patent Document 4] Tamura T. (2000) "Transgenic silkworms: Current status and prospects" J. Sericul. Sci. Japan, 69, 1-12

[Non-patent Document 5] Tamura T. (2000) "Introduction of useful genes in silkworm development" Reports of the 21st Symposium on Basic Breeding: Advancement of developmental engineering in molecular breeding of animals and plants, p. 23-29

[Non-patent Document 6] Tamura, T., Quan, G. X., Kanda, T., and Kuwabara, N. (2001) "Transgenic silkworm research in Japan: Recent progress and future" Proceeding of Joint International Symposium of Insect COE Research Program and Insect Factory Research Project. p. 77-82

[Non-patent Document 7] Imamma, M., Nakai, J., Inoue, S., Quan, G-X., Kanda T., and Tamura, T. (2003) "Targeted gene expression using the Gal4/UAS system in the silkworm *Bombyx mori*." Genetics, 165, 1329-1340

[Non-patent Document 8] Tamura, T. (2004) "Development and prospect of a production system for useful substances using transgenic silkworms" Bio Industry 20(3), 28-35

[Non-patent Document 9] Tamura, T., Uchino, K., Kanda, T., Kobayashi, I., and Kojima, K. (2004) "Production of a middle silk gland-specific gene expression system that uses the yeast GAL4/UAS system" Abstracts of the Meeting of the Japanese Society of Sericultural Science 74, p. 51

[Non-patent Document 10] Tamura T. (2004) "Establishment of methods for producing transgenic silkworms—expected to be applied to production of fibers with novel functions" Kagaku to Seibutsu (Chemistry and Biology) 42, 634-635

[Non-patent Document 11] Tamura, T. (2004) "Production of transgenic silkworms and useful substances" Biologics: Development of products using biological substances (The Society of Polymer Science, ed.) pp. 45-68.

[Non-patent Document 12] Ueda, K. (2004) "The forefront of antibody engineering" p. 122. CMC Publishing, Tokyo.

[Non-patent Document 13] Kiyokawa, I., Kobayashi, I., Uchino, K., Sezutsu, H., Kanda, T., Tamura, T., Miura, T., Ohashi, T., and Katayama K. (2006) "Production of hexokinase and anti-human transferrin antibody for clinical diagnostic reagent using transgenic silkworm" Abstracts of the 7th International Workshop on the Molecular Biology and Genetics of the Lepidoptera, p 94

DISCLOSURE OF THE INVENTION

Problems to be Solved by the Invention

As described above, although the importance of recombinant antibodies is increasing, there are many problems with their production. The present invention was achieved in view of these circumstances. An objective of the present invention is to provide methods for producing large amounts of recombinant antibodies that are similar to antibodies produced by mammals by using transgenic silkworms.

Means for Solving the Problems

The present inventors conducted dedicated research to solve the above-mentioned problems. Specifically, the upstream region of a gene specifically expressed in the silk gland was used as a promoter region and inserted upstream of the GAL4 gene. Then, this fused gene was inserted into a plasmid vector for producing transgenic silkworms. Transgenic silkworms were produced by the method of Tamura et al. (2000). The obtained transgenic silkworms were crossed with a UASFvaTf strain produced by the method of Imamura et al. (2003). The UASFvaTf strain carries an scFv antibody gene that reacts with transferrin downstream of the GAL4 target sequence UAS. Western blotting was performed on samples extracted from silk glands of the transgenic silkworms obtained by crossing at the spinning stage, and as a result, it was confirmed that antibodies were produced in the silk glands. Furthermore, when extraction samples obtained in the same manner were reacted with an antigen, the amount of substance reacting with the antigen increased as the amount of silk gland extract increased. This showed that the samples had antibody activity.

More specifically, the present invention relates to methods for producing recombinant proteins in the silkworm silk gland, and provides [1] to [49] described below:

[1] a method for producing a recombinant antibody, wherein the method comprises the steps of:
(a) producing a transgenic silkworm into which a DNA encoding a signal sequence-comprising recombinant antibody is introduced, and
(b) recovering the recombinant antibody from the produced transgenic silkworm;

[2] a method for producing a recombinant antibody, wherein the method comprises the steps of:
(a) producing a transgenic silkworm which comprises a promoter of a DNA encoding a protein specifically expressed in the silk gland and a DNA encoding a signal sequence-comprising recombinant antibody whose expression is regulated directly or indirectly by the promoter, and which secretes the recombinant antibody into the silk gland; and
(b) recovering the recombinant antibody from the produced transgenic silkworm;

[3] the method of [2], wherein the transgenic silkworm comprises the DNAs of (i) and (ii) below:
(i) a transcriptional regulator-encoding DNA operably linked downstream of a promoter of a DNA encoding a protein specifically expressed in the silk gland; and
(ii) a DNA encoding a signal sequence-comprising recombinant antibody, which is operably linked downstream of a target promoter of the transcriptional regulator;

[4] the method of [2], wherein the transgenic silkworm is produced by crossing the transgenic silkworms of (i) and (ii) below:
(i) a transgenic silkworm comprising a transcriptional regulator-encoding DNA operably linked downstream of a promoter of a DNA encoding a protein specifically expressed in the silk gland; and
(ii) a transgenic silkworm comprising a DNA encoding a signal sequence-comprising recombinant antibody, which is operably linked downstream of a target promoter of the transcriptional regulator;

[5] the method of [3] or [4], wherein the transcriptional regulator is GAL[4 and the target promoter is UAS;

[6] the method of any one of [2] to [5], wherein the silk gland is a middle silk gland or posterior silk gland;

[7] the method of [6], wherein the promoter of a DNA encoding a protein specifically expressed in the silk gland is a promoter of a DNA encoding the sericin 1 protein or the sericin 2 protein;

[7-1] the method of [7], wherein the promoter of a DNA encoding the sericin 1 protein is (a) or (b) below:
(a) a DNA comprising the nucleotide sequence of SEQ ID NO: 16, or
(b) a DNA comprising a nucleotide sequence with one or more nucleotide substitutions, deletions, additions, and/or insertions in the nucleotide sequence of SEQ ID NO: 16;

[7-2] the method of [7], wherein the promoter of a DNA encoding the sericin 2 protein is (a) or (b) below:
(a) a DNA comprising the nucleotide sequence of SEQ ID NO: 17, or
(b) a DNA comprising a nucleotide sequence with one or more nucleotide substitutions, deletions, additions, and/or insertions in the nucleotide sequence of SEQ ID NO: 17;

[8] the method of [6], wherein the promoter of a DNA encoding a protein specifically expressed in the silk gland is a promoter of a DNA encoding the fibroin protein;

[8-1] the method of [8], wherein the promoter of a DNA encoding the fibroin protein is (a) or (b) below:
(a) a DNA comprising the nucleotide sequence of SEQ ID NO: 18, or
(b) a DNA comprising a nucleotide sequence with one or more nucleotide substitutions, deletions, additions, and/or insertions in the nucleotide sequence of SEQ ID NO: 18;

[9] a recombinant antibody comprising a signal sequence;
[9-1] the antibody of [9], wherein the signal sequence is derived from an animal;
[9-2] the antibody of [9], wherein the signal sequence is derived from an animal antibody;
[9-3] the antibody of [9], wherein the signal sequence is a human acid phosphatase signal sequence, a mouse immunoglobulin κ L chain signal sequence, or a mouse IgG1 signal sequence;

[10] the antibody of [9], which is a full-length antibody or a low-molecular-weight antibody (minibody);
[10-1] the antibody of [10], wherein the low-molecular-weight antibody is an scFv antibody;
[10-2] the scFv antibody of [10-1] comprising a signal sequence, VH, linker, and VL; or a signal sequence, VL, linker, and VH arranged in this order from the N terminal side of the single chain polypeptide;
[10-3] the scFv antibody of [10], wherein the antigen is transferrin, CRP, IgG, IgA, IgM, IgD, IgE, albumin, prealbumin, complement C3, complement C4, α-1 microglobulin, β-2 microglobulin, AFP, CA 19-9, CA15-3, PSA, apolipoprotein, tumor necrosis factor, interleukin, interferon, osteopontin, HBs antigen, RF, HCG, collagen, Hb, HbAlc, HCV antibody, troponin, myoglobin, FDP, CEA, c-erbB-2, or haptoglobin;
[10-4] the scFv antibody of [10-3], wherein the VH, linker, and VL comprise the amino acid sequences of SEQ ID NOs: 6, 9, and 12, respectively;
[10-5] the scFv antibody of [10-3], wherein the signal sequence comprises the amino acid sequence of any one of SEQ ID NOs: 3, 21, and 29;
[10-6] an scFv antibody comprising the amino acid sequence of SEQ ID NO: 15;
[10-7] an antibody that comprises an L chain comprising the amino acid sequence of any one of SEQ ID NOs: 3, 21, and 29 as a signal sequence, and an H chain comprising the amino acid sequence of any one of SEQ ID NOs: 3, 21, and 29 as a signal sequence;
[10-8] an antibody that comprises an L chain comprising the amino acid sequence of any one of SEQ ID NOs: 3, 21, and 29 as a signal sequence, the amino acid sequence of SEQ ID NO: 23 as an L chain variable region, the amino acid sequence of SEQ ID NO: 25 as a Jκ segment, and the amino acid sequence of SEQ ID NO: 27 as a κ chain constant region; and an H chain comprising the amino acid sequence of any one of SEQ ID NOs: 3, 21, and 29 as a signal sequence, the amino acid sequence of SEQ ID NO: 31 as an H chain variable region, the amino acid sequence of SEQ ID NO: 33 as CH1, the amino acid sequence of SEQ ID NO: 35 as a hinge region, the amino acid sequence of SEQ ID NO: 37 as CH2, and the amino acid sequence of SEQ ID NO: 39 as CH3;

[10-9] an antibody that comprises an L chain comprising the amino acid sequence of SEQ ID NO: 49 and an H chain comprising the amino acid sequence of SEQ ID NO: 51;

[11] a DNA encoding the antibody of any one of [9] to [10-9];

[11-1] a DNA encoding an scFv antibody that comprises the nucleotide sequence of any one of SEQ ID NOs: 2, 20, and 28 as a signal sequence, the nucleotide of SEQ ID NO: 5 as VH, the nucleotide sequence of SEQ ID NO: 8 as a linker, and the nucleotide sequence of SEQ ID NO: 11 as VL;

[11-2] a DNA encoding an scFv antibody which comprises the nucleotide sequence of any one of SEQ ID NOs: 1, 20, and 28 as a signal sequence, the nucleotide of SEQ ID NO: 4 as VH, the nucleotide sequence of SEQ ID NO: 7 as a linker, and the nucleotide sequence of SEQ ID NO: 10 as VL;

[11-3] a DNA encoding an scFv antibody that comprises the nucleotide sequence of SEQ ID NO: 14;

[11-4] a DNA encoding a scFv antibody that comprises the nucleotide sequence of SEQ ID NO: 13;

[11-5] a DNA that comprises a DNA encoding an antibody L chain that comprises the nucleotide sequence of any one of SEQ ID NOs: 1, 2, 20, and 28 as a signal sequence, and a DNA encoding an antibody H chain that comprises the nucleotide sequence of any one of SEQ ID NOs: 1, 2, 20, and 28 as a signal sequence;

[11-6] a DNA that comprises a DNA encoding an antibody L chain that comprises the nucleotide sequence of any one of SEQ ID NOs: 1, 2, 20, and 28 as a signal sequence, the nucleotide sequence of SEQ ID NO: 22 as an L chain variable region, the nucleotide sequence of SEQ ID NO: 24 as a Jκ segment, and the nucleotide sequence of SEQ ID NO: 26 as a κ chain constant region; and a DNA encoding an antibody H chain that comprises the nucleotide sequence of any one of SEQ ID NOs: 1, 2, 20, and 28 as a signal sequence, the nucleotide sequence of SEQ ID NO: 30 as an H chain variable region, the nucleotide sequence of SEQ ID NO: 32 as CH1, the nucleotide sequence of SEQ ID NO: 34 as a hinge region, the nucleotide sequence of SEQ ID NO: 36 as CH2, and the nucleotide sequence of SEQ ID NO: 38 as CH3;

[11-7] a DNA that comprises a DNA comprising the nucleotide sequence of SEQ ID NO: 48 as an antibody L chain, and a DNA comprising the nucleotide sequence of SEQ ID NO: 50 as an antibody H chain;

[12] a vector comprising the DNA of any one of [11] to [11-7];

[13] a cell carrying the vector of [12];

[14] a method for producing a transgenic silkworm that secretes a recombinant antibody comprising a signal sequence, wherein the method comprises the step of producing a silkworm egg comprising a DNA encoding the recombinant antibody;

[15] a method for producing a transgenic silkworm that secretes a recombinant antibody into the silk gland, comprising the step of producing a silkworm egg which comprises a promoter of a DNA encoding a protein specifically expressed in the silk gland, and a DNA encoding a signal sequence-comprising recombinant antibody whose expression is regulated directly or indirectly by the promoter;

[16] the method of [15], wherein the transgenic silkworm comprises the DNAs of (i) and (ii) below:

(i) a transcriptional regulator-encoding DNA operably linked downstream of a promoter of a DNA encoding a protein specifically expressed in the silk gland, and (ii) a DNA encoding a signal sequence-comprising recombinant antibody, which is operably linked downstream of a target promoter of the transcriptional regulator;

[17] the method of [15], wherein the transgenic silkworm is produced by crossing the transgenic silkworms of (i) and (ii) below:

(i) a transgenic silkworm comprising a transcriptional regulator-encoding DNA operably linked downstream of a promoter of a DNA encoding a protein that is specifically expressed in the silk gland, and (ii) a transgenic silkworm comprising a DNA encoding a signal sequence-comprising recombinant antibody, which is operably linked downstream of a target promoter of the transcriptional regulator;

[18] the method of [16] or [17], wherein the transcriptional regulator is GAL4 and the target promoter is UAS;

[19] the method of any one of [15] to [18], wherein the silk gland is a middle silk gland or posterior silk gland;

[20] the method of [19], wherein the promoter of a DNA encoding a protein that is specifically expressed in the silk gland is a promoter of a DNA encoding the sericin 1 protein or the sericin 2 protein;

[20-1] the method of [20], wherein the promoter of a DNA encoding the sericin 1 protein is (a) or (b) below:

(a) a DNA comprising the nucleotide sequence of SEQ ID NO: 16, or (b) a DNA comprising a nucleotide sequence with one or more nucleotide substitutions, deletions, additions, and/or insertions in the nucleotide sequence of SEQ ID NO: 16;

[20-2] the method of [20], wherein the promoter of a DNA encoding the sericin 2 protein is (a) or (b) below:

(a) a DNA comprising the nucleotide sequence of SEQ ID NO: 17, or (b) a DNA comprising a nucleotide sequence with one or more nucleotide substitutions, deletions, additions, and/or insertions in the nucleotide sequence of SEQ ID NO: 17;

[21] the method of [19], wherein the promoter of a DNA encoding a protein that is specifically expressed in the silk gland is a promoter of a DNA encoding the fibroin protein;

[21-1] the method of [21], wherein the promoter of a DNA encoding the fibroin protein is (a) or (b) below:

(a) a DNA comprising the nucleotide sequence of SEQ ID NO: 18, or (b) a DNA comprising a nucleotide sequence with one or more nucleotide substitutions, deletions, additions, and/or insertions in the nucleotide sequence of SEQ ID NO: 18;

[22] a transgenic silkworm that comprises a DNA encoding a signal sequence-comprising recombinant antibody and secretes the recombinant antibody;

[23] a transgenic silkworm which comprises a promoter of a DNA encoding a protein that is specifically expressed in the silk gland and a DNA encoding a signal sequence-comprising recombinant antibody whose expression is regulated directly or indirectly by the promoter, and which secretes the recombinant antibody into the silk gland;

[24] the transgenic silkworm of [23], which comprises the DNAs of (i) and (ii) below:

(i) a transcriptional regulator-encoding DNA operably linked downstream of a promoter of a DNA encoding a protein specifically expressed in the silk gland, and (ii) a DNA encoding a signal sequence-comprising recombinant antibody, which is operably linked downstream of a target promoter of the transcriptional regulator;

[25] the transgenic silkworm of [23], which is produced by crossing the transgenic silkworms of (i) and (ii) below:

(i) a transgenic silkworm comprising a transcriptional regulator-encoding DNA operably linked downstream of a promoter of a DNA encoding a protein specifically expressed in the silk gland, and (ii) a transgenic silkworm comprising a DNA encoding a signal sequence-comprising recombinant antibody, which is operably linked downstream of a target promoter of the transcriptional regulator;

[26] the transgenic silkworm of [24] or [25], wherein the transcriptional regulator is GAL4 and the target promoter is UAS;

[27] the transgenic silkworm of any one of [23] to [26], wherein the silk gland is a middle silk gland or posterior silk gland;

[28] the transgenic silkworm of [27], wherein the promoter of a DNA encoding a protein specifically expressed in the silk gland is a promoter of a DNA encoding the sericin 1 protein or the sericin 2 protein;

[28-1] the transgenic silkworm of [28], wherein the promoter of a DNA encoding the sericin 1 protein is (a) or (b) below:

(a) a DNA comprising the nucleotide sequence of SEQ ID NO: 16, or (b) a DNA comprising a nucleotide sequence with one or more nucleotide substitutions, deletions, additions, and/or insertions in the nucleotide sequence of SEQ ID NO: 16;

[28-2] the transgenic silkworm of [28], wherein the promoter of a DNA encoding the sericin 2 protein is (a) or (b) below:

(a) a DNA comprising the nucleotide sequence of SEQ ID NO: 17, or (b) a DNA comprising a nucleotide sequence with one or more nucleotide substitutions, deletions, additions, and/or insertions in the nucleotide sequence of SEQ ID NO: 17;

[29] the transgenic silkworm of [27], wherein the promoter of a DNA encoding a protein specifically expressed in the silk gland is a promoter of a DNA encoding the fibroin protein;

[29-1] the transgenic silkworm of [29], wherein the promoter of a DNA encoding the fibroin protein is (a) or (b) below:

(a) a DNA comprising the nucleotide sequence of SEQ ID NO: 18, or (b) a DNA comprising a nucleotide sequence with one or more nucleotide substitutions, deletions, additions, and/or insertions in the nucleotide sequence of SEQ ID NO: 18;

[30] a transgenic silkworm which comprises a DNA encoding a signal sequence-comprising recombinant antibody, which is operably linked downstream of a target promoter of a transcriptional regulator;

[31] the transgenic silkworm of [30], wherein the transcriptional regulator is GAL4 and the target promoter is UAS;

[32] a method for producing a recombinant antibody, wherein the method comprises the steps of:

(a) producing a transgenic silkworm which comprises a promoter of a DNA encoding a cytoplasmic actin protein and a DNA encoding a signal sequence-comprising recombinant antibody whose expression is regulated directly or indirectly by the promoter, and which secretes the recombinant antibody into the fat body, and (b) recovering the recombinant antibody from the produced transgenic silkworm;

[33] the method of [32], wherein the transgenic silkworm comprises the DNAs of (i) and (ii) below:

(i) a transcriptional regulator-encoding DNA operably linked downstream of a promoter of a DNA encoding a cytoplasmic actin protein, and (ii) a DNA encoding a signal sequence-comprising recombinant antibody, which is operably linked downstream of a target promoter of the transcriptional regulator;

[34] the method of [32], wherein the transgenic silkworm is produced by crossing the transgenic silkworms of (i) and (ii) below:

(i) a transgenic silkworm comprising a transcriptional regulator-encoding DNA operably linked downstream of a promoter of a DNA encoding a cytoplasmic actin protein, and (ii) a transgenic silkworm comprising a DNA encoding a signal sequence-comprising recombinant antibody, which is operably linked downstream of a target promoter of the transcriptional regulator;

[35] the method of [33] or [34], wherein the transcriptional regulator is GAL4 and the target promoter is UAS;

[35-1] the method of [35], wherein the promoter of a cytoplasmic actin protein-encoding DNA is (a) or (b) below:

(a) a DNA comprising the nucleotide sequence of SEQ ID NO: 19, or (b) a DNA comprising a nucleotide sequence with one or more nucleotide substitutions, deletions, additions, and/or insertions in the nucleotide sequence of SEQ ID NO: 19;

[36] a method for producing a transgenic silkworm that secretes a recombinant antibody into the fat body, comprising the step of producing a silkworm egg that comprises a promoter of a DNA encoding a cytoplasmic actin protein and a DNA encoding a signal sequence-comprising recombinant antibody whose expression is regulated directly or indirectly by the promoter;

[37] the method of [36], wherein the transgenic silkworm comprises the DNAs of (i) and (ii) below:

(i) a transcriptional regulator-encoding DNA operably linked downstream of a promoter of a DNA encoding a cytoplasmic actin protein, and (ii) a DNA encoding a signal sequence-comprising recombinant antibody, which is operably linked downstream of a target promoter of the transcriptional regulator;

[38] the method of [36], wherein the transgenic silkworm is produced by crossing the transgenic silkworms of (i) and (ii) below:

(i) a transgenic silkworm comprising a transcriptional regulator-encoding DNA operably linked downstream of a promoter of a DNA encoding a cytoplasmic actin protein, and (ii) a transgenic silkworm comprising a DNA encoding a signal sequence-comprising recombinant antibody, which is operably linked downstream of a target promoter of the transcriptional regulator;

[39] the method of [37] or [38], wherein the transcriptional regulator is GAL4 and the target promoter is UAS;

[39-1] the method of [39], wherein the promoter of a cytoplasmic actin protein-encoding DNA is (a) or (b) below:

(a) a DNA comprising the nucleotide sequence of SEQ ID NO: 19, or (b) a DNA comprising a nucleotide sequence with one or more nucleotide substitutions, deletions, additions, and/or insertions in the nucleotide sequence of SEQ ID NO: 19;

[40] a transgenic silkworm which comprises a promoter of a DNA encoding a cytoplasmic actin protein and a DNA encoding a signal sequence-comprising recombinant antibody whose expression is regulated directly or indirectly by the promoter, and which secretes the recombinant antibody into the fat body;

[41] the transgenic silkworm of [40], which comprises the DNAs of (i) and (ii) below:
(i) a transcriptional regulator-encoding DNA operably linked downstream of a promoter of a DNA encoding a cytoplasmic actin protein, and
(ii) a DNA encoding a signal sequence-comprising recombinant antibody, which is operably linked downstream of a target promoter of the transcriptional regulator;

[42] the transgenic silkworm of [40], which is produced by crossing the transgenic silkworms of (i) and (ii) below:
(i) a transgenic silkworm comprising a transcriptional regulator-encoding DNA operably linked downstream of a promoter of a DNA encoding a cytoplasmic actin protein, and
(ii) a transgenic silkworm comprising a DNA encoding a signal sequence-comprising recombinant antibody, which is operably linked downstream of a target promoter of the transcriptional regulator;

[43] the transgenic silkworm of [41] or [42], wherein the transcriptional regulator is GAL4 and the target promoter is UAS;

[43-1] the method of [43], wherein the promoter of a cytoplasmic actin protein-encoding DNA is (a) or (b) below:
(a) a DNA comprising the nucleotide sequence of SEQ ID NO: 19, or
(b) a DNA comprising a nucleotide sequence with one or more nucleotide substitutions, deletions, additions, and/or insertions in the nucleotide sequence of SEQ ID NO: 19;

[44] a method for measuring the amount of transferrin in a living body, which comprises the steps of:
(a) contacting a biological sample derived from a subject with the antibody of any one of [9] to [10-9] or with an antibody produced by the method of any one of [1] to [8-1], [32] to [35-1], [50] to [57-1], and [76] to [79-1], and
(b) detecting the binding between the antibody and transferrin in the biological sample;

[45] a method for diagnosing diabetic nephropathy comprising the steps of:
(a) contacting a biological sample obtained from a subject with the antibody of any one of [9] to [10-9] or with an antibody produced by the method of any one of [1] to [8-1], [32] to [35-1], [50] to [57-1], and [76] to [79-1], and
(b) detecting the antibody bound to transferrin in the biological sample, in which the subject is judged to be affected by or have a high risk of diabetic neuropathy when the amount of transferrin is greater than that in a normal control;

[46] a method for diagnosing diabetic nephropathy comprising the steps of:
(a) contacting a biological sample obtained from a subject with the antibody of any one of [9] to [10-9] or with an antibody produced by the method of any one of [1] to [8-1], [32] to [35-1], [50] to [57-1], and [76] to [79-1], and
(b) detecting the antibody bound to transferrin in the biological sample, in which the subject is judged to be affected by or have a high risk of diabetic neuropathy when the amount of transferrin is comparable to that in a control clearly affected by diabetic nephropathy;

[47] a method for evaluating nutritional status comprising the steps of:
(a) contacting a biological sample obtained from a subject with the antibody of any one of [9] to [10-9] or with an antibody produced by the method of any one of [1] to [8-1], [32] to [35-1], [50] to [57-1], and [76] to [79-1], and
(b) detecting the antibody bound to transferrin in the biological sample, in which the subject is judged to suffer from or have a high risk of malnutrition when the amount of transferrin is less than that in a normal control;

[48] a diagnostic agent for diabetic nephropathy, which comprises the antibody of any one of [9] to [10-9] or an antibody produced by the method of any one of [1] to [8-1], [32] to [35-1], [50] to [57-1], and [76] to [79-1] as an active ingredient;

[49] a reagent for evaluating nutritional status, which comprises the antibody of any one of [9] to [10-9] or an antibody produced by the method of any one of [1] to [8-1], [32] to [35-1], [50] to [57-1], and [76] to [79-1] as an active ingredient;

[50] a method for producing a recombinant antibody, wherein the method comprises the steps of:
(a) producing a transgenic silkworm into which a recombinant antibody-encoding DNA is introduced, and
(b) recovering the recombinant antibody from the produced transgenic silkworm;

[51] a method for producing a recombinant antibody, wherein the method comprises the steps of:
(a) producing a transgenic silkworm which comprises a promoter of a DNA encoding a protein specifically expressed in the silk gland and a DNA encoding a recombinant antibody whose expression is regulated directly or indirectly by the promoter, and which secretes the recombinant antibody into the silk gland, and
(b) recovering the recombinant antibody from the produced transgenic silkworm;

[52] the method of [51], wherein the transgenic silkworm comprises the DNAs of (i) and (ii) below:
(i) a DNA encoding a transcriptional regulator that is operably linked downstream of a promoter of a DNA encoding a protein specifically expressed in the silk gland, and
(ii) a DNA encoding a recombinant antibody that is operably linked downstream of a target promoter of the transcriptional regulator;

[53] the method of [51], wherein the transgenic silkworm is produced by crossing the transgenic silkworms of (i) and (ii) below:
(i) a transgenic silkworm comprising a DNA encoding a transcriptional regulator that is operably linked downstream of a promoter of a DNA encoding a protein specifically expressed in the silk gland, and
(ii) a transgenic silkworm comprising a DNA encoding a recombinant antibody that is operably linked downstream of a target promoter of the transcriptional regulator;

[54] the method of [52] or [53], wherein the transcriptional regulator is GAL4 and the target promoter is UAS;

[55] the method of any one of [51] to [54], wherein the silk gland is a middle silk gland or posterior silk gland;

[56] the method of [55], wherein the promoter of a DNA encoding a protein specifically expressed in the silk gland is a promoter of a DNA encoding the sericin 1 protein or the sericin 2 protein;

[56-1] the method of [56], wherein the promoter of a DNA encoding the sericin 1 protein is (a) or (b) below:
(a) a DNA comprising the nucleotide sequence of SEQ ID NO: 16, or
(b) a DNA comprising a nucleotide sequence with one or more nucleotide substitutions, deletions, additions, and/or insertions in the nucleotide sequence of SEQ ID NO: 16;

[56-2] the method of [56], wherein the promoter of a DNA encoding the sericin 2 protein is (a) or (b) below:
(a) a DNA comprising the nucleotide sequence of SEQ ID NO: 17, or
(b) a DNA comprising a nucleotide sequence with one or more nucleotide substitutions, deletions, additions, and/or insertions in the nucleotide sequence of SEQ ID NO: 17;

[57] the method of [55], wherein the promoter of a DNA encoding a protein specifically expressed in the silk gland is a promoter of a DNA encoding the fibroin protein;

[57-1] the method of [57], wherein the promoter of a DNA encoding the fibroin protein is (a) or (b) below:
(a) a DNA comprising the nucleotide sequence of SEQ ID NO: 18, or
(b) a DNA comprising a nucleotide sequence with one or more nucleotide substitutions, deletions, additions, and/or insertions in the nucleotide sequence of SEQ ID NO: 18;

[58] a method for producing a transgenic silkworm that secretes a recombinant antibody, wherein the method comprises the step of producing a silkworm egg comprising a DNA encoding the recombinant antibody;

[59] a method for producing a transgenic silkworm that secretes a recombinant antibody into the silk gland, comprising the step of producing a silkworm egg that comprises a promoter of a DNA encoding a protein specifically expressed in the silk gland, and a DNA encoding a recombinant antibody whose expression is regulated directly or indirectly by the promoter;

[60] the method of [59], wherein the transgenic silkworm comprises the DNAs of (i) and (ii) below:
(i) a DNA encoding a transcriptional regulator that is operably linked downstream of a promoter of a DNA encoding a protein specifically expressed in the silk gland, and
(ii) a DNA encoding a recombinant antibody that is operably linked downstream of a target promoter of the transcriptional regulator;

[61] the method of [59], wherein the transgenic silkworm is produced by crossing the transgenic silkworms of (i) and (ii) below:
(i) a transgenic silkworm comprising a DNA encoding a transcriptional regulator that is operably linked downstream of a promoter of a DNA encoding a protein specifically expressed in the silk gland, and
(ii) a transgenic silkworm comprising a DNA encoding a recombinant antibody that is operably linked downstream of a target promoter of the transcriptional regulator;

[62] the method of [60] or [61], wherein the transcriptional regulator is GAL4 and the target promoter is UAS;

[63] the method of any one of [59] to [62], wherein the silk gland is a middle silk gland or posterior silk gland;

[64] the method of [63], wherein the promoter of a DNA encoding a protein specifically expressed in the silk gland is a promoter of a DNA encoding the sericin 1 protein or the sericin 2 protein;

[64-1] the method of [64], wherein the promoter of a DNA encoding the sericin 1 protein is (a) or (b) below:
(a) a DNA comprising the nucleotide sequence of SEQ ID NO: 16, or
(b) a DNA comprising a nucleotide sequence with one or more nucleotide substitutions, deletions, additions, and/or insertions in the nucleotide sequence of SEQ ID NO: 16;

[64-2] the method of [64], wherein the promoter of a DNA encoding the sericin 2 protein is (a) or (b) below:
(a) a DNA comprising the nucleotide sequence of SEQ ID NO: 17, or
(b) a DNA comprising a nucleotide sequence with one or more nucleotide substitutions, deletions, additions, and/or insertions in the nucleotide sequence of SEQ ID NO: 17;

[65] the method of [63], wherein the promoter of a DNA encoding a protein specifically expressed in the silk gland is a promoter of a DNA encoding the fibroin protein;

[65-1] the method of [65], wherein the promoter of a DNA encoding the fibroin protein is (a) or (b) below:
(a) a DNA comprising the nucleotide sequence of SEQ ID NO: 18, or
(b) a DNA comprising a nucleotide sequence with one or more nucleotide substitutions, deletions, additions, and/or insertions in the nucleotide sequence of SEQ ID NO: 18;

[66] a transgenic silkworm that comprises a DNA encoding a recombinant antibody and secretes the recombinant antibody;

[67] a transgenic silkworm that comprises a promoter of a DNA encoding a protein specifically expressed in the silk gland and a DNA encoding a recombinant antibody whose expression is regulated directly or indirectly by the promoter, and which secretes the recombinant antibody into the silk gland;

[68] the transgenic silkworm of [67], which comprises the DNAs of (i) and (ii) below:
(i) a DNA encoding a transcriptional regulator operably linked downstream of a promoter of a DNA encoding a protein specifically expressed in the silk gland, and (ii) a DNA encoding a recombinant antibody operably linked downstream of a target promoter of the transcriptional regulator;

[69] the transgenic silkworm of [67], which is produced by crossing the transgenic silkworms of (i) and (ii) below:
(i) a transgenic silkworm comprising a DNA encoding a transcriptional regulator that is operably linked downstream of a promoter of a DNA encoding a protein specifically expressed in the silk gland, and
(ii) a transgenic silkworm comprising a DNA encoding a recombinant antibody that is operably linked downstream of a target promoter of the transcriptional regulator;

[70] the transgenic silkworm of [68] or [69], wherein the transcriptional regulator is GAL4 and the target promoter is UAS;

[71] the transgenic silkworm of any one of [67] to [70], wherein the silk gland is a middle silk gland or posterior silk gland;

[72] the transgenic silkworm of [71], wherein the promoter of a DNA encoding a protein specifically expressed in the silk gland is a promoter of a DNA encoding the sericin 1 protein or the sericin 2 protein;

[72-1] the transgenic silkworm of [72], wherein the promoter of a DNA encoding the sericin 1 protein is (a) or (b) below:
(a) a DNA comprising the nucleotide sequence of SEQ ID NO: 16, or
(b) a DNA comprising a nucleotide sequence with one or more nucleotide substitutions, deletions, additions, and/or insertions in the nucleotide sequence of SEQ ID NO: 16;

[72-2] the transgenic silkworm of [72], wherein the promoter of a DNA encoding the sericin 2 protein is (a) or (b) below:
(a) a DNA comprising the nucleotide sequence of SEQ ID NO: 17, or
(b) a DNA comprising a nucleotide sequence with one or more nucleotide substitutions, deletions, additions, and/or insertions in the nucleotide sequence of SEQ ID NO: 17;

[73] the transgenic silkworm of [71], wherein the promoter of a DNA encoding a protein specifically expressed in the silk gland is a promoter of a DNA encoding the fibroin protein;

[73-1] the transgenic silkworm of [73], wherein the promoter of a DNA encoding the fibroin protein is (a) or (b) below:

(a) a DNA comprising the nucleotide sequence of SEQ ID NO: 18, or (b) a DNA comprising a nucleotide sequence with one or more nucleotide substitutions, deletions, additions, and/or insertions in the nucleotide sequence of SEQ ID NO: 18;

[74] a transgenic silkworm comprising a DNA encoding a recombinant antibody that is operably linked downstream of a target promoter of a transcriptional regulator;

[75] the transgenic silkworm of [74], wherein the transcriptional regulator is GAL4 and the target promoter is UAS;

[76] a method for producing a recombinant antibody, wherein the method comprises the steps of:

(a) producing a transgenic silkworm which comprises a promoter of a DNA encoding a cytoplasmic actin protein and a DNA encoding a recombinant antibody whose expression is regulated directly or indirectly by the promoter, and which secretes the recombinant antibody into the fat body, and (b) recovering the recombinant antibody from the produced transgenic silkworm;

[77] the method of [76], wherein the transgenic silkworm comprises the DNAs of (i) and (ii) below:

(i) a DNA encoding a transcriptional regulator that is operably linked downstream of a promoter of a cytoplasmic actin protein-encoding DNA, and (ii) a DNA encoding a recombinant antibody operably linked downstream of a target promoter of the transcriptional regulator;

[78] the method of [76], wherein the transgenic silkworm is produced by crossing the transgenic silkworms of (i) and (ii) below:

(i) a transgenic silkworm comprising a DNA encoding a transcriptional regulator that is operably linked downstream of a promoter of a cytoplasmic actin protein-encoding DNA, and (ii) a transgenic silkworm comprising a DNA encoding a recombinant antibody that is operably linked downstream of a target promoter of the transcriptional regulator;

[79] the method of [77] or [78], wherein the transcriptional regulator is GAL4 and the target promoter is UAS;

[79-1] the method of [79], wherein the promoter of a cytoplasmic actin protein-encoding DNA is (a) or (b) below:

(a) a DNA comprising the nucleotide sequence of SEQ ID NO: 19, or (b) a DNA comprising a nucleotide sequence with one or more nucleotide substitutions, deletions, additions, and/or insertions in the nucleotide sequence of SEQ ID NO: 19;

[80] a method for producing a transgenic silkworm that secretes a recombinant antibody into the fat body, comprising the step of producing a silkworm egg that comprises a promoter of a DNA encoding a cytoplasmic actin protein and a DNA encoding a recombinant antibody whose expression is regulated directly or indirectly by the promoter;

[81] the method of [80], wherein the transgenic silkworm comprises the DNAs of (i) and (ii) below:

(i) a DNA encoding a transcriptional regulator operably linked downstream of a promoter of a cytoplasmic actin protein-encoding DNA, and (ii) a DNA encoding a recombinant antibody operably linked downstream of a target promoter of the transcriptional regulator;

[82] the method of [80], wherein the transgenic silkworm is produced by crossing the transgenic silkworms of (i) and (ii) below:

(i) a transgenic silkworm comprising a DNA encoding a transcriptional regulator that is operably linked downstream of a promoter of a cytoplasmic actin protein-encoding DNA, and (ii) a transgenic silkworm comprising a DNA encoding a recombinant antibody that is operably linked downstream of a target promoter of the transcriptional regulator;

[83] the method of [81] or [82], wherein the transcriptional regulator is GAL4 and the target promoter is UAS;

[83-1] the method of [83], wherein the promoter of a cytoplasmic actin protein-encoding DNA is (a) or (b) below:

(a) a DNA comprising the nucleotide sequence of SEQ ID NO: 19, or (b) a DNA comprising a nucleotide sequence with one or more nucleotide substitutions, deletions, additions, and/or insertions in the nucleotide sequence of SEQ ID NO: 19;

[84] a transgenic silkworm which comprises a promoter of a DNA encoding a cytoplasmic actin protein and a DNA encoding a recombinant antibody whose expression is regulated directly or indirectly by the promoter, and which secretes the recombinant antibody into the fat body;

[85] the transgenic silkworm of [84] comprising the DNAs of (i) and (ii) below:

(i) a DNA encoding a transcriptional regulator that is operably linked downstream of a promoter of a cytoplasmic actin protein-encoding DNA, and (ii) a DNA encoding a recombinant antibody that is operably linked downstream of a target promoter of the transcriptional regulator;

[86] the transgenic silkworm of [84] which is produced by crossing the transgenic silkworms of (i) and (ii) below:

(i) a transgenic silkworm comprising a DNA encoding a transcriptional regulator that is operably linked downstream of a promoter of a cytoplasmic actin protein-encoding DNA, and (ii) a transgenic silkworm comprising a DNA encoding a recombinant antibody that is operably linked downstream of a target promoter of the transcriptional regulator;

[87] the transgenic silkworm of [85] or [86], wherein the transcriptional regulator is GAL4 and the target promoter is UAS;

[87-1] the method of [87], wherein the promoter of a cytoplasmic actin protein-encoding DNA is (a) or (b) below:

(a) a DNA comprising the nucleotide sequence of SEQ ID NO: 19, or (b) a DNA comprising a nucleotide sequence with one or more nucleotide substitutions, deletions, additions, and/or insertions in the nucleotide sequence of SEQ ID NO: 19; and

[88] an antibody produced by the method of any one of [1] to [8-1], [32] to [35-1], [50] to [57-1], and [76] to [87-1].

BRIEF DESCRIPTION OF THE DRAWINGS

FIG. 12 depicts photographs showing confirmation of transcription of the IgL gene and IgH gene in the hybrid strain by RT-PCR.

BEST MODE FOR CARRYING OUT THE INVENTION

Figure 1:
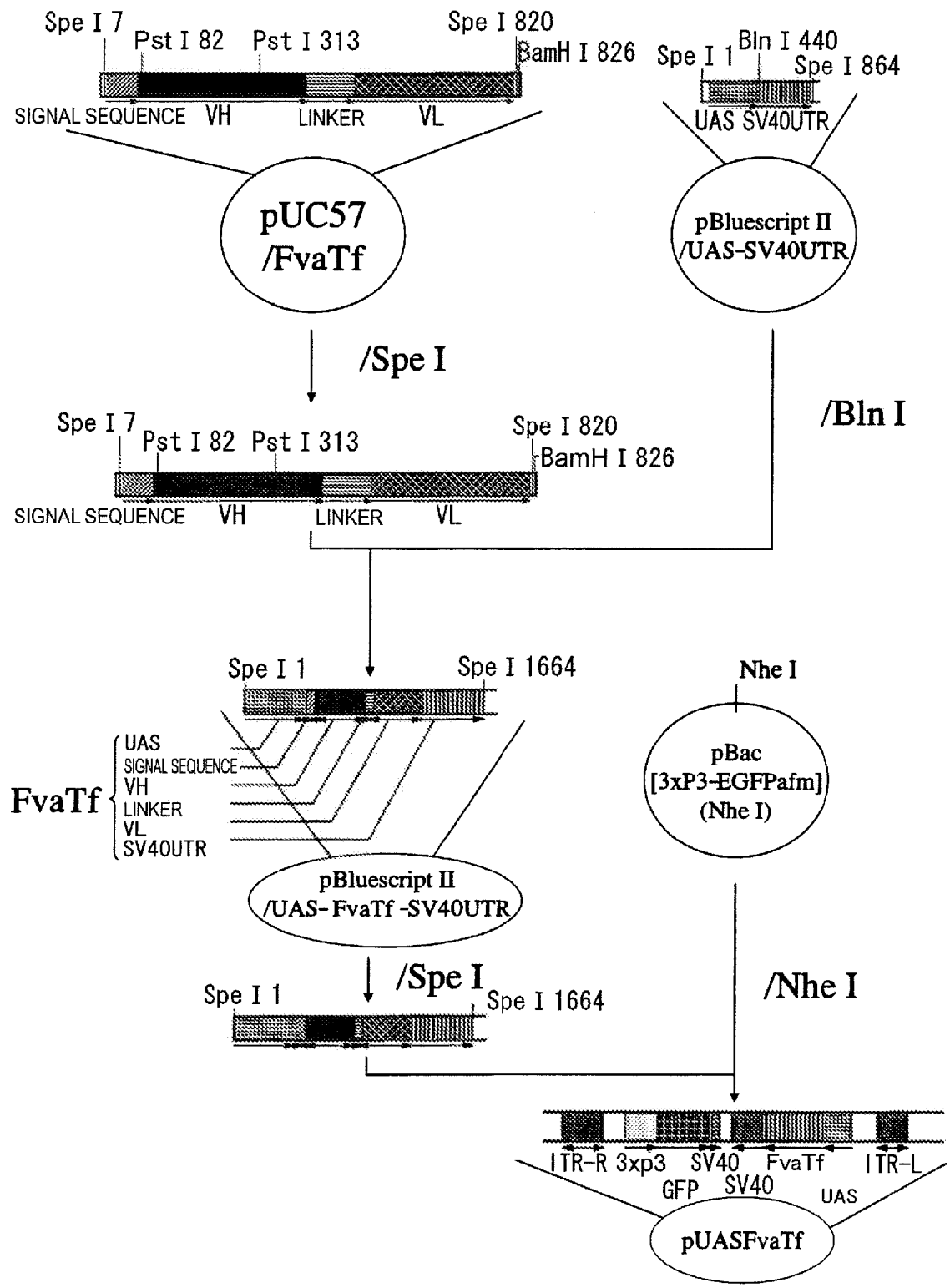
FIG. 1 shows the structure and construction procedure of the pUASFvaTF vector for producing transgenic silkworms.

The present invention relates to methods for producing recombinant antibodies using silkworms. The present invention is based on the successful production of active antibodies in the body of transgenic silkworms accomplished by the present inventors. More specifically, the present invention provides methods for producing a recombinant antibody comprising the steps of:

(a) producing a transgenic silkworm into which a DNA encoding a recombinant antibody has been introduced; and (b) recovering the recombinant antibody from the produced transgenic silkworm.

Furthermore, the present invention provides methods for producing a recombinant antibody comprising the steps of:

(a) producing a transgenic silkworm into which a DNA encoding a recombinant antibody comprising a signal sequence; and (b) recovering the recombinant antibody from the produced transgenic silkworm.

In a specific embodiment of the methods for producing recombinant antibodies of the present invention, the recombinant antibodies are produced in the silk gland of silkworms. More specifically, the present invention relates to methods for producing a recombinant antibody comprising the steps of:

(a) producing a transgenic silkworm which comprises a promoter of a DNA encoding a protein specifically expressed in the silk gland and a DNA encoding a recombinant antibody whose expression is regulated directly or indirectly by the promoter, and which secretes the recombinant antibody into the silk gland; and (b) recovering the recombinant antibody from the produced transgenic silkworm.

The present invention also relates to methods for producing a recombinant antibody comprising the steps of:

(a) producing a transgenic silkworm that comprise a promoter of a DNA encoding a protein specifically expressed in the silk gland, and a DNA encoding a recombinant antibody comprising a signal sequence whose expression is regulated directly or indirectly by the promoter, and which secretes the recombinant antibody into the silk gland; and (b) recovering the recombinant antibody from the produced transgenic silkworm.

In the step of producing the transgenic silkworms of the present invention, silkworm eggs are first produced which comprise a promoter of a DNA encoding a protein specifically expressed in the silk gland, and a DNA encoding a recombinant antibody whose expression is regulated directly or indirectly by the promoter (preferably a recombinant antibody comprising a signal sequence). Next, transgenic silkworms that secrete the recombinant antibody into the silk gland are selected from silkworms that have hatched from the produced silkworm eggs.

In the present invention, transgenic silkworms are selected, for example, by using selection markers. Markers that are conventionally used by those skilled in the art, such as the fluorescent proteins CFP, GFP, YFP, and DsRed, can be used as selection markers of this invention. The use of these markers enables the detection of transgenic silkworms simply by observation using a fluorescence stereomicroscope. Furthermore, since each of the fluorescent colors is different, a plurality of markers can be used simultaneously.

Figure 13:
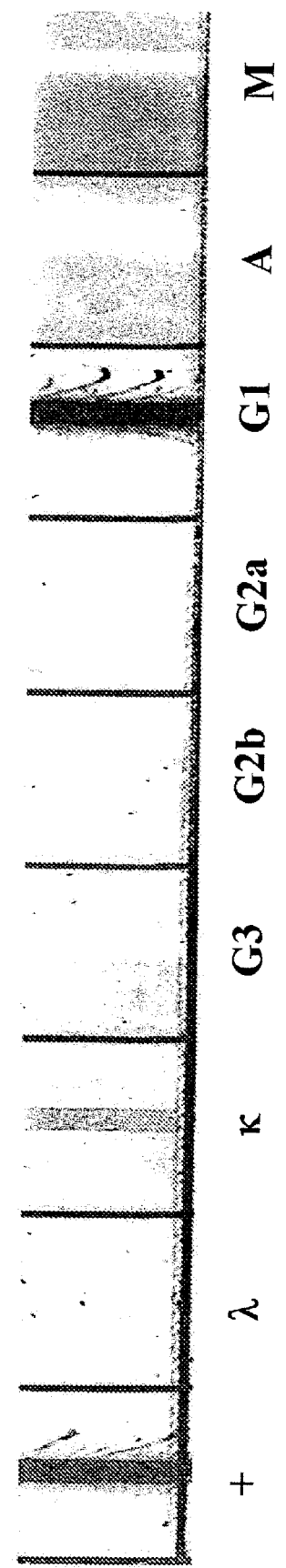
FIG. 13 depicts photographs showing that the recombinant antibody expressed by the hybrid strain is IgG1 and that the immunogenicity of the L chain is kappa.
Figure 14:
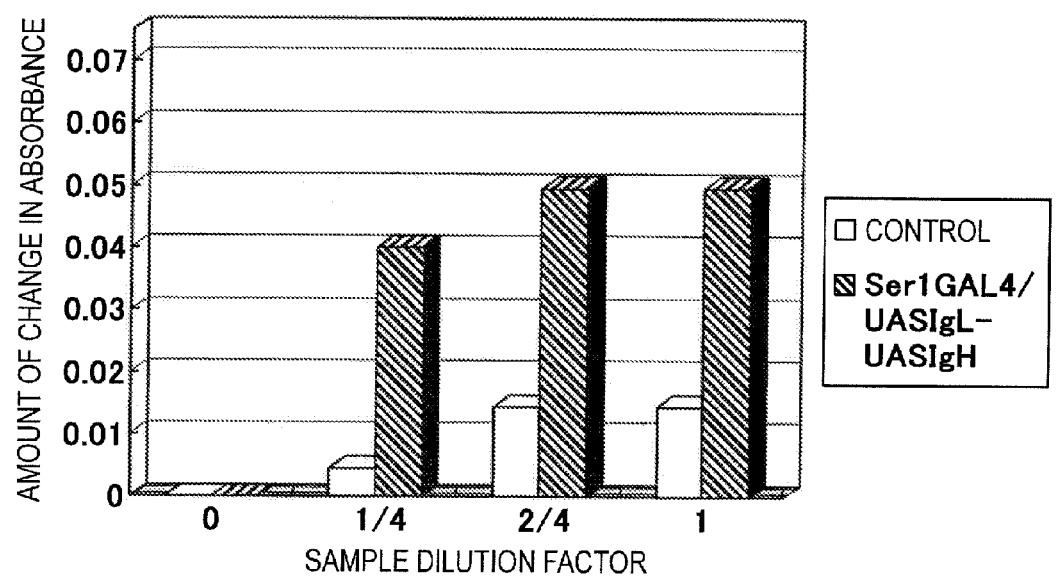
FIG. 14 shows the results of measuring the activity of the recombinant antibody against its antigen by ELISA.

Antibodies that can be produced by the methods of the present invention include both whole antibodies (for example, whole IgG) and low molecular weight antibodies. In the present invention, whole antibodies are not particularly limited, and for example, antibodies derived from humans, mice, rats, rabbits, donkeys, goats, horses, birds, dogs, cats and such can be produced. The antibody isotype is also not limited, and for example, in the case of humans, antibodies of isotype IgG1, IgG2, IgG3, IgG4, IgA1, IgA2, IgD, IgE, or IgM can be produced. Whole antibodies of the present invention are antibodies comprising constant regions such as those having complement-dependent cytotoxic activity or antibody-dependent cytotoxic activity as indicated in the Examples and FIG. 13, and variable regions that recognize antigens as shown in FIG. 14.

On the other hand, low-molecular-weight antibodies of the present invention include antibody fragments in which part of a whole antibody is missing, and they are not particularly limited so long as they have antigen-binding ability. Antibody fragments of the present invention are not particularly limited so long as they are part of a whole antibody, but preferably comprise heavy chain variable regions (VHs) and/or light chain variable regions (VLs). VHs or VLs may contain amino acid substitutions, deletions, additions, and/or insertions in their sequences. Furthermore, part of a VH and\lor VL may be missing, so long as they have antigen-binding ability. The variable regions may be chimerized or humanized. Specific examples of antibody fragments include Fab, Fab', F(ab')2, and Fv. Specific examples of low-molecular-weight antibodies include Fab, Fab', F(ab')2, Fv, scFv (single chain Fv), diabody, and sc(Fv)2 (single chain (Fv)2). Low-molecular-weight antibodies that are particularly preferred in the present invention are scFv antibodies.

Herein, an "Fv" fragment is the smallest antibody fragment, and it comprises a complete antigen recognition site and antigen binding site. An "Fv" is a dimer (VH-VL dimer) in which a single VH and VL are strongly linked by a non-covalent bond. Three complementarity determining regions (CDRs) of each of the variable regions interact with each other to form an antigen-binding site on the surface of the VH-VL dimer. Six CDRs provide the antigen-binding site for an antibody. However, even a single variable region (or half of an Fv which comprises only three CDRs specific to an antigen) can recognize and bind to an antigen, although its affinity is lower than that of an entire binding site.

An scFv comprises an antibody VH and VL, and these regions exist in a single polypeptide chain. In general, an Fv polypeptide further comprises a polypeptide linker between the VH and VL regions, and this enables an scFv to form a structure necessary for antigen binding (for a review on scFv, see Pluckthun "The Pharmacology of Monoclonal Antibodies" Vol. 113, Rosenburg and Moore ed., Springer Verlag, New York, pp. 269-315, 1994). In the present invention, linkers are not particularly limited so long as they do not inhibit expression of the antibody variable regions linked at their ends.

The order of VH and VL is not particularly limited to the arrangement mentioned above, and they can be in any order. Examples include the following arrangements:

N-terminus—signal sequence—[VH]—linker—[VL]—C-terminus

N-terminus—signal sequence—[VL]—linker—[VH]—C-terminus

An scFv antibody of the present invention is preferably an antibody in which a single VH and a single VL are arranged from the N terminal side in the order of VH and VL ([VH] linker [VL]) in a single chain polypeptide. scFvs of the present invention show particularly high antibody activity compared to whole antibodies or other low-molecular-weight antibodies.

Linkers to be used for linking the variable regions of an antibody include arbitrary peptide linkers that can be introduced by genetic engineering and synthetic compound linkers (for example, linkers disclosed in Protein Engineering, 9(3), 299-305, 1996), but peptide linkers are preferred in the present invention. The length of the peptide linkers is not particularly limited and can be suitably selected according to the purpose by those skilled in the art. Typically, the length is 1 to 100 amino acids, preferably 3 to 50 amino acids, more preferably 5 to 30 amino acids, and particularly preferably 12 to 18 amino acids (for example, 15 amino acids). Examples of linkers in the present invention include linkers comprising the amino acid sequence of SEQ ID NO: 9.

Furthermore, a preferred embodiment of the recombinant antibodies of the present invention includes human antibodies, mouse antibodies, and modified antibodies such as humanized antibodies, chimeric antibodies, and antibodies from organisms other than humans and mice.

A chimeric antibody is produced by combining sequences derived from different animals, and includes, for example, an antibody comprising the heavy and light chain variable regions of a mouse antibody and the heavy and light chain constant regions of a human antibody. A chimeric antibody can be obtained using known methods, for example, by linking a DNA encoding antibody V regions with a DNA encoding human antibody C regions, incorporating this into an expression vector, and then introducing the vector into a host to produce the antibody.

Humanized antibodies are also referred to as "reshaped human antibodies", which are obtained by grafting a complementarity determining region (CDR) of an antibody derived from a non-human mammal such as mouse to a CDR of a human antibody, and common genetic engineering techniques for this purpose are also known (See, European Patent Application Publication No. 125023 and WO 96/02576).

Specifically, a DNA sequence designed to link a mouse antibody CDR to a human antibody framework region (FR) is synthesized by PCR using several oligonucleotides prepared to contain overlapping portions of the terminal regions of both the CDR and FR as primers (see the methods described in WO98/13388).

Human antibody framework regions to be linked via CDRs are selected so that CDRs form a favorable antigen-binding site. Amino acids in the framework region of an antibody variable region may be substituted as necessary, so that the complementarity determining regions of a reshaped human antibody form a suitable antigen-binding site (Sato, K. et al., Cancer Res. (1993) 53, 851-856).

Human antibody constant regions are used as constant regions in chimeric antibodies and humanized antibodies, and for example, Cγ1, Cγ2, Cγ3, or Cγ4 can be used for H chains and Cκ or Cλ, can be used for L chains. Furthermore, human antibody constant regions can be modified to improve antibody stability or stability in antibody production.

Generally, a chimeric antibody comprises an antibody variable region derived from a non-human mammal and a constant region derived from a human antibody. On the other hand, a humanized antibody comprises antibody CDRs derived from a non-human mammal, and a framework region and constant region derived from a human antibody.

Amino acids in the variable region (for example, FR) and constant region can be substituted with other amino acids and such after a chimeric antibody or humanized antibody is produced.

The origin of the variable region in a chimeric antibody or of CDRs in a humanized antibody is not particularly limited, and it may be derived from any animal. For example, sequences of mouse antibodies, rat antibodies, rabbit antibodies, and camel antibodies can be used. Without limitation, preferred antibodies in the present invention include mouse antibodies.

Antigens to which the antibodies (whole antibodies and low-molecular-weight antibodies) produced in the present invention bind are also not particularly limited. Those skilled in the art can design antibodies that bind to an antigen of interest using known techniques. The present invention relates to methods for producing antibodies which have been designed in this manner to bind to desired antigens by using known techniques. The present invention also relates to antibodies produced by these methods.

As an example, antibodies that bind to human transferrin were produced in the present invention. The amino acid sequence of the H chain variable region of an anti-human transferrin scFv antibody is shown in SEQ ID NO: 6, and the amino acid sequence of the L chain variable region of an anti-human transferrin scFv antibody is shown in SEQ ID NO: 12. Furthermore, the amino acid sequence of an IgG1 antibody H chain variable region is shown in SEQ ID NO: 31 and the amino acid sequence of an IgG1 antibody L chain variable region is shown in SEQ ID NO: 23. As described later, such antibodies can be used for disease diagnosis and such, for example, as diagnostic agents for diabetic nephropathy, and for measuring the amount of transferrin in a living body, and evaluating nutrition assessment, and such.

An example of other embodiments of the antibodies provided by the present invention includes antibodies that bind to carcinoembryonic antigen (CEA). At present, CEA is widely used as a tumor marker. The tumor marker is observed not only in tumors of the digestive system, such as stomach cancer and esophageal cancer, but also in various organ tumors, for example, tumors of the respiratory and circulatory systems such as lung cancer. Therefore, antibodies that bind to CEA are useful for detecting recurrence of tumors or observing courses of treatment. An alternative example is antibodies that bind to c-erbB-2. c-erbB-2 is expressed in tumor cells of the glandular system that have undergone blastogenesis. Antibodies that bind to c-erbB-2 are useful for histopathological detection of tumors. Another example is antibodies that bind to haptoglobin. Haptoglobin is a type of protein secreted into the blood from the liver. This protein binds to free hemoglobin. Thus, antibodies that bind to haptoglobin are useful for measuring haptoglobin in plasma.

Antibodies produced in the present invention include, for example, antibodies against CRP, IgG, IgA, IgM, IgD, IgE, albumin, prealbumin, complement C3, complement C4, α-1 microglobulin, β-2 microglobulin, AFP, CA 19-9, CA15-3, PSA, apolipoprotein, tumor necrosis factor, interleukin, interferon, osteopontin, HBs antigen, RF, HCG, collagen, Hb, HbAlc, HCV antibody, troponin, myoglobin, and FDP, but are not limited thereto. The antibodies are not particularly limited so long as they bind to substances that can be applied to the field of medicine. Furthermore, the antibodies are not limited to those that bind to proteins, and also include antibodies against low-molecular-weight compounds such as endocrine disrupting chemicals. Antibodies that bind to desired antigens can be produced by suitably modifying variable regions or hypervariable regions in H chains or L chains of the antibodies that bind to human transferrin described in the Examples.

In the present invention, secretion signals (signal sequences) are preferably used for maintaining activities of the produced recombinant antibodies or for promoting the secretion of the antibodies to increase the amount of recovered antibodies. Secretory proteins or integral membrane proteins must pass through a lipid bilayer after they are synthesized in endoplasmic reticulum membrane-bound ribosomes. Signal sequences are amino acid residues located at the N termini of proteins, and are necessary for this event.

Signal sequences in the present invention are not particularly limited so long as they have the above-mentioned function. An example includes animal-derived signal sequences. Other examples are animal antibody-derived signal sequences. Examples of animals include humans, mice, rats, rabbits, donkeys, goats, horses, birds, dogs, cats, yeasts, and insects.

Examples of preferred signal sequences of the present invention include acid phosphatase signal sequences. The origins of acid phosphatases are not particularly limited, and include, for example, humans, mice, rats, rabbits, donkeys, goats, horses, birds, dogs, cats, yeasts, and insects.

Signal sequences that are particularly preferred in the present invention are human acid phosphatase signal sequences, mouse immunoglobulin L chain κ signal sequences, and mouse IgG1 signal sequences. These signal sequences can be used to promote the transfer of expressed recombinant antibodies to the silk gland lumen. Accordingly, signal sequences are preferably used in the present invention.

When using a signal sequence, a preferred example of a human acid phosphatase signal sequence in the present invention is a protein comprising the amino acid sequence of SEQ ID NO: 3. A preferred example of a mouse immunoglobulin L chain κ signal sequence in the present invention is a protein comprising the amino acid sequence of SEQ ID NO: 21. A preferred example of a mouse IgG1 signal sequence in the present invention is a protein comprising the amino acid sequence of SEQ ID NO: 29. Furthermore, so long as a protein has an activity equivalent to that of the protein of any one of SEQ ID NOs: 3, 21, and 29, it may comprise an amino acid sequence with one or more amino acid substitutions, deletions, additions, and/or insertions in the amino acid sequence of any one of SEQ ID NOs: 3, 21, and 29. The phrase "functionally equivalent" means that a protein of interest has a biological or biochemical activity similar to that of a protein comprising the amino acid sequence of any one of SEQ ID NOs: 3, 21, and 29.

A signal sequence in the present invention is preferably linked to the N terminus of a recombinant antibody, but it is not limited thereto.

Accordingly, particularly preferred embodiments of antibodies of the present invention include antibodies that bind to transferrin, CEA, c-erbB-2, or haptoglobin and comprise signal sequences of human acid phosphatases, mouse immunoglobulin L chains κ, or mouse IgG1s. Among them, scFv mouse antibodies that bind to transferrin and comprise signal sequences of human acid phosphatases are particularly preferred as antibodies of the present invention. Such antibodies comprise the amino acid sequence of SEQ ID NO: 15. Antibodies which comprise an amino acid sequence with one or more amino acid substitutions, deletions, additions, and/or insertions in the amino acid sequence of SEQ ID NO: 15, and which have an activity equivalent to that of antibodies comprising the amino acid sequence of SEQ ID NO: 15, are also preferred as antibodies of the present invention.

In the present invention, antibodies that bind to transferrin, CEA, c-erB-2, or haptoglobin, and comprise L chains carrying a mouse immunoglobulin L chain κ signal sequence and H chains carrying a mouse IgG1 signal sequence, are also particularly preferred. Such antibodies comprise L chains comprising the amino acid sequence of SEQ ID NO: 49 and H chains comprising the amino acid sequence of SEQ ID NO: 51. Furthermore, antibodies that comprise L chains comprising an amino acid sequence with one or more amino acid substitutions, deletions, additions, and/or insertions in the amino acid sequence of SEQ ID NO: 49, which have an activity equivalent to that of antibodies comprising the amino acid sequence of SEQ ID NO: 49, and that comprise H chains comprising an amino acid sequence with one or more amino acid substitutions, deletions, additions, and/or insertions in the amino acid sequence of SEQ ID NO: 51, which have an activity equivalent to that of antibodies comprising the amino acid sequence of SEQ ID NO: 51, are particularly preferred as antibodies of the present invention.

An example of a preferred embodiment of a DNA encoding an scFv mouse antibody that binds to transferrin and comprises a human acid phosphatase signal sequence is a DNA comprising the nucleotide sequence of SEQ ID NO: 13, or more preferably a DNA comprising the nucleotide sequence of SEQ ID NO: 14. A further example is a DNA encoding a protein which comprises a sequence with one or more amino acid substitutions, deletions, additions, and/or insertions in the nucleotide sequence of SEQ ID NO: 13 (or more preferably SEQ ID NO: 14), and has a function equivalent to that of the DNA of SEQ ID NO: 13 (or more preferably SEQ ID NO: 14).

A preferred embodiment of a DNA encoding an L chain of an antibody that binds to transferrin, in which the L chain comprises a mouse immunoglobulin L chain κ signal sequence, includes a DNA comprising the nucleotide sequence of SEQ ID NO: 48. A further example is a DNA comprising a sequence with one or more amino acid substitutions, deletions, additions, and/or insertions in the nucleotide sequence of SEQ ID NO: 48, which has a function equivalent to that of the DNA of SEQ ID NO: 48.

Moreover, a preferred embodiment of a DNA encoding an H chain of an antibody that binds to transferrin, in which the H chain comprises a signal sequence of a mouse IgG1, includes a DNA comprising the nucleotide sequence of SEQ ID NO: 50. A further example is a DNA comprising a sequence with one or more amino acid substitutions, deletions, additions, and/or insertions in the nucleotide sequence of SEQ ID NO: 50, which has a function equivalent to that of the DNA of SEQ ID NO: 50.

When designing DNAs to encode antibodies (preferably antibodies comprising signal sequences) of the present invention, these codons are preferably converted to those for insects. Conversion to insect codons can increase the expression level of recombinant antibodies. As an example, for an scFv mouse antibody comprising a human acid phosphatase signal sequence, the nucleotide sequence before converting the signal sequence codons is shown in SEQ ID NO: 1, and the nucleotide sequence after converting these codons is shown in SEQ ID NO: 2. Similarly, the nucleotide sequences of an H chain variable region (VH) before and after codon conversion are shown in SEQ ID NOs: 4 and 5, respectively; the nucleotide sequences of an L chain variable region (VL) before and after codon conversion are shown in SEQ ID NOs: 10 and 11, respectively; the nucleotide sequence of a linker sequence is shown in SEQ ID NO: 7 and the nucleotide sequence after codon conversion is shown in SEQ ID NO: 8; and the nucleotide sequences of the whole antibody before and after codon conversion are shown in SEQ ID NOs: 13 and 14, respectively.

In the scFv mouse antibodies against human transferrin of the present invention, the codons in H chain and L chain regions of the antibodies were converted from those used in mice, which are vertebrates, to those used in insects. More specifically, in the present invention, the codons of the scFv mouse antibodies against human transferrin were converted to codons that are frequently used in *Spodoptera frugiperda*, which is a species related to *Spodoptera litura* and is also an insect just like silkworm. Furthermore, codons frequently used in *Spodoptera frugiperda* were also used for the linker portion of scFv antibodies.

More specifically, in the present invention, for a total of 153 amino acids in human and mouse-derived codons and codons of linker portions, their corresponding codons were converted to codons that are frequently used in *Spodoptera frugiperda*, a species related to *Spodoptera litura*, as shown in Table 1 (The sequence before conversion corresponds to SEQ ID NO: 13, and the sequence after conversion corresponds to SEQ ID NO: 14. "1st codon" in Table 1 indicates the position of the first nucleotide of a codon in the nucleotide sequence of SEQ ID NO: 13. For example, the value "13" in the 1st codon means that the codon converted in SEQ ID NO: 13 is composed of the nucleotides at positions 13 to 15 (in this case, G at position 15 is converted to C)). DNAs encoding antibodies of the present invention include DNAs in which at least one of these codons has been converted. Furthermore, in the present invention, codons can be converted to those frequently used in fruit flies, silkworms, honeybees and such, and DNAs in which codons have been converted to those frequently used in these insects are also included in the present invention. Codons that are frequently used in these insects are well known. Accordingly, in the present invention, DNAs whose codons have been converted to insect codons are included in designing DNAs to encode scFv mouse antibodies comprising a human acid phosphatase signal sequence.

TABLE 1

| 1st Codon | Before Conversion | After Conversion | Amino Acid |
|---|---|---|---|
| 13 | ACG | ACC | T |
| 16 | GCG | GCT | A |
| 34 | GCC | GCT | A |
| 37 | TTG | CTG | L |
| 40 | TTG | CTC | L |
| 43 | CTA | CTG | L |
| 58 | CTC | CTG | L |
| 61 | GAG | GAA | E |
| 64 | GTC | GTG | V |
| 67 | CAG | CAA | Q |
| 73 | CAG | CAA | Q |
| 76 | GAG | GAA | E |
| 79 | TCG | TCC | S |
| 82 | GGA | GGT | G |
| 85 | CCT | CCC | P |
| 88 | GAC | GAT | D |
| 100 | CCT | CCC | P |
| 103 | TCT | TCC | S |
| 106 | CAG | CAA | Q |
| 109 | TCA | TCC | S |
| 112 | CTT | CTG | L |
| 115 | TCA | TCO | S |
| 118 | CTC | CTG | L |
| 127 | ACT | ACC | T |
| 130 | GTC | GTG | V |
| 133 | ACT | ACC | T |
| 136 | GGC | GGT | G |
| 151 | AGT | TCC | S |
| 157 | TAT | TAC | Y |
| 160 | AGC | TCC | S |
| 172 | ATT | ATC | I |
| 175 | CGG | AGG | R |
| 181 | TTT | TTC | F |
| 184 | CCA | CCC | P |
| 187 | GAA | GAG | E |
| 193 | AAA | AAG | K |
| 199 | GAA | GAG | E |
| 208 | GGC | GGT | G |
| 214 | ATA | ATC | I |
| 223 | AGT | TCC | S |
| 229 | GCC | GCT | A |
| 232 | ACT | ACC | T |
| 241 | AGC | TCC | S |
| 244 | CCA | CCC | P |
| 247 | TCT | TCC | S |
| 250 | CTC | CTG | L |
| 253 | AAA | AAG | K |
| 256 | AGT | TCC | S |
| 259 | CGA | CGT | R |
| 265 | TCT | TCC | S |
| 271 | ACT | ACC | T |
| 274 | AGA | CGT | R |
| 280 | ACA | ACC | T |
| 304 | CAG | CAA | Q |
| 307 | TTG | CTG | L |
| 313 | TCT | TCC | S |
| 319 | ACT | ACC | T |
| 322 | ACT | ACC | T |
| 325 | GAG | GAA | E |
| 328 | GAC | GAT | D |
| 331 | ACA | ACC | T |
| 334 | GCC | GCT | A |
| 337 | ACA | ACC | T |
| 340 | TAT | TAC | Y |
| 346 | TGT | TGC | C |
| 349 | GCA | GCT | A |
| 352 | AGG | CGT | R |
| 367 | CCT | CCC | P |
| 373 | TAT | TAC | Y |
| 385 | TAT | TAC | Y |
| 391 | GGC | GGT | G |
| 397 | GGG | GGT | G |
| 403 | ACG | ACC | T |
| 406 | GTC | GTG | V |
| 418 | TCA | TCC | S |
| 421 | GGT | GGC | G |
| 424 | GGA | GGC | G |
| 430 | GGT | GGC | G |
| 433 | TCA | TCC | S |
| 439 | GGA | GGT | G |
| 448 | TCT | TCC | S |
| 451 | GGC | GGT | G |
| 457 | GGC | GGT | G |
| 460 | GGA | GGT | G |
| 463 | TCG | TCC | S |
| 466 | GAC | GAT | D |
| 469 | ATT | ATC | I |
| 472 | GAG | GAA | E |

TABLE 1-continued

| 1st Codon | Before Conversion | After Conversion | Amino Acid |
|---|---|---|---|
| 475 | CTC | CTG | L |
| 481 | CAG | CAA | Q |
| 484 | TCT | TCC | S |
| 487 | CCA | CCC | P |
| 496 | CTA | CTG | L |
| 505 | TCA | TCC | S |
| 508 | GTT | GTG | V |
| 511 | GGA | GGT | G |
| 520 | GTT | GTG | V |
| 523 | ACT | ACC | T |
| 541 | AGT | TCC | S |
| 547 | AGC | TCC | S |
| 550 | CTT | CTG | L |
| 553 | TTA | CTC | L |
| 556 | TAT | TAC | Y |
| 559 | AGT | TCC | S |
| 565 | AAT | AAC | N |
| 568 | CAA | CAG | Q |
| 580 | TTG | CTG | L |
| 583 | GCC | GCT | A |
| 592 | CAG | CAA | Q |
| 595 | CAG | CAA | Q |
| 601 | CCA | CCC | P |
| 604 | GGG | GGT | G |
| 610 | TCT | TCC | S |
| 613 | CCT | CCC | P |
| 616 | AAA | AAG | K |
| 622 | CTG | CTC | L |
| 625 | ATT | ATC | I |
| 634 | GCA | GCT | A |
| 640 | ACT | ACC | T |
| 643 | AGG | CGT | R |
| 649 | TCT | TCC | S |
| 652 | GGG | GGT | G |
| 655 | GTC | GTG | V |
| 658 | CCT | CCC | P |
| 664 | CGC | CGT | R |
| 670 | ACA | ACC | T |
| 673 | GGC | GGT | G |
| 676 | AGT | TCC | S |
| 679 | GGA | GGT | G |
| 682 | TCT | TCC | S |
| 685 | GGG | GGT | G |
| 688 | ACA | ACC | T |
| 691 | GAT | GAC | D |
| 697 | ACT | ACC | T |
| 700 | CTC | CTG | L |
| 709 | AGC | TCC | S |
| 712 | AGT | TCC | S |
| 724 | GAA | GAG | E |
| 733 | TCA | TCC | S |
| 736 | GTT | GTG | V |
| 739 | TAT | TAC | Y |
| 745 | TGT | TGC | C |
| 754 | TAT | TAC | Y |
| 757 | TAT | TAC | Y |
| 760 | AGC | TCC | S |
| 763 | TAT | TAC | Y |
| 766 | CCT | CCC | P |
| 772 | ACG | ACC | T |
| 778 | GGC | GGT | G |
| 781 | TCG | TCC | S |
| 784 | GGC | GGT | G |
| 796 | GAA | GAG | E |
| 802 | AAA | AAG | K |

In the present invention, the above-mentioned recombinant antibodies are secreted into the silk gland. The silk gland is an organ that exists as a pair in the silkworm body, and synthesizes silk proteins. The silk gland can be divided into the posterior, middle, and anterior silk glands, and silk protein synthesis takes place in the posterior and middle silk glands. Preferred silk glands in the present invention are the middle and posterior silk glands.

Antibodies produced by the methods of the present invention are not particularly limited so long as they are produced by the methods of the present invention, and they may or may not comprise a signal sequence. More specifically, antibodies produced by the methods of the present invention for producing antibodies include both antibodies with and without a signal sequence.

In the present invention, examples of a silkworm egg comprising a promoter of a DNA encoding a protein that is specifically expressed in the silk gland and a DNA encoding a recombinant antibody whose expression is regulated directly by the promoter include a silkworm egg comprising a DNA in which a recombinant antibody-encoding DNA is operably linked downstream of a promoter of a DNA encoding a protein that is specifically expressed in the silk gland. Such a silkworm egg can be produced by introducing a DNA in which a recombinant antibody-encoding DNA is operably linked downstream of a promoter of a DNA encoding a protein that is specifically expressed in the silk gland into a silkworm egg.

In the present invention, examples of a silkworm egg comprising a promoter of a DNA encoding a protein that is specifically expressed in the silk gland and a DNA encoding a recombinant antibody protein whose expression is regulated indirectly by the promoter include a silkworm egg comprising (i) a DNA in which a DNA encoding a transcriptional regulator is operably linked downstream of a promoter of a DNA encoding a protein that is specifically expressed in the silk gland, and (ii) a DNA in which a recombinant antibody-encoding DNA is operably linked downstream of a target promoter of the transcriptional regulator.

In the present invention, a DNA encoding a recombinant antibody whose expression is regulated directly or indirectly by a promoter of a DNA encoding a protein that is specifically expressed in the silk gland is preferably a DNA comprising a signal sequence to promote antibody secretion and to increase the amount of recovered antibody. Specific embodiments of the signal sequence are described above.

The phrase "operably linked" means that a promoter and a DNA are linked, so that expression of the DNA located downstream of the promoter is induced by the binding of a transcriptional regulator to the promoter. Therefore, even if the DNA is linked to another gene and a fusion protein is produced from the linked genes, as long as the expression of the fusion protein is induced by the binding of the transcriptional regulator to the promoter, this DNA can be considered to be "operably linked" as described above.

Examples of the combination of the transcriptional regulator and target sequence include GAL4 and UAS, and TetR and TRE. By using GAL4 and UAS, or TetR and TRE, the expression site, timing, and level of a gene of interest can be regulated precisely, and the gene can be easily expressed in many tissues. Furthermore, a strain can be established even if a gene to be expressed is a lethal gene.

A variety of methods can be selected as methods for producing the above-mentioned silkworm eggs. For example, the above-described DNAs of (i) and (ii) can be introduced into separate silkworm eggs. Silkworm eggs comprising both DNAs can be obtained by crossing the transgenic silkworms with each other that are derived from the silkworm eggs into which the individual DNAs have been introduced. In this case, the tissue of expression, expression timing and level and such can be adjusted by the transcriptional regulators. Therefore, this method is advantageous in that by crossing with a strain into which a gene to be expressed has been introduced, the tissue of expression, expression timing and level and such can be altered without generating many strains. Experiments can still be carried out despite the infertility that may be caused by expression of the gene of interest. An additional advantage is an increased level of the product of the introduced gene compared to when a single promoter is used. Alternatively, silkworm eggs comprising the DNAs of (i) and (ii) can be obtained by artificially introducing one of the DNAs into eggs ovipositioned by a transgenic silkworm into which the other DNA has been introduced. Silkworm eggs comprising the DNAs of (i) and (ii) can also be obtained by introducing both DNAs into the same egg (Imamura, M., Nakai, J., Inoue, S., Quan, G.-X., Kanda, T. and Tamura, T. (2003) Targeted gene expression using the GAL4/UAS system in the silkworm *Bombyx mori*. Fourth International Workshop on Transgenesis and Genomics of Invertegrate Organisms, Asilomar, p. 53).

DNAs can be introduced into silkworm eggs, for example, according to the method for injecting transposons as vectors into silkworm eggs in the early developmental stage (Tamura, T., Thibert, C., Royer, C., Kanda, T., Abraham, E., Kamba, M., Komoto, N., Thomas, J.-L., Mauchamp, B., Chavancy, G., Shirk, P., Fraser, M., Prudhomme, J.-C. and Couble, P., 2000, Nature Biotechnology 18, 81-84). For example, vectors in which the above-described DNAs have been inserted into inverted terminal repeats of the transposons (Handler A M, McCombs S D, Fraser M J, Saul S H. (1998) Proc. Natl. Acad. Sci. U.S.A. 95(13): 7520-5) are introduced into silkworm eggs along with vectors comprising DNAs encoding transposases (helper vectors). An example of a helper vector is pHA3PIG (Tamura, T., Thibert, C., Royer, C., Kanda, T., Abraham, E., Kamba, M., Komoto, N., Thomas, J.-L., Mauchamp, B., Chavancy, G., Shirk, P., Fraser, M., Prudhomme, J.-C. and Couble, P., 2000, Nature Biotechnology 18, 81-84), but is not limited thereto.

An example of the transposons of the present invention is preferably piggyBac, but is not limited thereto. Transposons such as mariner and minos may be used (Shimizu, K., Kamba, M., Sonobe, H., Kanda, T., Klinakis, A. G., Savakis, C. and Tamura, T. (2000) Insect Mol. Biol., 9, 277-281; Wang W, Swevers L, Iatrou K. (2000) Insect Mol Biol 9 (2): 145-55).

In the present invention, transgenic silkworms can also be produced using baculovirus vectors (Yamao, M., N. Katayama, H. Nakazawa, M. Yamakawa, Y. Hayashi et al., 1999, Genes Dev 13: 511-516).

In the middle silk gland, a promoter of a DNA encoding a protein that is specifically expressed in the silk gland in the present invention is, for example, a promoter of a DNA encoding the sericin 1 protein or sericin 2 protein. Examples of a promoter of a DNA encoding the sericin 1 protein or sericin 2 protein include DNAs comprising the nucleotide sequence of SEQ ID NO: 16 or 17. Examples of the DNAs comprising the nucleotide sequence of SEQ ID NO: 16 or 17 are DNAs consisting of the nucleotide sequence of SEQ ID NO: 16 or 17, and DNAs comprising the upstream regions or downstream regions of DNAs consisting of the nucleotide sequence of SEQ ID NO: 16 or 17, but are not limited thereto. The upstream regions and downstream regions of DNAs consisting of the nucleotide sequence of SEQ ID NO: 16 or 17 are disclosed in references: Okamoto, H., Ishikawa, E. and Suzuki, Y. (1982) Structural analysis of sericin genes. Homologies with fibroin gene in the 5' flanking nucleotide sequences. J. Biol. Chem., 257, 15192-15199; Garel, A., Deleage, G. and Prudhomme, J. C. (1997) Structure and organization of the *Bombyx mori* sericin 1 gene and of the sericins 1 deduced from the sequence of the Ser 1B cDNA. Insect Biochem. Mol. Biol., 27, 469-477; Michaille, J. J., Garel, A. and Prudhomme, J. C. (1990) Cloning and characterization of the highly polymorphic Ser2 gene of *Bombyx mori*. Gene, 86, 177-184.

Furthermore, in the present invention, an example of a promoter of a DNA encoding a protein that is specifically expressed in the middle silk gland, may be a DNA that is structurally similar to a DNA comprising the nucleotide sequence of SEQ ID NO: 16 or 17, and that has promoter activity equivalent to or improved compared to the activity of a DNA comprising the nucleotide sequence of SEQ ID NO: 16 or 17. Such a DNA may be, for example, a DNA comprising a nucleotide sequence with one or more nucleotide substitutions, deletions, additions, and/or insertions in the nucleotide sequence of SEQ ID NO: 16 or 17. This DNA can be produced by methods such as hybridization techniques, polymerase chain reaction (PCR) techniques, site-directed mutagenesis, and DNA synthesis. Whether the prepared DNAs have promoter activity can be examined by those skilled in the art, for example, using well-known reporter assays with reporter genes.

The reporter genes are not particularly limited as long as their expression is detectable, and include the CAT gene, lacZ gene, luciferase gene, β-glucuronidase gene (GUS), and GFP gene, which are generally used by those skilled in the art. The expression level of the reporter genes can be measured according to the type of the reporter genes by methods well known to those skilled in the art. For example, when the reporter gene is the CAT gene, the expression level of the reporter gene can be measured by detecting the acetylation of chloramphenicol catalyzed by the gene product. The expression level of the reporter gene can be measured by: detecting the color development of pigment compound as a result of the catalytic action of the gene expression product when the reporter gene is the lacZ gene; detecting the fluorescence of fluorescent compound as a result of the catalytic action of the gene expression product when the reporter gene is the luciferase gene; detecting the luminescence of Glucuron (ICN) or the color development of 5-bromo-4-chloro-3-indolyl-β-glucuronide (X-Glue) as a result of the catalytic action of the gene expression product when the reporter gene is the β-glucuronidase gene (GUS); and detecting the fluorescence of the GFP protein when the reporter gene is the GFP gene.

On the other hand, in the present invention, a promoter of a DNA encoding a protein that is specifically expressed in the posterior silk gland is, for example, a promoter of a DNA encoding the fibroin L chain protein. Examples of a promoter of a DNA encoding the fibroin protein include DNAs comprising the nucleotide sequence of SEQ ID NO: 18. Examples of a DNA comprising the nucleotide sequence of SEQ ID NO: 18 include DNAs consisting of the nucleotide sequence of SEQ ID NO: 18, and DNAs comprising upstream regions or downstream regions of DNAs consisting of the nucleotide sequence of SEQ ID NO: 18, but are not limited thereto. The upstream regions and downstream regions of DNAs consisting of the nucleotide sequence of SEQ ID NO: 18 are disclosed in KIKUCHI, Y., K. MORI, S. SUZUKI, K. YAMAGUCHI and S. MIZUNO, 1992 Structure of the *Bombyx mori* fibroin light-chain-encoding gene: upstream sequence elements common to the light and heavy chain. Gene 110: 151-158).

Furthermore, in the present invention, a promoter of a DNA encoding a protein that is specifically expressed in the posterior silk gland is, for example, a DNA which is structurally similar to a DNA comprising the nucleotide sequence of SEQ ID NO: 18 and has a promoter activity that is equivalent to or improved compared to a DNA comprising the nucleotide sequence of SEQ ID NO: 18. Such promoters can be prepared by methods described above.

Methods of the present invention for producing recombinant antibodies comprise the step of recovering antibodies synthesized in the silkworm body. Synthesized antibodies are secreted into the middle or posterior silk gland in their active form without being insolubilized. Therefore, recombinant antibodies can be recovered from the middle or posterior silk gland. As an example of methods for recovering recombinant antibodies from the middle or posterior silk gland, silkworms are dissected at the spinning stage, the middle or posterior silk gland is removed and placed in 20 mM Tris-HCl pH7.4, and then the silk gland is cut with a pair of tweezers or a scalpel to recover recombinant antibodies from the silk gland.

The recombinant antibodies of the present invention can also be recovered, for example, from cocoons spun by the transgenic silkworms. Examples of methods for recovering proteins include methods well known to those skilled in the art, such as the method in which cocoons are dissolved in 60% LiSCN and then dialyzed in 20 mM Tris and 5 M urea to recover proteins (Inoue, S., Tsuda, H., Tanaka, H., Magoshi, Y., and Mizuno (2001) Sericologia 4, 157-163). Other feasible methods for recovering proteins include methods using surfactants and methods comprising the step of dissolving in aqueous solution.

The silkworms of the present invention are not particularly limited. However, in order to produce large amounts of recombinant antibodies, it is preferable to use silkworms in which the production of proteins constituting the silk thread, such as the fibroin protein, is suppressed by mutations in DNA regions (including coding regions, promoter regions, and untranslated regions) that encode the proteins constituting the silk thread. Examples of such silkworms include mutant silkworm strains in which the production of proteins constituting the silk thread is suppressed by mutations in DNA regions encoding these proteins; and preferably include exarate pupae of silkworms in which the production of proteins constituting the silk thread is suppressed by such mutations; or more preferably include the silkworm strain Nd-s$^D$. However, any silkworms are appropriate as long as the production of proteins constituting the silk thread is suppressed, regardless of whether suppression of the production of such proteins is caused artificially or depends on naturally-occurring mutations.

An embodiment of such silkworms is a silkworm well known to those skilled in the art as a sericin silkworm. The use of sericin silkworms facilitates purification of antibodies synthesized from DNAs encoding recombinant antibodies which have been introduced into the chromosome. Furthermore, when producing recombinant antibodies in the posterior silk gland, sericin silkworms are preferably used in terms of the amount of production.

Silkworms having the characteristic of ovipositing nondiapausing eggs, as well as silkworms having the characteristic of ovipositing diapausing eggs (for example, silkworm varieties for practical use, including Gunma, 200, Shunrei, Shogetsu, Kinshu, and Showa) can be used as the silkworms of the present invention. Herein, the term "diapausing eggs" refers to eggs in which embryogenesis after oviposition is transiently stopped, and the term "nondiapausing eggs" refers to eggs in which embryogenesis after oviposition does not stop, and leads to larval hatching.

When silkworms having the characteristic of ovipositing diapausing eggs are used, DNAs are introduced into the nondiapausing eggs after they have been laid. For example, the silkworm variety Gunma can be induced to oviposit nondiapausing eggs, by methods of culturing diapausing eggs at 15° C. to 21° C. to induce adults hatched from the diapausing eggs to oviposit nondiapausing eggs, preferably by methods of culturing diapausing eggs at 16° C. to 20° C. to induce adults hatched from the diapausing eggs to oviposit nondiapausing eggs, more preferably by methods of culturing diapausing eggs at 18° C. to induce adults hatched from the diapausing eggs to oviposit nondiapausing eggs, and most preferably by methods of culturing diapausing eggs at 18° C. and rearing larvae hatched from the diapausing eggs under continuous light to induce the reared adults to oviposit nondiapausing eggs. The silkworm variety 200 can be induced to oviposit nondiapausing eggs, by methods of culturing diapausing eggs at 15° C. to 21° C. to induce adults hatched from the diapausing eggs to oviposit nondiapausing eggs, preferably by methods of culturing diapausing eggs at 16° C. to 20° C. to induce adults hatched from the diapausing eggs to oviposit nondiapausing eggs, more preferably by methods of culturing diapausing eggs at 18° C. to induce adults hatched from the diapausing eggs to oviposit nondiapausing eggs, or by methods of rearing larvae hatched from diapausing eggs under continuous light to induce the reared adults to oviposit nondiapausing eggs, and most preferably by methods of culturing diapausing eggs at 25° C. and rearing larvae hatched from the diapausing eggs under continuous light to induce the reared adults to oviposit nondiapausing eggs.

The eggs can be cultured in an incubator at 18° C. to 25° C. or in a constant temperature room. Larvae can be reared on an artificial diet in a breeding room at 20° C. to 29° C.

The diapausing eggs of the present invention as described above can be cultured according to methods for culturing silkworm eggs common to those skilled in the art. For example, culturing can be performed using the method described in "Monbusho (Ministry of Education) (1978) Sanshu Seizo (Production of silkworm varieties) p. 193, Jikkyo Shuppan, Tokyo." The silkworm larvae of the present invention can be reared by methods well known to those skilled in the art. For example, silkworm larvae are reared according to the method described in "Monbusho (Ministry of Education) (1978) Sanshu Seizo (Production of silkworm varieties) p. 193, Jikkyo Shuppan, Tokyo."

In the present invention, whether oviposited eggs are nondiapausing eggs can be determined from the color of the eggs. It is generally known that diapausing eggs are dark brown in color and nondiapausing eggs are pale yellow. Therefore, in the present invention, oviposited eggs are determined to be nondiapausing eggs if the color is not dark brown, and preferably if the color is pale yellow.

Herein below, examples of methods for introducing DNAs into silkworm eggs will be specifically described, but methods of the present invention for introducing DNAs into silkworm eggs are not limited thereto. For example, DNAs can be introduced directly into silkworm eggs using a DNA injection tube. In a preferred embodiment, a hole is made physically or chemically in an eggshell in advance, and then DNAs are introduced through this hole. In this case, a DNA injection tube can be inserted into the egg through the hole by adjusting the insertion angle to be nearly perpendicular to the ventral surface of the egg.

In the present invention, examples of the methods for physically making a hole in an eggshell include hole making methods that use needles, microlasers or such. Preferably, a hole can be made in an eggshell by methods using needles. The material, strength and such of the needles are not particularly limited, as long as the needles can make a hole in a silkworm eggshell. The needles in the present invention ordinarily refer to rod-shaped needles having a sharp tip, but are not limited to this form. As long as the needles can make a hole in an eggshell, there are no particular limitations on their overall shape. For example, a pyramid-shaped object with a sharp tip, and a cone-shaped object with a sharp tip are also included in the "needles" of this invention. In the present invention, tungsten needles can be preferably used. The needles of the present invention have enough thickness (diameter) to make holes that allow a capillary, as described below, to pass through. The needle thickness is generally 2 to 20 μm, and preferably 5 to 10 μm. On the other hand, examples of methods for chemically making a hole in an eggshell include hole making methods that use chemical agents (for example, hypochlorous acid) or such.

In the present invention, the position of the hole is not particularly limited as long as a DNA injection tube can be inserted through the hole at an insertion angle that is nearly perpendicular to the ventral surface of the egg. The ventral side and its opposite side of the egg are preferable; the ventral side is more preferable; and the central portion of the ventral side slightly towards the posterior end is even more preferable.

In the present invention, the phrase "nearly perpendicular" means 70° to 120°, and preferably 80° to 90°. In the present invention, the phrase "position where germ cells will be developed in the future" usually refers to a position close to the egg surface at the ventral side of the egg (normally 0.01 mm to 0.05 mm beneath the egg surface), and preferably a position near the egg surface at the center of the ventral side of the egg, slightly towards the posterior pole.

In the present invention, the material, strength, internal diameter and such of tubes for injecting DNAs are not particularly limited. However, when a hole is made physically or chemically in an eggshell before insertion of a DNA injection tube, the tube preferably has enough thickness (external diameter) to pass through the opened hole. In the present invention, examples of the DNA injection tube include a glass capillary.

In a preferred embodiment of the DNA introduction methods of the present invention, an all-in-one manipulator equipped with a DNA injection tube and a needle is used to perform the steps of: physically or chemically opening a hole in a silkworm egg; inserting the DNA injection tube through the hole into the egg at an insertion angle nearly perpendicular to the ventral surface of the egg; and injecting DNAs. The present invention is preferably carried out using an apparatus comprising the manipulator as one of the components.

Such an apparatus consists of a dissecting microscope, an illuminator, a movable stage, a coarse manipulator fixed to the microscope with a metal fitting, a micromanipulator attached to this manipulator, and an injector that adjusts the air pressure for DNA injection. The pressure applied by the injector is provided from a nitrogen tank, and a pressure switch can be operated using a foot switch. Injection is performed on eggs immobilized onto a substrate such as a glass slide and the position of the eggs is adjusted using a movable stage. The glass capillary of the micromanipulator is connected to and operated by an operating portion connected to four tubes. Specifically, the position of a tungsten needle relative to an egg is adjusted using the coarse manipulator, and then a hole is made by shifting the egg in the horizontal direction using the stage lever. Next, the lever of the micromanipulator operating portion guides the tip of the glass capillary to the position of the hole, and the capillary is inserted into the egg using the stage lever. In this case, the glass capillary must be inserted perpendicularly to the ventral surface of the egg. The foot switch is then operated to inject DNAs, and the lever is operated to draw out the capillary from the egg. The opened hole is closed using instant adhesive or such, and the egg is protected in an incubator at constant temperature and constant humidity. The apparatus used in the present invention is preferably the apparatus described in U.S. Pat. No. 1,654,050, or a modified version of this apparatus.

Furthermore, in an embodiment of the present invention, silkworm eggs to which DNAs are introduced are preferably immobilized onto a substrate. Examples of the substrate used in the present invention include a glass slide and plastic sheet, but are not particularly limited thereto. In this embodiment of the present invention, the eggs are immobilized preferably after their direction is properly arranged, so that the DNAs can be injected precisely to the position in the silkworm egg where germ cells will be developed in the future. Furthermore, in this embodiment, the number of silkworm eggs immobilized onto the substrate is not particularly limited. When multiple silkworm eggs are used, it is preferable that the silkworm eggs are unidirectionally immobilized onto the substrate in a dorsoventral direction. The immobilization of silkworm eggs to a substrate in the present invention can be performed, for example, by inducing oviposition on commercially available cards (various egg cards) precoated with water-soluble glue, detaching eggs by adding water to the cards, and aligning the wet eggs on a substrate to be air-dried. The eggs are preferably immobilized onto a glass slide so that the eggs are arranged unidirectionally. Immobilization of the eggs onto the substrate can be also accomplished by using a double-sided adhesive tape, adhesive or such.

To confirm whether DNAs have been successfully introduced into silkworm eggs, for example, a method for re-extracting and analyzing the injected DNAs from the eggs (Nagaraju, J., Kanda, T., Yukuhiro, K., Chavancy, G, Tamura, T. and Couble, P. (1996) Attempt of transgenesis of the silkworm (*Bombyx mori* L) by egg-injection of foreign DNA. Appl. Entomol. Zool., 31, 589-598), or a method for observing expression of the injected DNAs in the eggs (Tamura, T., Kanda, T., Takiya, S., Okano, K. and Maekawa, H. (1990) Transient expression of chimeric CAT genes injected into early embryos of the domesticated silkworm, *Bombyx mori*. Jpn. J. Genet., 65, 401-410) can be used.

Furthermore, pharmaceutical compositions can be prepared by combining pharmaceutically acceptable carriers with the recombinant antibodies recovered by the methods of the present invention. Examples of the carriers include surfactants, excipients, coloring agents, flavoring agents, preservatives, stabilizers, buffers, suspending agents, isotonizing agents, binding agents, disintegrators, lubricants, fluidizing agents, and corrigents, but are not limited thereto. Other conventional carriers can be also used appropriately. Specifically, light anhydrous silicic acid, lactose, crystalline cellulose, mannitol, starch, calcium carmellose, sodium carmellose, hydroxypropylcellulose, hydroxypropylmethylcellulose, polyvinylacetal diethylaminoacetate, polyvinylpyrrolidone, gelatin, middle-chain fatty acid triglyceride, polyoxyethylene hydrogenated castor oil 60, sucrose, carboxymethylcellulose, corn starch, inorganic salts and such can be used.

In another specific embodiment of methods for producing recombinant antibodies of the present invention, recombinant antibodies are produced in the silkworm fat body. More specifically, the present invention relates to methods for producing a recombinant antibody comprising the steps (a) and (b) described below:

(a) producing a transgenic silkworm which comprises a promoter of a cytoplasmic actin protein-encoding DNA and a DNA encoding a recombinant antibody whose expression is regulated directly or indirectly by the promoter, and which secretes the recombinant antibody into the fat body; and (b) recovering the recombinant antibody from the produced transgenic silkworm.

The present invention also relates to methods for producing a recombinant antibody comprising the steps (a) and (b) described below:

(a) producing a transgenic silkworm which comprises a promoter of a cytoplasmic actin protein-encoding DNA and a DNA encoding a recombinant antibody that comprise a signal sequence and whose expression is regulated directly or indirectly by the promoter, and which secretes the recombinant antibody into the fat body; and (b) recovering the recombinant antibody from the produced transgenic silkworm.

In the step of producing transgenic silkworms of the present invention, first, silkworm eggs are produced to comprise a promoter of a cytoplasmic actin protein-encoding DNA and a DNA encoding a recombinant antibody whose expression is regulated directly or indirectly by the promoter. Next, from the silkworms hatched from the produced silkworm eggs, transgenic silkworms that secrete the recombinant antibody into the fat body are selected. Selection of transgenic silkworms can be performed by the above-mentioned methods.

In the present invention, silkworm eggs comprising a promoter of a cytoplasmic actin protein-encoding DNA and a DNA encoding a recombinant antibody whose expression is regulated directly by the promoter are, for example, silkworm eggs comprising a DNA in which a DNA encoding a recombinant antibody is operably linked downstream of a promoter of a cytoplasmic actin protein-encoding DNA. Such silkworm eggs can be produced by introducing a DNA in which a DNA encoding a recombinant antibody is operably linked downstream of a promoter of a cytoplasmic actin protein-encoding DNA into silkworm eggs.

Furthermore, in the present invention, silkworm eggs which comprise a promoter of a cytoplasmic actin protein-encoding DNA and a DNA encoding a recombinant antibody protein whose expression is regulated directly by the promoter are, for example, silkworm eggs comprising (i) a DNA in which a DNA encoding a transcriptional regulator is operably linked downstream of a promoter of a cytoplasmic actin protein-encoding DNA, and (ii) a DNA in which a recombinant antibody-encoding DNA is operably linked downstream of a target promoter of the transcriptional regulator. The phrase "operably linked" is defined as described above. Examples of combinations of transcriptional regulator and target sequence include those described above.

Silkworm eggs can be produced by the above-mentioned methods. For example, the DNAs of (i) and (ii) described above are introduced into separate silkworm eggs. Silkworm eggs carrying both DNAs can be obtained by crossing transgenic silkworms hatched from silkworm eggs into which the respective DNAs have been introduced. Alternatively, silkworm eggs comprising the DNAs of (i) and (ii) can be obtained by artificially introducing one of the DNAs into eggs laid by transgenic silkworms introduced with the other DNA. Furthermore, silkworm eggs carrying the DNAs of (i) and (ii) can be obtained by introducing both DNAs into the same eggs.

DNAs can also be introduced into silkworm eggs by the above-described methods. Furthermore, when producing recombinant antibodies in the silkworm fat body, baculovirus vectors can also be used to produce transgenic silkworms (Yamao, M., N. Katayama, H. Nakazawa, M. Yamakawa, Y. Hayashi et al., 1999, Genes Dev. 13: 511-516).

Examples of a promoter of a cytoplasmic actin protein-encoding DNA described above include DNAs comprising the nucleotide sequence of SEQ ID NO: 19. Examples of DNAs comprising the nucleotide sequence of SEQ ID NO: 19 include the DNA consisting of the nucleotide sequence of SEQ ID NO: 19, and DNAs that comprise an upstream region or downstream region of the DNA consisting of the nucleotide sequence of SEQ ID NO: 19, but are not limited thereto.

Furthermore, in the present invention, a promoter of a cytoplasmic actin protein-encoding DNA is, for example, a DNA which is structurally similar to a DNA comprising the nucleotide sequence of SEQ ID NO: 19 and has a promoter activity equivalent to or improved compared to a DNA comprising the nucleotide sequence of SEQ ID NO: 19. Such promoters can be prepared by the methods described above. The upstream region and downstream region of the DNAs consisting of the nucleotide sequence of SEQ ID NO: 19 are disclosed in MANGE, A., E. JULIEN, J. C. PRUDHOMME and P. COUBLE, 1997 A strong inhibitory element down-regulates SRE-stimulated transcription of the A3 cytoplasmic actin gene of Bombyx mori. J. Mol. Biol. 265: 266-274.

The combinations of transcriptional regulator and target sequence described above can be used. A specific embodiment and method for producing a transgenic silkworm whose genome has been inserted with a gene prepared by linking the GAL4 gene downstream of the promoter of a cytoplasmic actin-encoding DNA are disclosed in IMAMURA, M., J. NAKAI, S. INOUE, G. X. QUAN, T. KANDA et al., 2003 Targeted gene expression using the GAL4/UAS system in the silkworm Bombyx mori. Genetics 165: 1329-1340.

In the present invention, a DNA encoding a recombinant antibody whose expression is regulated directly or indirectly by the promoter of a cytoplasmic actin protein-encoding DNA preferably comprises a signal sequence. Specific embodiments of the signal sequence are those described above.

Recombinant antibodies produced by the above-mentioned methods can be recovered, for example, from the fat body. Recombinant antibodies can be recovered from the fat body by methods known to those skilled in the art, for example, by removing the fat body from a larval body; and homogenizing it in a buffer for protein extraction, or inducing secretion of proteins from the fat body into the body fluid and then fractionating the body fluid.

Antibodies produced by the methods of the present invention are not particularly limited so long as they are produced by the methods of the present invention, and they may or may not comprise a signal sequence. More specifically, antibodies produced by the antibody production methods of the present invention include both antibodies comprising a signal sequence and antibodies without a signal sequence.

The present invention also relates to recombinant antibody-encoding DNAs. The present invention more preferably relates to DNAs encoding recombinant antibodies comprising a signal sequence. More specifically, the present invention relates to DNAs encoding scFv antibodies comprising a human acid phosphatase. For example, such DNAs include the DNA of SEQ ID NO: 13 or 14. Another example includes DNAs that hybridize under stringent conditions with DNAs comprising the nucleotide sequence of SEQ ID NO: 13 or 14, and encode proteins functionally equivalent to proteins comprising the amino acid sequence of SEQ ID NO: 15.

The present invention further relates to DNAs encoding antibodies which comprise an L chain comprising a mouse immunoglobulin L chain κ signal sequence and an H chain comprising a mouse IgG1 signal sequence. An example of a DNA encoding an L chain comprising a mouse immunoglobulin L chain κ signal sequence is the DNA of SEQ ID NO: 48. A further example is a DNA that hybridizes under stringent conditions with a DNA comprising the nucleotide sequence of SEQ ID NO: 48, and encodes a protein functionally equivalent to a protein comprising the amino acid sequence of SEQ ID NO: 48. Meanwhile, an example of a DNA encoding an H chain comprising a mouse IgG1 signal sequence is the DNA of SEQ ID NO: 50. A further example is a DNA that hybridizes under stringent conditions with a DNA comprising the nucleotide sequence of SEQ ID NO: 50, and encodes a protein functionally equivalent to a protein comprising the amino acid sequence of SEQ ID NO: 50.

The present invention provides vectors and transformed cells comprising recombinant antibody-encoding DNAs. The present invention also provides vectors and transformed cells comprising DNAs that encode recombinant antibodies comprising a signal sequence. The vectors used in the present invention include, for example, M13 vectors, pUC vectors, pBR322, pBluescript, and pCR-Script, but are not limited thereto. In addition to the above vectors, for example, pGEM-T, pDIRECT, and pT7 can also be used for the subcloning and excision of cDNAs. When using vectors to produce the antibodies of the present invention, expression vectors are particularly useful. When *E. coli* such as JM109, DH5α, HB101, or XL1-Blue are used as the host cell, the vector should have, in addition to the above characteristics in order to be amplified in *E. coli*., a promoter such as a lacZ promoter (Ward et al. (1989) Nature 341: 544-546; (1992) FASEB J. 6: 2422-2427), araB promoter (Better et al. (1988) Science 240: 1041-1043), or T7 promoter, to allow efficient expression of the desired gene in *E. coli*. Other examples of the vectors include pGEX-5X-1 (Pharmacia), "QIAexpress system" (QIAGEN), pEGFP, and pET.

Furthermore, the vector preferably comprises a signal sequence for polypeptide secretion. When producing polypeptides into the periplasm of *E. coli*, the pelB signal sequence (Lei, S. P. et al. J. Bacteriol. 169: 4379 (1987)) may be used as a signal sequence for polypeptide secretion. For example, calcium chloride methods or electroporation methods may be used to introduce the vector into a host cell.

In addition to *E. coli*, expression vectors derived from mammals (e.g., pCDNA3 (Invitrogen), pEGF-BOS (Nucleic Acids Res. (1990) 18(17), p. 5322), pEF, pCDM8), insect cells (e.g., "Bac-to-BAC baculovirus expression system" (GIBCO-BRL), pBacPAK8), plants (e.g., pMH1, pMH2), animal viruses (e.g., pHSV, pMV, pAdexLcw), retroviruses (e.g., pZIPneo), yeasts (e.g., "*Pichia* Expression Kit" (Invitrogen), pNV11, SP-Q01), and *Bacillus subtilis* (e.g., pPL608, pKTH50) may also be used as vectors for producing the antibodies of the present invention.

For expression in animal cells such as CHO, COS, and NIH3T3 cells, the vector is required to have a promoter necessary for expression in such cells, for example, an SV40 promoter (Mulligan et al. (1979) Nature 277: 108), MMLV-LTR promoter, EF1α promoter (Mizushima et al. (1990) Nucleic Acids Res. 18: 5322), and CMV promoter. It is more preferable that the vector also carries a gene for selecting transformants (for example, a drug-resistance gene enabling selection by a drug such as neomycin and G418). Examples of vectors with such characteristics include pMAM, pDR2, pBK-RSV, pBK-CMV, pOPRSV, and pOP13.

Recombinant antibody-encoding DNAs can be introduced into cells by those skilled in the art using known methods such as the electroporation method.

Furthermore, the present invention relates to transgenic silkworms which comprise recombinant antibody-encoding DNAs and secrete recombinant antibodies. More specifically, the present invention relates to transgenic silkworms which comprise a promoter of a DNA encoding a protein specifically expressed in the silk gland and a DNA encoding a recombinant antibody whose expression is regulated directly or indirectly by the promoter, and which secrete the recombinant antibody into the silk gland. In addition, the present invention provides transgenic silkworms which comprise (i) a DNA encoding a transcriptional regulator operably linked downstream of a promoter of a DNA encoding a protein specifically expressed in the silk gland, and (ii) a recombinant antibody-encoding DNA operably linked downstream of a target promoter of the transcriptional regulator; and transgenic silkworms comprising a DNA in which a recombinant antibody-encoding DNA is operably linked downstream of a promoter of a DNA encoding a protein specifically expressed in the silk gland.

In the present invention, DNAs encoding recombinant antibodies whose expression is regulated directly or indirectly by a promoter of a DNA encoding a protein specifically expressed in the silk gland preferably comprise signal sequences for promoting antibody secretion and increasing the amount of recovered antibodies. Specific embodiments of the signal sequence are those described above.

Furthermore, the present invention relates to transgenic silkworms which comprise a promoter of a cytoplasmic actin protein-encoding DNA and a DNA encoding a recombinant antibody whose expression is regulated directly or indirectly by the promoter, and which secrete the recombinant antibody into the fat body. More specifically, the present invention provides transgenic silkworms comprising (i) a DNA encoding a transcriptional regulator operably linked downstream of a promoter of a cytoplasmic actin protein-encoding DNA, and (ii) a recombinant antibody-encoding DNA operably linked downstream of a target promoter of the transcriptional regulator; and transgenic silkworms comprising a DNA in which a recombinant antibody-encoding DNA is operably linked downstream of a promoter of a cytoplasmic actin protein-encoding DNA.

In the present invention, DNAs encoding recombinant antibodies whose expression is regulated directly or indirectly by a promoter of a cytoplasmic actin protein-encoding DNA preferably comprises a signal sequence for promoting antibody secretion and increasing the amount of recovered antibodies. Specific embodiments of the signal sequence are those described above.

These transgenic silkworms can be produced by the methods described above. Furthermore, there are no particular limitations on the form of the transgenic silkworms of the present invention, and for example, they may be in the form of eggs. Large amounts of desired recombinant antibodies can be produced by using the transgenic silkworms of the present invention.

The present invention also provides transgenic silkworms comprising a recombinant antibody-encoding DNA operably linked downstream of a target promoter of a transcriptional regulator. Examples of transcriptional regulators and target promoters are those mentioned above. Such silkworms can be used to produce transgenic silkworms carrying the DNAs of (i) and (ii) described above, and to produce eggs for these silkworms.

In the present invention, DNAs encoding recombinant antibodies whose expression is regulated directly or indirectly by a promoter of a DNA encoding a protein specifically expressed in the silk gland preferably comprise a signal sequence for promoting antibody secretion and increasing the amount of recovered antibodies. Specific embodiments of the signal sequence are those described above.

Furthermore, the present invention provides cocoons spun by the transgenic silkworms of the present invention. Such cocoons are useful as cocoons that contain large amounts of desired recombinant antibodies. The present invention also provides silk threads produced from the cocoons and which contain a recombinant antibody. Silk fabrics containing the silk threads of the present invention, for example, silk fabrics containing recombinant antibodies, can be produced by known methods. The present invention also provides such silk fabrics.

The present invention provides DNAs to be used in the methods of the present invention. Such DNAs include (a) a DNA encoding a transcriptional regulator operably linked downstream of a promoter of a DNA encoding sericin or fibroin, (b) a DNA encoding a recombinant antibody operably linked downstream of a target promoter of the transcriptional regulator, and (c) a DNA in which a recombinant antibody-encoding DNA is operably linked downstream of a promoter of a DNA encoding sericin or fibroin; and kits containing combinations of these DNAs can be provided. The present invention also provides vectors in which the DNAs of (a) to (c) are inserted between the inverted terminal repeats of transposons. Furthermore, the present invention provides kits containing the vectors and vectors comprising transposase-encoding DNAs (helper vectors).

Recombinant antibody-encoding DNAs operably linked downstream of a target promoter of a transcriptional regulator, and DNAs in which a recombinant antibody-encoding DNA is operably linked downstream of a promoter of a sericin- or fibroin-encoding DNA, preferably comprise a signal sequence for promoting antibody secretion and increasing the amount of recovered antibodies. Specific embodiments of the signal sequence are those described above.

Furthermore, the present invention relates to diagnostic agents for diabetic nephropathy and reagents for evaluating nutritional status, which comprise as an active ingredient a recombinant anti-transferrin antibody obtained by the antibody production methods of the present invention. The recombinant anti-transferrin antibodies obtained by the antibody production methods of the present invention include both antibodies comprising a signal sequence and antibodies without a signal sequence. When a signal sequence is used, preferred examples are those described above.

The anti-transferrin antibodies of the present invention also include both whole antibodies and low-molecular-weight antibodies. Specific examples of the whole antibodies include antibodies which comprise L chains comprising the amino acid sequence of any one of SEQ ID NOs: 3, 21, and 29 as a signal sequence, the amino acid sequence of SEQ ID NO: 23 as an L chain variable region, the amino acid sequence of SEQ ID NO: 25 as a Jκ segment, and the amino acid sequence of SEQ ID NO: 27 as a κ chain constant region; and H chains comprising the amino acid sequence of any one of SEQ ID NOs: 3, 21, and 29 as a signal sequence, the amino acid sequence of SEQ ID NO: 31 as an H chain variable region, the amino acid sequence of SEQ ID NO: 33 as CH1, the amino acid sequence of SEQ ID NO: 35 as a hinge region, the amino acid sequence of SEQ ID NO: 37 as CH2, and the amino acid sequence of SEQ ID NO: 39 as CH3. More specific examples include antibodies that comprise L chains comprising the amino acid sequence of SEQ ID NO: 49 and H chains comprising the amino acid sequence of SEQ ID NO: 51.

On the other hand, specific examples of the low-molecular weight antibodies include Fab, Fab', F(ab')2, Fv, scFv (single chain Fv), diabody, and sc(Fv)2 (single chain (Fv)2) as described above. Low-molecular-weight antibodies that are particularly preferred in the present invention are scFv antibodies. In an scFv antibody, a signal sequence, VL, linker, and VH are preferably arranged in this order from the N terminus of the single chain polypeptide. Specific embodiments of a VL, linker, and VH are shown in SEQ ID NOs: 6, 9, and 12, respectively. Therefore, a particularly preferred anti-transferrin antibody in the present invention is an scFv antibody which comprises a human acid phosphatase signal sequence comprising the amino acid sequence of SEQ ID NO: 15.

Furthermore, the present invention relates to methods for measuring the amount of transferrin in biological samples obtained from subjects. Transferrin is a protein of molecular weight 79,000 present in the blood, urine and such, and it is an important indicator of iron metabolism and hematopoiesis. The amount of transferrin in living bodies reflects diseases of the digestive organs, kidney and such, and pathophysiological states of tumors, inflammation and such; therefore, these diseases can be diagnosed by measuring the amount of transferrin.

In methods of the present invention for measuring transferrin in a biological sample, first, a biological sample is obtained from a subject whose transferrin quantity is to be measured. Then, the biological sample is contacted with an anti-transferrin antibody of the present invention. Biological samples used in the measurement methods of the present invention are not particularly limited, but examples include blood (serum) and urine. Preferred embodiments of antibodies in the measurement methods of the present invention are described above. In measurements of the present invention, next, binding of the antibody to transferrin in the biological sample is detected. Binding of the antibody to transferrin can be detected by methods well known to those skilled in the art, including, without limitation, ELISA and EIA. Measurement methods of the present invention are methods that measure the amount of transferrin in a biological sample by detecting the binding of antibody to transferrin in the sample. That is, if the binding of antibody to transferrin is not detected at all, transferrin is judged to be absent in the biological sample. On the contrary, if the binding of antibody to transferrin is detected, transferrin is judged to be present in the biological sample. Those skilled in the art can determine the amount of transferrin in a biological sample according to the detected level of antibody binding to transferrin. Accordingly, measurement of the amount of transferrin in the present invention includes not only determination of the presence or absence of transferrin in a biological sample, but also quantification of the amount of transferrin in a biological sample according to the level of binding.

The present invention further relates to methods for diagnosing diabetic nephropathy. In the diagnostic methods of the present invention, first, the amount of transferrin in a biological sample is measured according to the above-described methods for measuring the amount of transferrin. Next, the measured amount of transferrin is compared to that in biological samples derived from subjects who clearly are not affected by diabetic nephropathy. When the measured amount of transferrin is greater than that in a normal control, a subject who has provided the biological sample is judged to be affected by or have a high risk of diabetic neuropathy in the future.

In the methods of the present invention for diagnosing diabetic nephropathy, the measured amount of transferrin can be compared to that in biological samples derived from subjects clearly affected by diabetic nephropathy. As a result of the comparison, if the amount of transferrin is comparable to that in the biological samples from subjects clearly affected by diabetic nephropathy, subjects who have provided the biological samples are judged to be affected by diabetic nephropathy. The phrase "comparable to" includes not only cases in which the amount of transferrin is exactly the same, but also cases in which the amount is substantially the same. Whether the amount is substantially the same can be determined appropriately by those skilled in the art according to the medical condition and other characteristics of the subject. Examples of references describing standards for such determinations include:

Yamaguchi, T.: Nippon Rinsho, 53 (supplementary issue), 227-229 (1995);

Ando, Y: Horumon to Rinsho (Clinical Endocrinology), 42 (6), 91-95 (1994);

Konno, M: Igaku to Yakugaku, 32 (3), 555-565 (1994);

Ishibashi, F.: Tonyobyo (Diabetes) 35 (12), 949-954 (1992);

Aoki, Y.: Rinsho Yakuri Review (Reviews in Clinical Pharmacology) special issue No. 127, 12-16, (2003, 10);

Sakurabayashi, I. and Yamada, T.: Gekkan (Monthly) Medical Technology, Supplement, Rinsho Kensako Jiten (Dictionary of Clinical Examination Items), (2003); and Higashi, T. and Goto, H.: Medical Technology, Vol. 30, 906-911, No. 8 (2002.8).

A method of the present invention for diagnosing diabetic nephropathy can be used by itself, or as a supplementary method used in combination with various other methods for diagnosing diabetic nephropathy. Use of such a method in combination with various other methods for diagnosing diabetic nephropathy enables more accurate and effective diagnosis of diabetic nephropathy. Accordingly, observation made using methods of the present invention for diagnosing diabetic nephropathy are preferably used comprehensively with various clinical findings characteristic of diabetic nephropathy patients.

The present invention also relates to methods for evaluating the nutritional status of a subject. In the methods of the present invention for evaluating nutritional status, subjects are judged to be affected by or have a high risk of malnutrition when the amount of transferrin is less than that in a normal control. In the present invention, the greater the degree of decrease in the transferring quantity, the higher the risk of malnutrition the subject is judged to have, or the more severe of the malnutrition by which the subject is judged to be affected. Those skilled in the art can determine the risk of malnutrition or the degree of malnutrition of a subject from the degree of decrease in the transferring quantity. For example, when transferrin is not detected at all or not substantially detected in a subject, the subject is judged to be affected by severe malnutrition.

In the methods of the present invention for evaluating nutritional status, first, the amount of transferrin in a biological sample is measured. Next, the amount of measured transferrin is compared to that of a normal control. Measurement of the amount of transferrin in a biological sample can be carried out according to the methods described above. Whether a subject has a high risk of malnutrition or is affected by malnutrition can also be judged according to standards ordinarily adopted by those skilled in the art as described above.

The methods of the present invention for evaluating nutritional status can be used in combination with clinical examinations, physical measurements, diet survey and such to comprehensively evaluate and judge nutritional status of an individual or a specific group of individuals (nutrition assessment ("Rinsho Eiyo (Clinical Nutrition)" extra edition, volume 99, No. 5, "Jissen Eiyo Assessment (Practical Nutrition Assessment)"). In the methods of the present invention for evaluating nutritional status, a subject may be any individual or any group of individuals. By conducting the present invention's methods for evaluating nutritional status, the nutritional status of an individual or a group of individuals can be measured. As described above, those skilled in the art can determine from the measurement results the presence or absence of malnutrition or the degree of malnutrition in a subject. In the present invention, the term "malnutrition" refers to a condition in which a specific or various types of nutrients are deficient or excessive, or a condition in which the balance of nutrients is disrupted.

As an embodiment of the present invention's methods for evaluating nutritional status, for example, the methods of the present invention for evaluating nutritional status can be performed on hospitalized subjects. For example, when the measured value of transferrin in a sample derived from a subject who is hospitalized is decreased compared to that in the same subject under normal healthy conditions (a certain range of fluctuations is considered if present), the subject can be judged to have a high risk of malnutrition or to be affected by malnutrition.

There is no possibility that recombinant antibody extracts of the antibodies produced by the production methods of the present invention contain antibodies other than desired antibodies. Therefore, a cross reaction is unlikely to occur, and only antibodies that react with antigens of interest can be accurately measured. Accordingly, the amount of transferrin can be measured accurately in the present invention's methods of measuring the transferrin quantity in biological samples for diagnosing diabetic nephropathy and evaluating nutritional status.

All prior art references cited herein are incorporated herein by reference.

EXAMPLES

Herein below, the present invention will be specifically described with reference to Examples, but it is not to be construed as being limited thereto.

Example 1

Materials and Methods

1. Construction of a Plasmid Vector

In this study, the plasmid vector pUASFvaTf (FIG. 1) was prepared to produce an scFv antibody from a mouse anti-human transferrin antibody that reacts with human transferrin (anti-transferrin scFv antibody: hereinafter referred to as aTf) using transgenic silkworms. This vector for production of transgenic silkworms was prepared by inserting between inverted terminal repeats of the piggyBac transposon, the antibody protein gene FvaTf fused to the promoter UAS which promotes gene expression in the presence of the yeast transcriptional regulator GAL4.

The scFv anti-human transferrin antibody was designed as follows. A DNA was designed to have a structure in which an antibody H chain variable region (VH), a flexible linker peptide (Linker), and an antibody L chain variable region (VL) are linked downstream of a human acid phosphatase secretory signal sequence in this order. Known sequences were used for the amino acid sequences of VH-Linker-VL including the connection between the genes. Nucleotide sequences of the scFv antibody genes used in this experiment (before and after codon conversion), and the relation between SEQ ID NOs and the amino acid sequences produced from the nucleotide sequences are shown in Table 2. Gene codons were converted to codons suitable for expression in insects (pUC57/FvaTf).

TABLE 2

|  | Nucleotide sequence (before codon conversion) | Nucleotide sequence (after codon conversion) | Amino acid sequence |
|---|---|---|---|
| Signal sequence | SEQ ID NO: 1 | SEQ ID NO: 2 | SEQ ID NO: 3 |
| H chain variable region (VH) | SEQ ID NO: 4 | SEQ ID NO: 5 | SEQ ID NO: 6 |
| Linker | SEQ ID NO: 7 | SEQ ID NO: 8 | SEQ ID NO: 9 |
| L chain variable region (VL) | SEQ ID NO: 10 | SEQ ID NO: 11 | SEQ ID NO: 12 |
| Whole antibody | SEQ ID NO: 13 | SEQ ID NO: 14 | SEQ ID NO: 15 |

A gene plasmid was constructed with a GAL4/UAS system by the procedure indicated in FIG. 1. More specifically, a FvaTf fragment was obtained by digesting pUC57/FvaTf with the restriction enzyme SpeI, and was inserted into the donor vector pBluescript II/UAS-SV40 which had been digested with the restriction enzyme Bln I (pBluescript II/UAS-FvaTf-SV40UTR).

Figure 2:
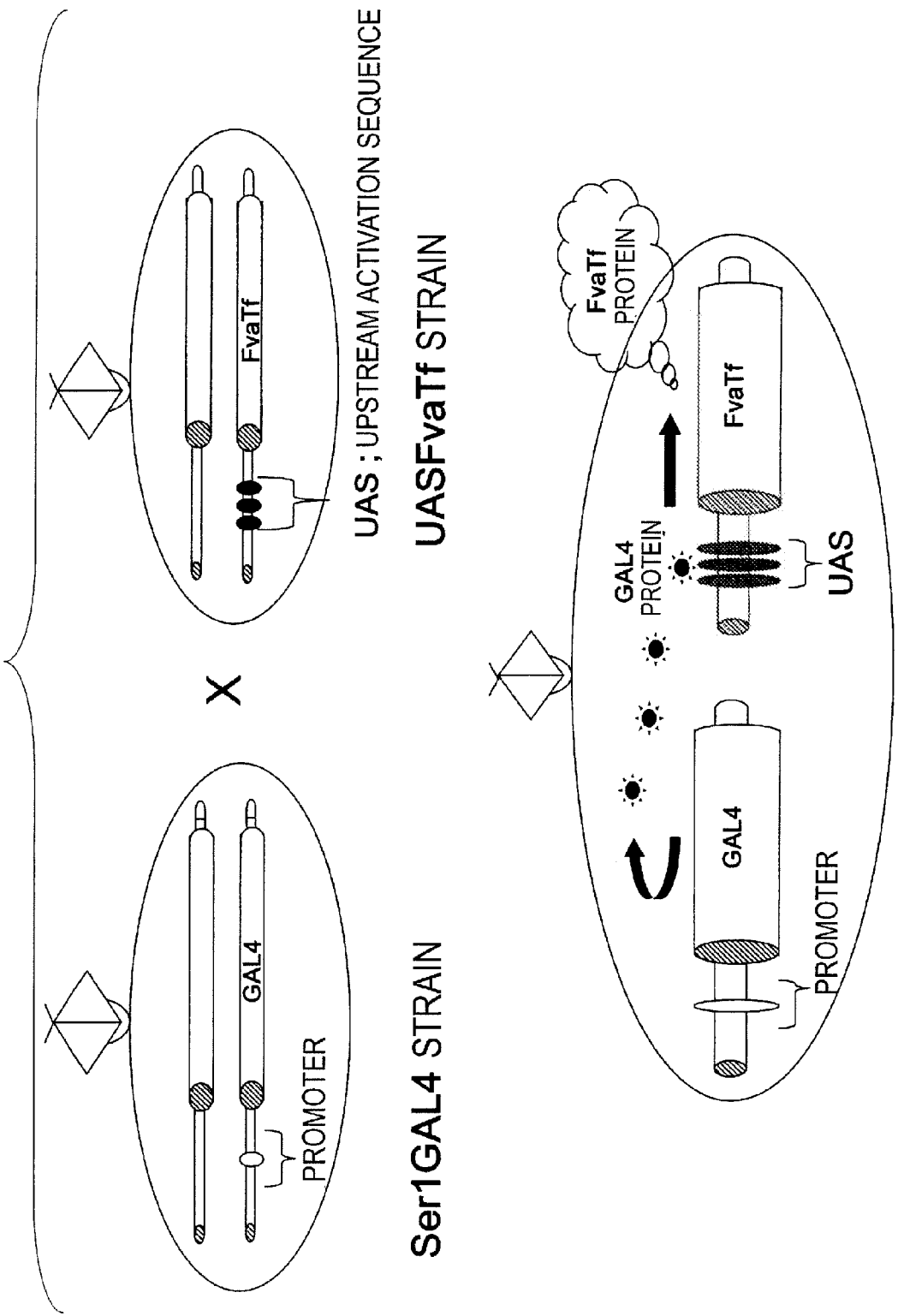
FIG. 2 shows a procedure for producing antibody-expressing silkworms by crossing the Ser1GAL4 strain with the UASFvaTf strain.

To express this gene at a target site, silkworms of the established Ser1GAL4/3XP3DsRed strain (Tamura, et al., 2004) were used. In these transgenic silkworms, it has been confirmed that the GAL4 gene is expressed only in the middle silk gland, and expression of an introduced gene is regulated by UAS (Tamura, et al., 2004). To express the introduced antibody gene, the obtained UASFvaTf strain carrying the antibody gene was crossed with the above-mentioned GAL4 strain (FIG. 2).

This plasmid vector carries, as a marker gene for identifying the transgenic silkworms, the green fluorescent protein gene 3XP3GFP which has a promoter that promotes expression in the ocellus of embryos, compound eyes of moths, and nerve-derived tissues (Horn, C., and E. A. Wimmer, (2000) Dev. Genes Evol. 210: 630-637; Murizio et al. (1994) Protein Science, 3: 1476-1484).

2. Western Blotting

Figure 3:
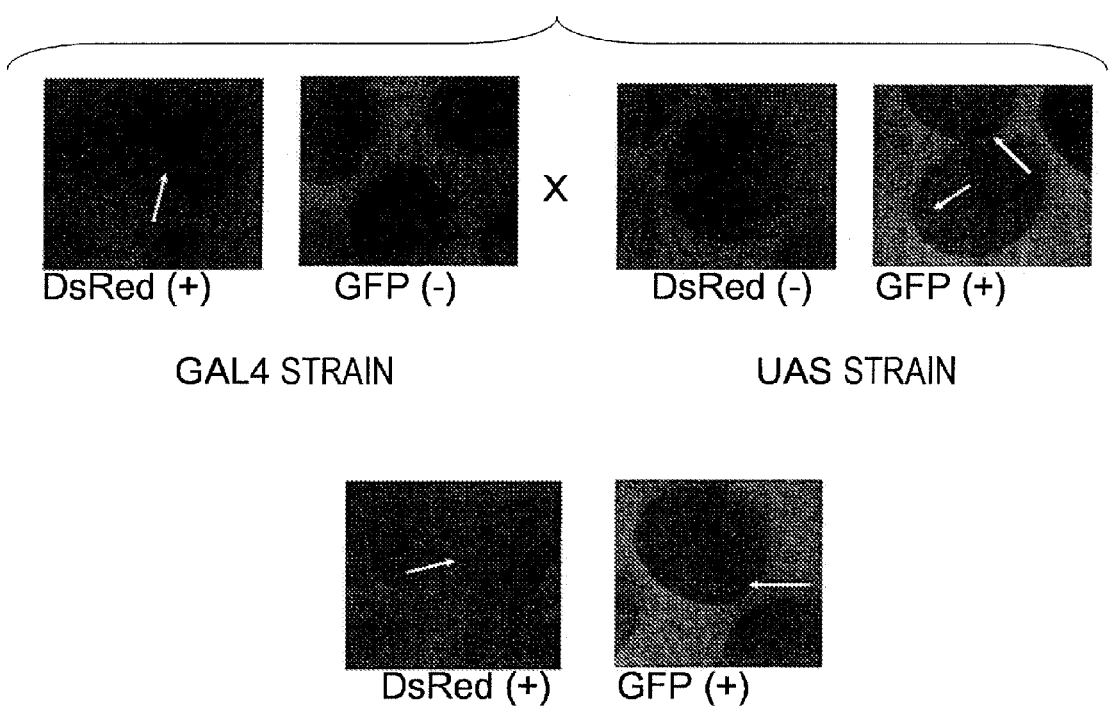
FIG. 3 shows fluorescence stereo micrographs of individuals carrying the GAL4 gene and individuals carrying UAS.

Western Blotting was performed as follows. Eggs of the next generation were obtained by crossing the Ser1GAL4/3XP3DsRed strain with the UASFvaTf strain, and they were observed 6 days after oviposition under a fluorescence steromicroscope to identify GAL4/UAS individuals (FIG. 3). Only individuals that have both genes were raised; the silk gland was removed from 5th instar silkworms on day 0, day 1, and day 2 of spinning; and proteins were extracted from the cell layer using 2% lithium dodecyl sulfate, 5 mM EDTA, and 50 mM Tris-HCl (pH 7.4). Similarly, as a negative control, the silk gland was removed on day 0 of spinning from 5th instar Ser1GAL4 strain silkworms which did not have UASFvaTf, and proteins were extracted. To two volumes of the extracted sample, one volume of SDS sample buffer (6% SDS, 24% glycerol, 12% 2-mercaptoethanol, and 0.1% BPB) was added, and after the mixture was subjected to SDS-PAGE using Super Sep 5-20% (Wako Pure Chemical Industries), Western blotting was performed as follows. After completion of SDS-PAGE, proteins were transferred onto a PVDF membrane (Millipore) by applying a 0.8 mA/cm$^2$ current for one hour, and then blocked using BlockAcd (Dainippon Pharmaceutical). The membrane was washed with PBS-T (0.05% Tween, 150 mM NaCl, 10 mM phosphate buffer, pH 7.4), and then shaken at room temperature for six hours in a solution of BlcokAce containing 100-fold dilution of a rabbit anti-mouse Ig-HRP-labeled antibody (Amersham Biosciences). After the rabbit anti-mouse Ig-HRP-labeled antibody reaction, the same washing procedure described above was carried out and a POD Immunostain Set (Wako Pure Chemical Industries) was used for detection.

3. RT-PCR

RT-PCR was performed as follows. As described above, individuals having both GAL4/UAS genes were raised, and the middle silk gland was removed from 5th instar silkworms on day 0, day 1, and day 2 of spinning. Similarly, as a negative control, the silk gland was removed on day 0 of spinning from 5th instar Ser1GAL4 strain silkworms which did not have UASFvaTf. Next, the removed middle silkglands were transferred to a glass homogenizer (WHEATON), and total RNAs were extracted using ISOGEN (Nippon Gene). The total RNAs were adjusted to 50 μg/20 μl with DPEC DEPC water, and then reverse transcribed into cDNAs using a First-strand cDNA Synthesis Kit (Amersham Biosciences) according to the attached document. PCR was performed as follow using the reverse transcription products as a template. 5 μl of 10×PCR buffer attached to KOD plus (TOYOBO), 150 μM each of primers (SEQ ID NO: 16 and SEQ ID NO: 17), 1 mM of MgSO$_4$, 0.2 mM of dNTPs, and 2 units of KOD plus were mixed, and the total volume was adjusted to 50 μl. PCR was carried out using an Eppendorf DNA thermal cycler with one cycle of 94° C., 2 minutes; 35 cycles of 94° C., 15 seconds, 62° C., 15 seconds, and 72° C., 30 seconds; and one cycle of 72° C., 1 minute for elongation reaction. The plasmid vector pUASFvaTf was used as a template in the positive PCR control.

4. Measurement of Recombinant Antibody Activity

Measurement of the activity of a recombinant antibody against an antigen by enzyme-linked immunosorbent assay (ELISA) was carried out by the following procedure. The middle silk gland was removed on day 0 of spinning from 5th instar silkworms of the Ser1GAL4/UASFvaTf strain and the Ser1GAL4 strain that did not have UASFvaTf, and 1 ml of Tris buffer (20 mM Tris-HCl, pH 7.4) was added per 200 mg of the removed tissue. This was homogenized using a glass homogenizer and centrifuged at 14,000 rpm for 20 minutes, and then the supernatant was diluted five times (40 mg/ml) and ten times (20 mg/ml) in Tris buffer. These samples and the undiluted sample (original concentration: 200 mg/ml) were used as samples for ELISA measurement. Furthermore, similar procedures were used to prepare samples of the Ser1GAL4 strain silkworms for ELISA measurement as a negative control. 100 μl of the samples for ELISA measurement thus prepared were dispensed into a microtiter plate (NUNC) presensitized with 100 μg/well of transferrin (Biogenesis), and the plate was shaken at room temperature for two hours. Next, the ELISA measurement samples were removed from the wells, and the wells were washed three times with 200 μl of PBS-T. Into each well, 100 μl of a solution prepared in advance by diluting a rabbit anti-mouse Ig-HRP-labeled antibody 100-fold with PBS (150 mM NaCl, 10 mM phosphate buffer, pH 7.4) was dispensed, and the plate was shaken at room temperature for six hours. The plate was washed and 100 μl of 3,3',5,5'-tetramethylbenzidine (Roche Japan) was added for color development. Exactly three minutes after addition of 3,3',5,5'-tetramethylbenzidine, 100 μl of 1 N sulfuric acid was dispensed to stop the color development. After that, the absorbance at 450 nm was measured using a model 550 microplate reader (BioRad).

Results and Discussion

The plasmid prepared by the method described above, and the helper plasmid pA3PIG encoding a transferase gene (Tamura et al., 2000) were injected together into approximately 1000 silkworm eggs at an early developmental stage, and GFP expression in the ocellus of embryos of the next generation was examined. As a result, as shown in Table 3, individuals expressing GFP were found in two moth broods.

TABLE 3

| Vector | n | Number of injected eggs | Number of moth eggs examined | Number of transgenic moth broods |
|---|---|---|---|---|
| pBac UAS USN | 1 | 960 | 98 | 2 |

As a result of raising these transgenic silkworms, only one strain could be successfully established. The obtained UAS-FvaTf/3XP3GFP strain was crossed with the Ser1GAL4/3XP3DsRed strain, and the segregation ratio of individuals carrying each of the fluorescent protein genes in the next generation is shown in Table 4.

TABLE 4

| | Marker | | | |
|---|---|---|---|---|
| | DsRed | GFP | DsRed/GFP | Negative |
| Number of positive individuals | 51 | 59 | 54 | 63 |
| Segregation ratio (%) | 22.4 | 25.9 | 23.7 | 27.7 |

Since these values match the theoretical values when individuals heterozygous for both genes are crossed with each other, the two genes were found to be inserted into different chromosomes and inherited independently. In this case, transgenic silkworms having either or both of the 3XP3GFP and 3XP3DsReD genes could be easily identified, since their ocellus and nerve-derived tissues showed fluorescence when observed under a fluorescence stereomicroscope during the embryonic stage as shown in FIG. 3.

Figure 5:
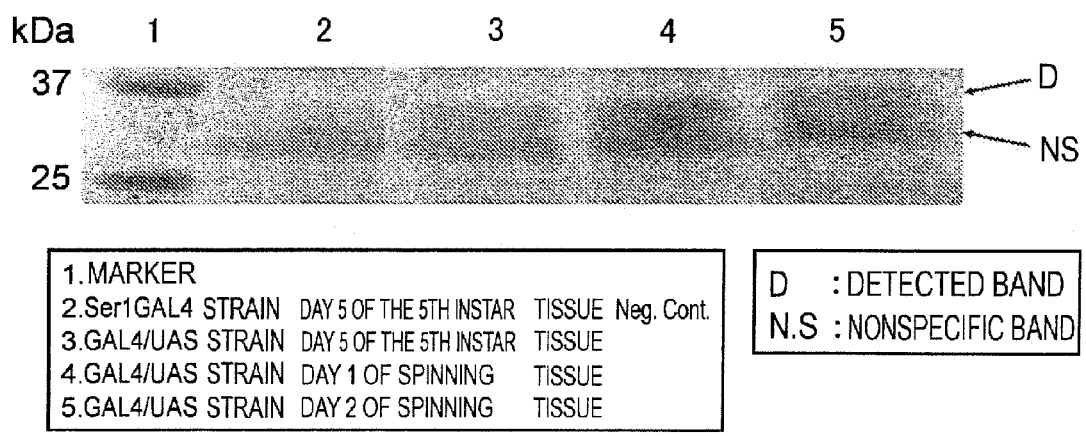
FIG. 5 is a photograph showing identification of the antibody protein by Western blotting.
Figure 6:
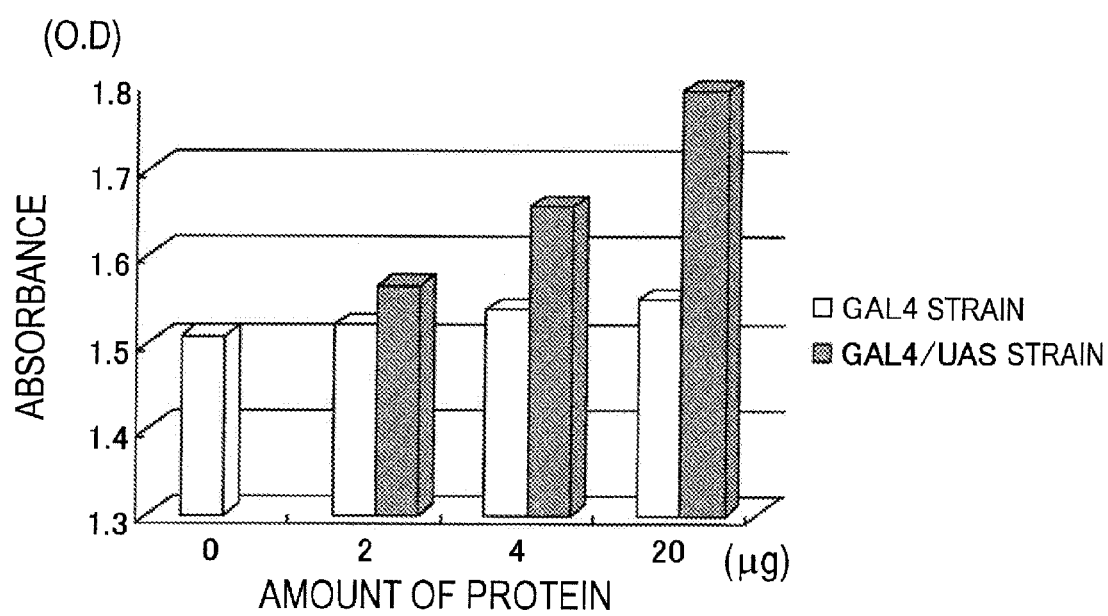
FIG. 6 shows the results of measuring the activity of the recombinant antibody against its antigen by ELISA.

Next, the thus-obtained individuals with the 3XP3GFP and 3XP3DsRed genes were raised as individuals carrying both the UASFvaTf and Ser1GAL4 genes, and samples extracted from the middle silk gland of larvae at the spinning stage were subjected to Western blotting. As a result, antibody production was confirmed in the silk gland as shown in FIG. 5. Furthermore, as a result of antibody reaction in the extracts obtained in the same manner, the amount of substance that reacts with the antigen increased as the amount of silk gland extracts increased, as indicated in FIG. 6. This showed that the extracts had antibody activity.

Figure 4:
FIG. 4 is a photograph showing confirmation of FvaTf gene transcription in the hybrid strain by RT-PCR.

Similarly to Western blotting, total RNAs were extracted from the middle silk glands at the spinning stage, and RT-PCR was performed. As a result, transcription of the introduced gene was greatest on day 5 of the 5th instar and became suppressed with time, as shown in FIG. 4. Therefore, it was found that gene transcription became active on day 5 of the 5th instar, and proteins were translated at the spinning stage and became present in the middle silk gland.

Example 2

Materials and Methods

1. Construction of a Plasmid Vector

In this study, the plasmid vector pBacN/lox p UASIgLUA-SIgH (FIGS. 7 to 9) was prepared using transgenic silkworms to produce an IgG mouse anti-human transferrin antibody that reacts with human transferrin. This vector for production of transgenic silkworms was prepared by inserting between inverted terminal repeats of the piggyBac transposon, the L chain and the H chain of the antibody protein gene fused to the promoter UAS which promotes gene expression in the presence of the yeast transcriptional regulator GAL4.

The L chain of the IgG mouse anti-human transferrin antibody was designed as follows. First, for the antibody L chain, a DNA was designed to have a structure in which an anti-human transferrin antibody Lκ chain variable region, mouse L chain J segment, and mouse Lκ chain constant region are linked downstream of a mouse immunoglobulin L chain κ (IgL) signal peptide in this order. Next, for the H chain of the IgG mouse anti-human transferrin antibody, a DNA was designed to have a structure in which an anti-human transferrin antibody H chain variable region, mouse IgG1 H chain constant region 1 (CH1), mouse IgG1 hinge region, mouse IgG1 H chain constant region 2 (CH2), and mouse IgG1 H chain constant region 3 (CH3) are linked downstream of a mouse IgG1 (IgH) signal peptide in this order. The IgG antibody designed in this experiment belongs to the subclass IgG1 and has the antigenicity of κ chain, and for the L chain and H chain, known amino acid sequences were used. The relation of SEQ ID NOs with the nucleotide sequences of the genes used herein and the amino acid sequences produced from these nucleotide sequences is shown in Table 5.

TABLE 5

| | | | Nucleotide sequence | Amino acid sequence |
|---|---|---|---|---|
| L chain | | Signal sequence | SEQ ID NO: 20 | SEQ ID NO: 21 |
| | | L chain variable region (VL) | SEQ ID NO: 22 | SEQ ID NO: 23 |
| | | Jκ segment | SEQ ID NO: 24 | SEQ ID NO: 25 |
| | | κ chain constant region | SEQ ID NO: 26 | SEQ ID NO: 27 |
| H chain | | Signal sequence | SEQ ID NO: 28 | SEQ ID NO: 29 |
| | | H chain variable region (VH) | SEQ ID NO: 30 | SEQ ID NO: 31 |
| | Mouse full-length γ1 chain constant region | CH1: Constant region domain | SEQ ID NO: 32 | SEQ ID NO: 33 |
| | | H: Hinge region | SEQ ID NO: 34 | SEQ ID NO: 35 |
| | | CH2: Constant region domain | SEQ ID NO: 36 | SEQ ID NO: 37 |
| | | CH3: Constant region domain | SEQ ID NO: 38 | SEQ ID NO: 39 |

2. Construction of a Plasmid Vector

Figure 7:
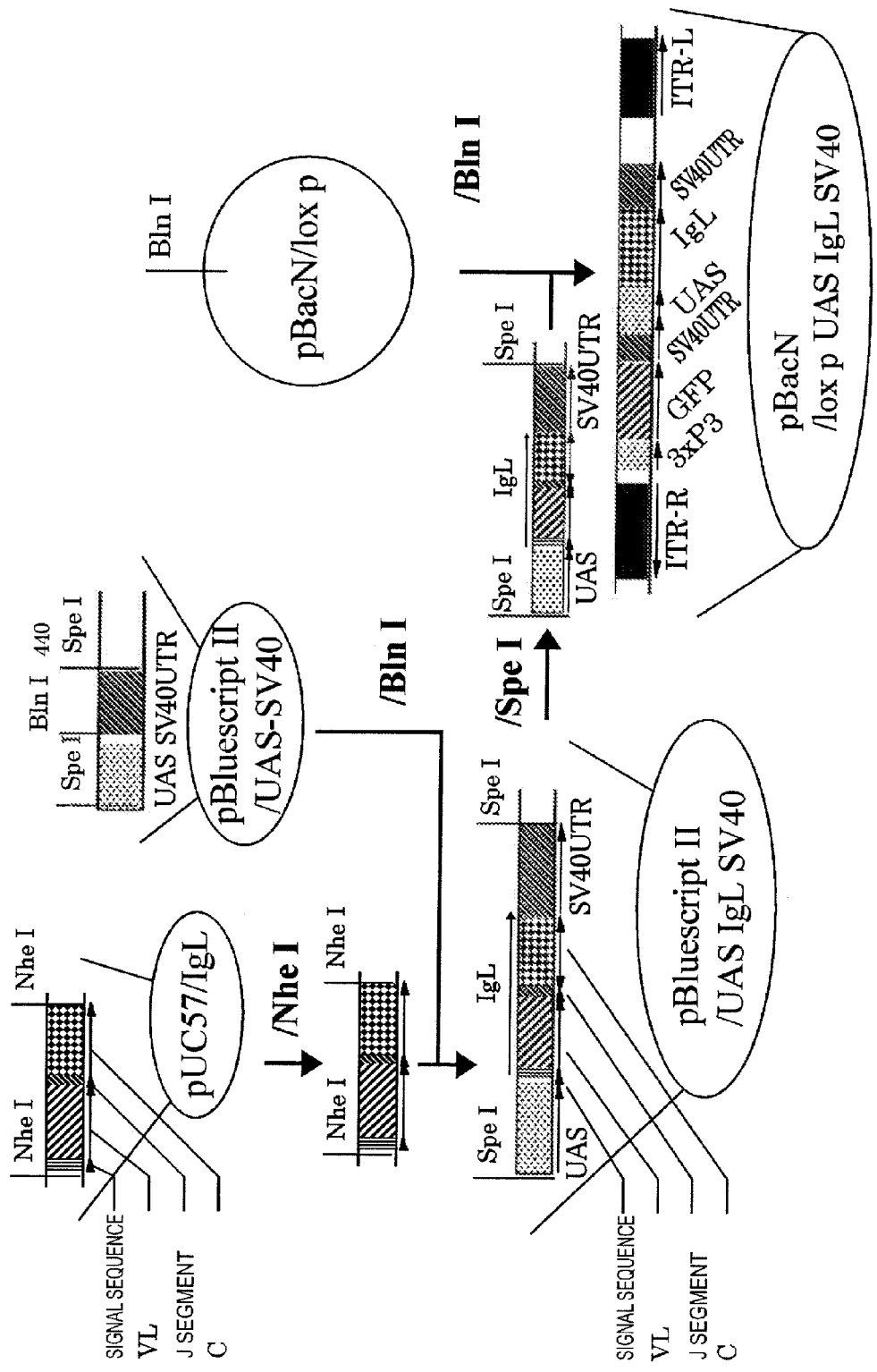
FIG. 7 shows the structure and construction procedure of the pBacN/lox p UAS IgL SV40 plasmid vector which encodes an L chain of an antibody gene for producing transgenic silkworms.
Figure 8:
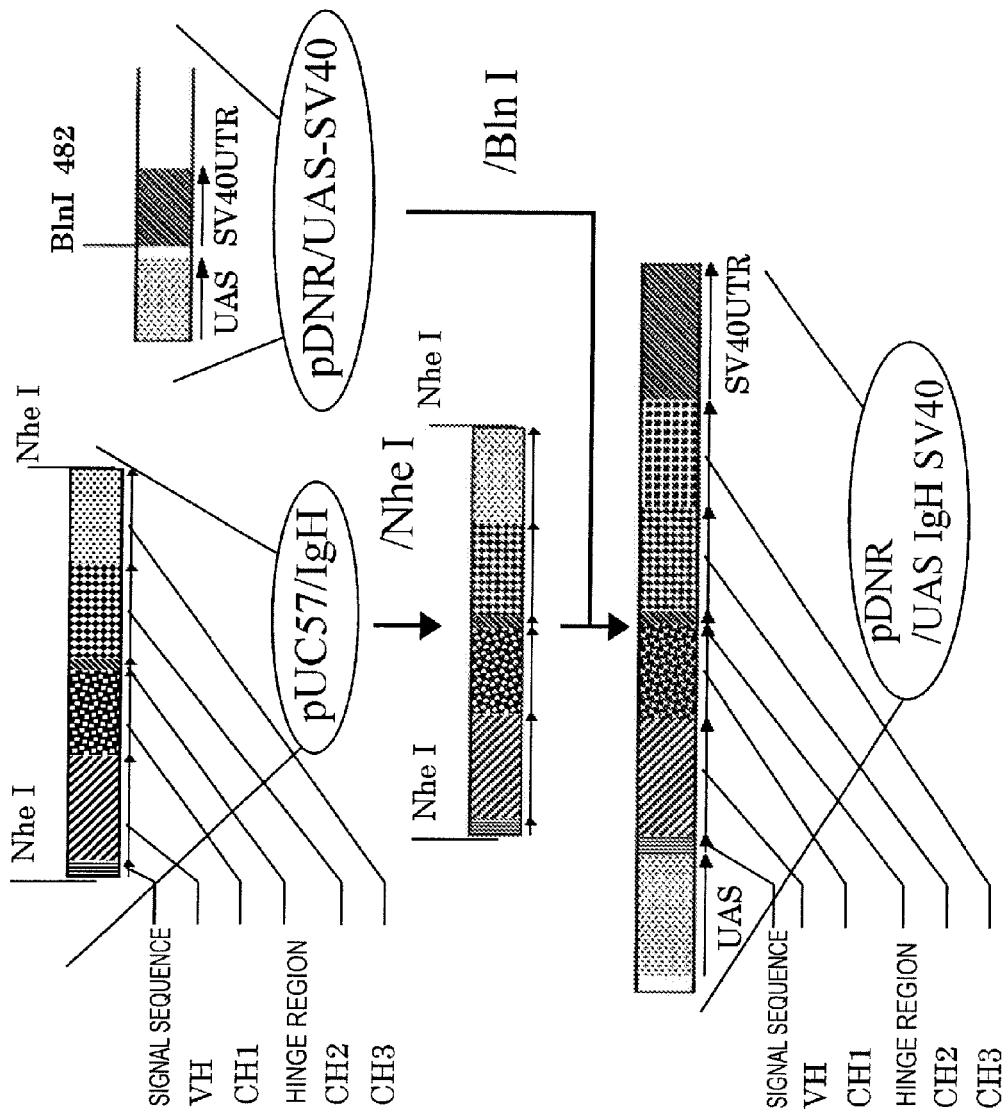
FIG. 8 shows the structure and construction procedure of the pDNA/UAS IgH SV40 plasmid vector which encodes an H chain of an antibody gene for producing transgenic silkworms.
Figure 9:
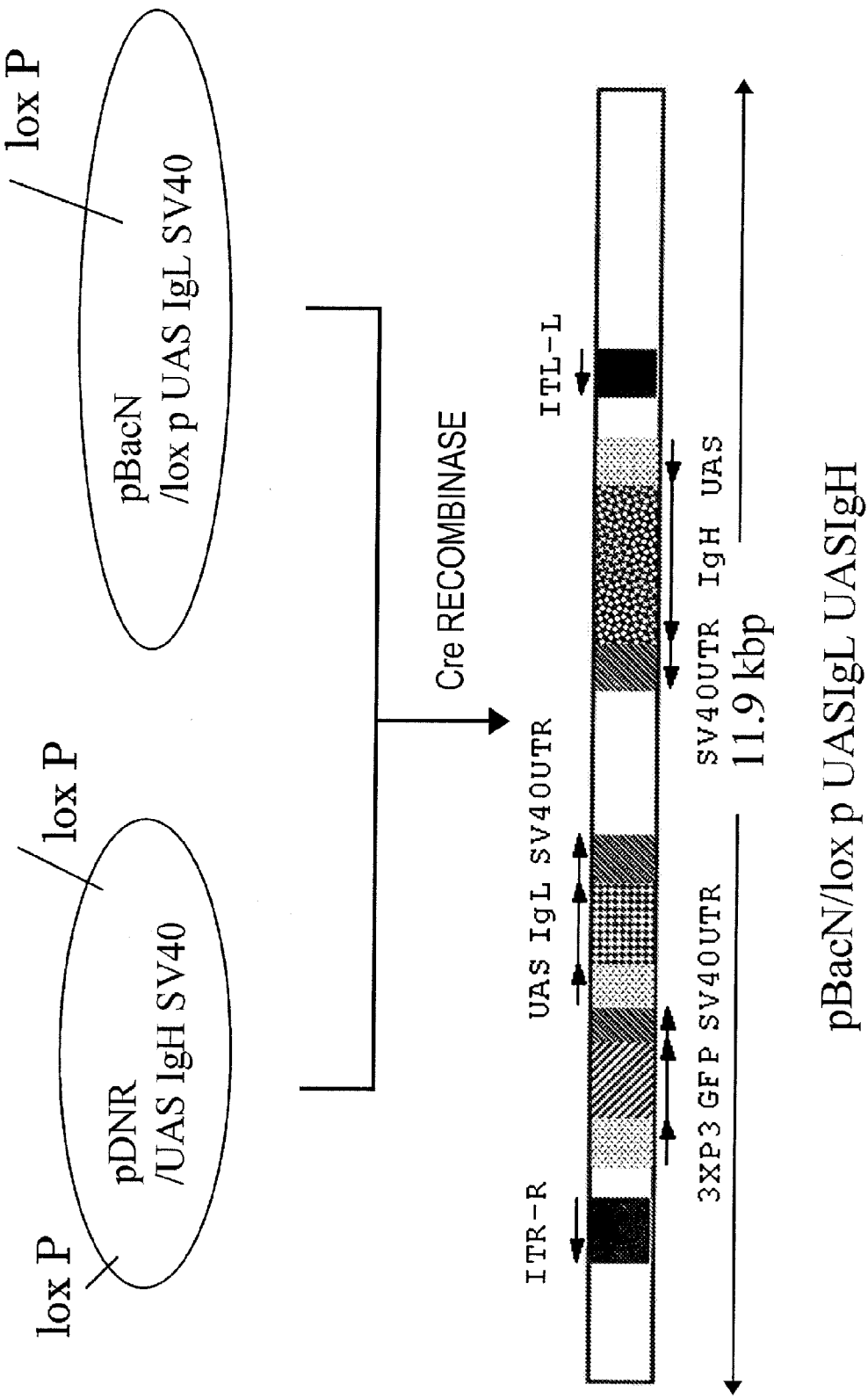
FIG. 9 shows the structure and construction procedure of the pBacN/lox p UASIgL UASIgH vector for producing transgenic silkworms that carry an antibody gene.

A gene plasmid was constructed with a GAL4/UAS system by the procedures shown in FIGS. 7 to 9. More specifically, the IgL fragment was obtained by digesting pUC57/IgL with the restriction enzyme Nhe I, and inserted into the donor vector pBluescript II UAS-SV40 which had been digested with the restriction enzyme Bin I to obtain pBluescript II/UAS IgL SV40. Next, the UAS IgL SV40UTR fragment was obtained by digesting pBluescript II/UAS IgL SV40 with the restriction enzyme Spe I, and inserted into the plasmid vector pBacN/lox p which had been digested with the restriction enzyme Bln I to obtain pBacN/lox p UAS IgL SV40 (FIG. 7). The IgH fragment was obtained by digesting pUC57/IgH with the restriction enzyme Nhe I, and inserted into the donor vector pDNR/UAS-SV40 which had been digested with the restriction enzyme Bln I to obtain pDNR/UAS IgH SV40 (FIG. 8). Next, the UAS IgH SV40UTR fragment was inserted into pBacN/lox p UAS IgL SV40 using Cre Recombinase (FIG. 9: pBacN/loxp UASIgL UASIgH).

3. Establishment of a Strain Expressing a Recombinant Protein

Figure 10:
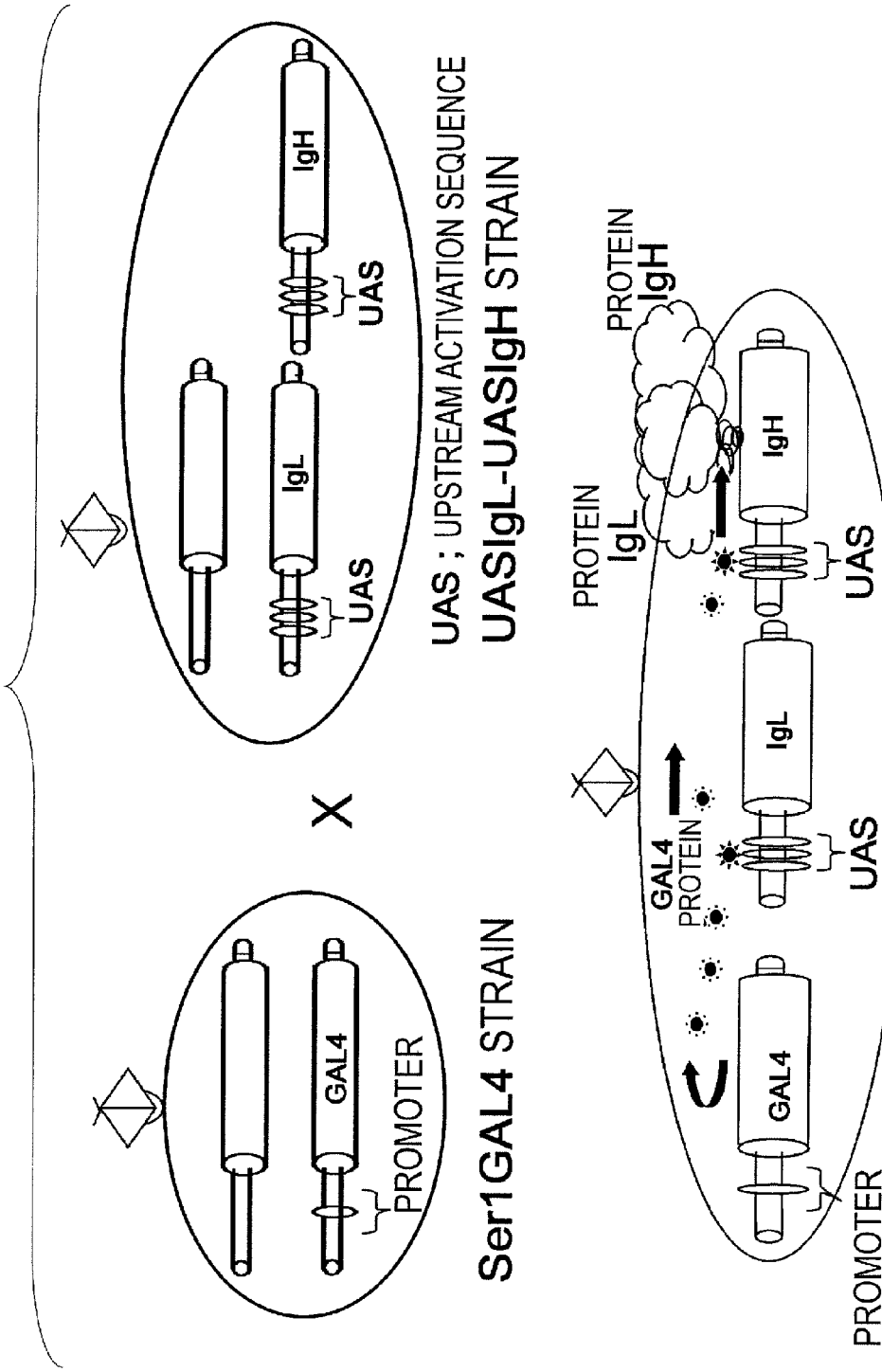
FIG. 10 shows the procedure for producing antibody-expressing silkworms by crossing the Ser1GAL4 strain with the UASIgL-UASIgH strain.

To express this gene at a target site, silkworms of the established Ser1GAL4/3xP3DsRed strain (Tamura, et al., 2004) were used. In these transgenic silkworms, it was confirmed that the GAL4 gene is expressed only in the middle silk gland, and expression of an introduced gene is regulated by UAS (Tamura, et al., 2004). To express the introduced anti-human transferrin IgG antibody, the obtained UASIgL-UASIgH strain having the anti-human transferrin IgG antibody gene was crossed with the above-mentioned GAL4 strain (FIG. 10).

This plasmid vector carries, as a marker gene to identify transgenic silkworms, the green fluorescent protein 3xP3GFP which has a promoter that promotes expression in the ocellus of embryos, compound eyes of moths, and nerve-derived tissues (Horn, C., and E. A. Wimmer, (2000) Dev. Genes Evol. 210: 630-637; Murizio et al. (1994) Protein Science, 3: 1476-1484).

4. RT-PCR

RT-PCR was performed as follows. As described above, individuals having both GAL4/UAS genes were raised, and the middle silk gland was removed from 5th instar silkworms just before the spinning stage. Next, the removed middle silk glands were transferred into a glass homogenizer (WHEATON), and total RNAs were extracted using ISOGEN (Nippon Gene). The total RNAs were adjusted to 50 μg/20 μl in DEPC water, and then reverse transcribed into cDNAs using a First-strand cDNA Synthesis Kit (GE Healthcare Bio-Sciences) according to the attached document. The following PCR was performed for IgL, IgH, GAL4, and intracellular actin using combinations of primers shown in Table 6 and using the reverse transcription product as a template. 5 μl of 10×PCR buffer attached to TaKaRa Ex Taq Hot Start Version (TaKaRa Bio), 100 μM of Forward primer (Table 6), 100 μM of Reverse primer (Table 6), 0.2 μM of dNTP, and 2.5 units of TaKaRa Ex Taq Hot Start Version were mixed, and the total volume was adjusted to 50 μl. PCR was carried out using an Eppendorf thermal cycler with one cycle of 94° C., 2 minutes; 40 cycles of 94° C., 15 seconds, 60° C., 15 seconds, and 72° C., 30 seconds; and 72° C., 1 minute for elongation reaction.

5. Detection of an IgG1 Antibody

Figure 11:
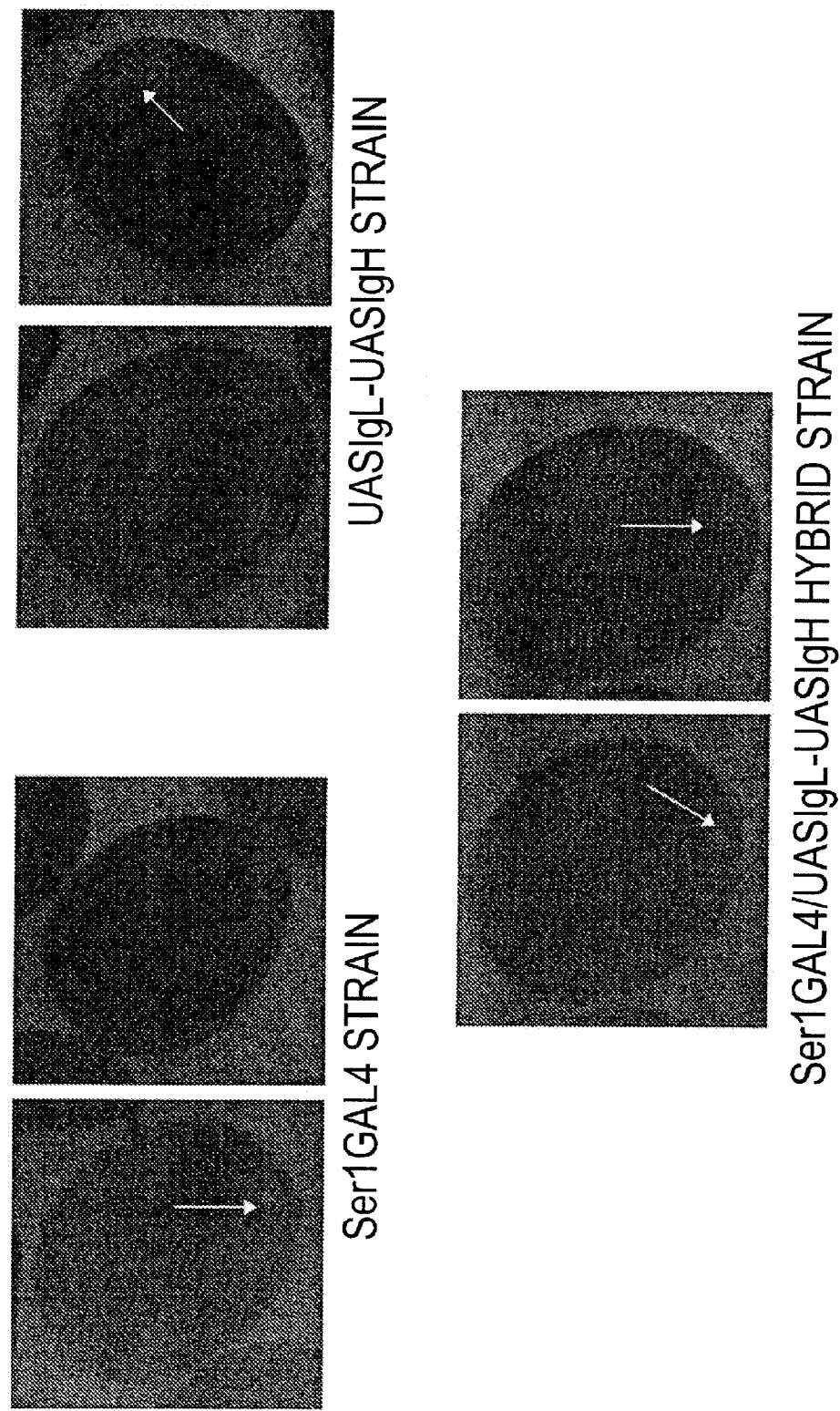
FIG. 11 shows fluorescence stereo micrographs of individuals carrying the GAL4 gene and individuals carrying UAS.

Detection of the IgG mouse antibody was carried out as follows. Eggs of the next generation were obtained by crossing the Ser1GAL4/3xP3DsRed strain with UASIgL-UASIgH strain, and observed 6 days after oviposition under a fluorescence stereomicroscope; and the GAL4/UAS individuals were identified (FIG. 11). Only the individuals having both genes were raised; the silk gland was removed from 5th instar silkworms at the spinning stage; and proteins in the silk gland were extracted using 20 mM Tris-HCl pH 7.4 (Tris buffer). Antibodies were detected in this protein solution using a Mouse Monoclonal Antibody Isotyping Kit (GE Healthcare Bio-Sciences). More specifically, a typing stick was soaked in the protein solution extracted from the silk glands of silkworms, and then shaken for 18 hours at room temperature. After a washing procedure according to the attached document, a peroxidase-labeled anti-mouse antibody was added, and this was shaken for six hours at room temperature. Next, a washing procedure was conducted, and then the stick was soaked in a substrate solution to confirm bands.

6. Examination of the Reactivity of a Recombinant Antibody with an Antigen

Measurement of the reactivity of the recombinant IgG antibody against an antigen by enzyme-linked immunosorbent assay (ELISA) was carried out by the following procedure. The middle silk gland was removed from Ser1GAL4/UASIgL-UASIgH strain silkworms and Ser1GAL4 strain silkworms that did not have UASIgL-UASIgH in their spinning stage, and 3 ml of Tris buffer was added. This was homogenized using a glass homogenizer and centrifuged at 12,000 rpm for 20 minutes, and then the supernatant was used as a stock solution of middle silk gland extract sample. The stock solution was diluted two-fold and four-fold with Tris buffer. These samples and the undiluted sample (stock solution) were used as samples for ELISA measurement. Furthermore, similar procedures were performed on the Ser1GAL4 strain silkworms to prepare samples for ELISA measurement as a negative control. Quantitative determination of proteins in stock solution samples of the Ser1GAL4/UASIgL-UASIgH strain and the Ser1GAL4 strain were conducted by the Bradford method (Quick Start protein assay staining solution: BIO-RAD) (Table 7).

100 μl of the samples for ELISA measurement prepared as described above were dispensed into a microtiter plate (NUNC) presensitized with 1 μg/well of transferrin (Biogenesis), and the plate was shaken at room temperature for three hours. Next, the samples for ELISA measurement were removed from the wells, and the wells were washed three times with 200 μl of PBS-T. A peroxidase-labeled anti-mouse immunoglobulin goat polyclonal antibody (Dako) was subsequently dispensed at 100 μl, the plate was shaken at room temperature for four hours, and then the wells were washed five times with 200 μl of PBS-T.

3,3',5,5'-Tetramethylbenzidine (Roche Japan) was added for color development. Exactly four minutes after addition of 3,3',5,5'-tetramethylbenzidine, 100 μl of 1 N sulfuric acid was dispensed to stop color development. After that, the absorbance at 450 nm was measured using a model 550 microplate reader (BioRad).

TABLE 6

| Primer | IgL | IgH | GAL4 | Actin |
| --- | --- | --- | --- | --- |
| Forward primer | SEQ ID NO: 40 | SEQ ID NO: 42 | SEQ ID NO: 44 | SEQ ID NO: 46 |
| Reverse primer | SEQ ID NO: 41 | SEQ ID NO: 43 | SEQ ID NO: 45 | SEQ ID NO: 47 |

TABLE 7

|  | Ser1GAL4/UASIgL-UASIgH | Control |
| --- | --- | --- |
| Amount of protein (mg/ml) | 0.39 | 0.97 |

Results and Discussion

The plasmid prepared by the method described above, and helper plasmid pA3PIG encoding a transferase gene (Tamura et al., 2000) were injected together into approximately 700 silkworm eggs at an early developmental stage, and GFP expression in the ocellus of embryos of the next generation was examined. As a result, as shown in Table 8, individuals expressing GFP were found in seven moth broods.

TABLE 8

| Vector | Number of injected eggs | Number of moth eggs examined | Number of transgenic moth broods |
|---|---|---|---|
| pBacN/loxp UASIgL UASIgH | 1,684 | 214 | 7 |

As a result of raising these transgenic silkworms, three strains could be successfully established. Furthermore, one of the established UASIgL-IgH strains was crossed with the Ser1GAL4 strain, and the segregation ratio of individuals carrying each of the fluorescent protein genes in the next generation is shown in Table 9.

TABLE 9

| | Marker | | | |
|---|---|---|---|---|
| | DsRed | GFP | DsRed/GFP | Negative |
| Number of positive individuals | 73 | 69 | 64 | 61 |
| Segregation ratio (%) | 27.3 | 25.8 | 24.0 | 22.8 |

Since these values match the theoretical values when individuals heterozygous for both genes are crossed with each other, the two genes were found to be inserted into different chromosomes and inherited independently. In this case, transgenic silkworms having either or both of 3xP3GFP and 3xP3DsRed could be easily identified, since their ocellus and nerve-derived tissues showed fluorescence when observed under a fluorescence stereomicroscope during the embryonic stage as shown in FIG. 11.

Next, the thus-obtained individuals having the 3xP3GFP and 3xP3DsRed genes were raised as individuals having both the UASIgL UASIgH and Ser1GAL4 genes, and whether samples extracted from the silk gland of larvae at the spinning stage contain IgG1 antibodies was confirmed using a Mouse Monoclonal Antibody Isotyping Kit. As a result, a mouse IgG1 antibody having a κ chain was found to be produced in the silk gland as shown in FIG. 13. Furthermore, when samples extracted from the silk glands were reacted with an antigen in the same manner, the recombinant protein produced by the transgenic silkworms was found to function as an antibody as shown in FIG. 14.

In a similar manner to detection of the IgG1 antibody, total RNAs were extracted from the middle silk gland, and RT-PCR was performed. As a result, genes of both the antibody L chain and H chain were found to be transcribed as shown in FIG. 12.

INDUSTRIAL APPLICABILITY

The present invention provides methods for producing recombinant antibodies using silkworms. Insects do not carry antibody molecules. Accordingly, an advantage of producing recombinant antibodies using silkworms is that antibodies other than those of interest cannot be included in recombinant antibody extracts. This means that in contrast to mammals such as mice, there is no need to produce knockout individuals. When using mammal-derived cultured cells and such, antibodies derived from the animal cells may be included in purified products of produced recombinant antibodies. This causes cross reactions and interferes with accurate measurement of the quantity of antigen. When using silkworm-derived recombinant antibodies, cross reactions are unlikely to occur and only antibodies that react with antigens of interest can be accurately measured. Furthermore, antibodies can be produced in large amounts by using silkworms. The present invention is particularly useful in the fields of pharmaceuticals and diagnostic agents in which large amounts of highly specific antibodies are necessary.

The invention claimed is:

1. A method for producing a soluble and active recombinant antibody, wherein the method comprises the steps of:
   (a) producing a transgenic silkworm whose genome comprises a promoter of a DNA encoding a protein specifically expressed in the silk gland operatively linked to a DNA encoding a signal sequence-comprising recombinant antibody, and which secretes the recombinant antibody into the silk gland; and
   (b) recovering soluble and active recombinant antibody from the silk gland of, or a cocoon spun by the transgenic silkworm,
   wherein the promoter of a DNA encoding a protein specifically expressed in the silk gland is a promoter of a DNA encoding sericin 1 protein or the fibroin protein.

2. A method for producing a soluble and active recombinant antibody wherein the method comprises producing a transgenic silkworm whose genome comprises a transcriptional regulator-encoding DNA operably linked downstream of a promoter of a DNA encoding a protein specifically expressed in the silk gland; and wherein the DNA encoding the recombinant antibody is operably linked downstream of a target promoter of the transcriptional regulator,
   wherein the promoter of a DNA encoding a protein specifically expressed in the silk gland is a promoter of a DNA encoding sericin 1 protein or the fibroin protein, and
   wherein the transcriptional regulator is GAL4 and the target promoter is UAS (Upstream Activation Sequence) or the transcriptional regulator is TetR and the target promoter is TRE.

3. The method of claim 2, wherein the transgenic silkworm in produced by crossing parental transgenic silkworms of (i) and (ii) below:
   (i) a parental transgenic silkworm comprising a transcriptional regulator-encoding DNA operably linked downstream of the promoter of a DNA encoding a protein specifically expressed in the silk gland; and
   (ii) a parental transgenic silkworm comprising the DNA encoding the recombinant antibody, which is operably linked downstream of a target promoter of the transcriptional regulator, wherein the promoter of the DNA encoding a protein specifically expressed in the silk gland is a promoter of a DNA encoding sericin 1 protein or the fibroin protein, and wherein the transcriptional regulator is a GAL4 and the target promoter is UAS (Upstream Activation Sequence) or the transcriptional regulator is TetR and the target promoter is TRE.

* * * * *

SEQUENCE LISTING

```
<160> NUMBER OF SEQ ID NOS: 51

<210> SEQ ID NO 1
<211> LENGTH: 57
<212> TYPE: DNA
<213> ORGANISM: Homo sapiens

<400> SEQUENCE: 1
atggacatgt ggacggcgct gctcatcctg caagccttgt tgctaccctc cctggct        57

<210> SEQ ID NO 2
<211> LENGTH: 57
<212> TYPE: DNA
<213> ORGANISM: Artificial
<220> FEATURE:
<223> OTHER INFORMATION: An artificial synthesized nucleotide sequence

<400> SEQUENCE: 2
atggacatgt ggaccgctct gctcatcctg caagctctgc tcctgccctc cctggct        57

<210> SEQ ID NO 3
<211> LENGTH: 19
<212> TYPE: PRT
<213> ORGANISM: Homo sapiens
```

<400> SEQUENCE: 3

Met Asp Met Trp Thr Ala Leu Leu Ile Leu Gln Ala Leu Leu Leu Pro
1               5                   10                  15

Ser Leu Ala

<210> SEQ ID NO 4
<211> LENGTH: 363
<212> TYPE: DNA
<213> ORGANISM: Mus musculus

<400> SEQUENCE: 4
ctcgaggtcc agctgcagga gtcgggacct gacctggtga accttctca gtcactttca       60 ctcacctgca ctgtcactgg ctactccatc accagtggtt atagctgcca ctggattcgg      120
cagtttccag aaaacaaact ggaatggctg ggctacatac actccagtgg tgccactaac     180
tacagcccat ctctcaaaag tcgattctct atcactagag acacatccaa gaaccagttc      240
ttcctgcagt tgaactctgt gactactgag acacagcca catattactg tgcaagggat      300
ggttactccc ctccctatgc tatggactat tggggccaag gaccacggt caccgtctcc      360 tca                                                                    363

<210> SEQ ID NO 5
<211> LENGTH: 363
<212> TYPE: DNA
<213> ORGANISM: Artificial
<220> FEATURE:
<223> OTHER INFORMATION: An artificial synthesized nucleotide sequence

<400> SEQUENCE: 5
ctggaagtgc aactgcaaga atccggtccc gatctggtga accctcccca atccctgtcc       60
ctgacctgca ccgtgaccgg ttactccatc acctccggtt actcctggca ctggatcagg      120
cagttccccg agaacaagct ggagtggctg ggttacatcc actcctccgg tgctaccaac     180
tactcccccc t ccctgaagtc ccgtttctcc atcacccgtg acacctccaa gaaccagttc   240
ttcctgcaac tgaactccgt gaccaccgaa gataccgcta ctactactg cgctcgtgat     300 ggttactccc cccctacgc tatggactac tggggtcaag gtaccaccgt gaccgtctcc      360
tcc                                                                    363

<210> SEQ ID NO 6
<211> LENGTH: 121
<212> TYPE: PRT
<213> ORGANISM: Mus musculus

<400> SEQUENCE: 6

Leu Glu Val Gln Leu Gln Glu Ser Gly Pro Asp Leu Val Lys Pro Ser
1               5                   10                  15

Gln Ser Leu Ser Leu Thr Cys Thr Val Thr Gly Tyr Ser Ile Thr Ser
                20                  25                  30

Gly Tyr Ser Trp His Trp Ile Arg Gln Phe Pro Glu Asn Lys Leu Glu
            35                  40                  45

Trp Leu Gly Tyr Ile His Ser Ser Gly Ala Thr Asn Tyr Ser Pro Ser
        50                  55                  60

Leu Lys Ser Arg Phe Ser Ile Thr Arg Asp Thr Ser Lys Asn Gln Phe
65                  70                  75                  80

Phe Leu Gln Leu Asn Ser Val Thr Thr Glu Asp Thr Ala Thr Tyr Tyr
                85                  90                  95

Cys Ala Arg Asp Gly Tyr Ser Pro Pro Tyr Ala Met Asp Tyr Trp Gly
            100                 105                 110

Gln Gly Thr Thr Val Thr Val Ser Ser
        115                 120

<210> SEQ ID NO 7
<211> LENGTH: 48
<212> TYPE: DNA
<213> ORGANISM: Artificial
<220> FEATURE:
<223> OTHER INFORMATION: An artificial synthesized nucleotide sequence

<400> SEQUENCE: 7
ggtggaggcg gttcaggcgg aggtggctct ggcggtggcg gatcggac                    48

<210> SEQ ID NO 8
<211> LENGTH: 48
<212> TYPE: DNA
<213> ORGANISM: Artificial
<220> FEATURE:
<223> OTHER INFORMATION: An artificial synthesized nucleotide sequence

<400> SEQUENCE: 8
ggcggcggcg gctccggcgg tggtggctcc ggtggtggtg gttccgat                    48

<210> SEQ ID NO 9
<211> LENGTH: 16
<212> TYPE: PRT
<213> ORGANISM: Artificial
<220> FEATURE:
<223> OTHER INFORMATION: An artificial synthesized nucleotide sequence

<400> SEQUENCE: 9

Gly Gly Gly Gly Ser Gly Gly Gly Gly Ser Gly Gly Gly Gly Ser Asp
1               5                   10                  15

<210> SEQ ID NO 10
<211> LENGTH: 339
<212> TYPE: DNA
<213> ORGANISM: Mus musculus

<400> SEQUENCE: 10
attgagctca cccagtctcc atcctcccta gctgtgtcag ttggagagaa ggttactatg       60
acctgcaagt ccagtcagag cctttttatat agtaccaatc aaaagaacta cttggcctgg     120
taccagcaga aaccagggca gtctcctaaa ctgctgattt actgggcatc cactagggaa     180
tctggggtcc ctgatcgctt cacaggcagt ggatctggga cagatttcac tctcaccatc     240
agcagtgtga aggctgaaga cctgtcagtt tattactgtc agcaatatta gctatcct      300 cccacgttcg gctcgggcac caagcttgaa atcaaataa                             339

<210> SEQ ID NO 11
<211> LENGTH: 339
<212> TYPE: DNA
<213> ORGANISM: Artificial
<220> FEATURE:
<223> OTHER INFORMATION: An artificial synthesized nucleotide sequence

<400> SEQUENCE: 11
atcgaactga cccaatcccc ctcctccctg gctgtgtccg tgggtgagaa ggtgaccatg       60
acctgcaagt cctcccagtc cctgctctac tccaccaacc agaagaacta cctggcttgg     120
taccaacaaa aacccggtca gtcccccaag ctgctcatct actgggcttc cacccgtgaa     180

```
tccggtgtgc cgatcgttt caccggttcc ggttccggta ccgacttcac cctgaccatc    240
tcctccgtga aggctgagga cctgtccgtg tactactgcc agcaatacta ctcctacccc    300
cccaccttcg gttccggtac caagcttgag atcaagtaa                          339
```

<210> SEQ ID NO 12
<211> LENGTH: 112
<212> TYPE: PRT
<213> ORGANISM: Mus musculus

<400> SEQUENCE: 12

```
Ile Glu Leu Thr Gln Ser Pro Ser Ser Leu Ala Val Ser Val Gly Glu
1               5                   10                  15

Lys Val Thr Met Thr Cys Lys Ser Ser Gln Ser Leu Leu Tyr Ser Thr
            20                  25                  30

Asn Gln Lys Asn Tyr Leu Ala Trp Tyr Gln Gln Lys Pro Gly Gln Ser
        35                  40                  45

Pro Lys Leu Leu Ile Tyr Trp Ala Ser Thr Arg Glu Ser Gly Val Pro
    50                  55                  60

Asp Arg Phe Thr Gly Ser Gly Ser Gly Thr Asp Phe Thr Leu Thr Ile
65                  70                  75                  80

Ser Ser Val Lys Ala Glu Asp Leu Ser Val Tyr Tyr Cys Gln Gln Tyr
                85                  90                  95

Tyr Ser Tyr Pro Pro Thr Phe Gly Ser Gly Thr Lys Leu Glu Ile Lys
            100                 105                 110
```

<210> SEQ ID NO 13
<211> LENGTH: 807
<212> TYPE: DNA
<213> ORGANISM: Artificial
<220> FEATURE:
<223> OTHER INFORMATION: An artificial synthesized nucleotide sequence

<400> SEQUENCE: 13

```
atggacatgt ggacggcgct gctcatcctg caagccttgt tgctaccctc cctggctctc    60
gaggtccagc tgcaggagtc gggacctgac ctggtgaaac cttctcagtc actttcactc    120
acctgcactg tcactggcta ctccatcacc agtggttata ctggcactg gattcggcag    180 tttccagaaa acaaactgga atggctgggc tacatacact ccagtggtgc cactaactac    240
agcccatctc tcaaaagtcg attctctatc actagagaca catccaagaa ccagttcttc    300
ctgcagttga actctgtgac tactgaggac acagccacat attactgtgc aagggatggt    360 tactccctc cctatgctat ggactattgg ggccaaggga ccacggtcac cgtctcctca    420
ggtggaggcg gttcaggcgg aggtggctct ggcggtggcg gatcggacat tgagctcacc    480
cagtctccat cctccctagc tgtgtcagtt ggagagaagg ttactatgac ctgcaagtcc    540
agtcagagcc ttttatatag taccaatcaa aagaactact ggcctggta ccagcagaaa    600 ccagggcagt ctcctaaact gctgatttac tgggcatcca ctagggaatc tggggtccct    660
gatcgcttca caggcagtgg atctgggaca gatttcactc tcaccatcag cagtgtgaag    720
gctgaagacc tgtcagttta ttactgtcag caatattata gctatcctcc cacgttcggc    780
tcgggcacca agcttgaaat caaataa                                        807
```

<210> SEQ ID NO 14
<211> LENGTH: 807
<212> TYPE: DNA
<213> ORGANISM: Artificial

<220> FEATURE:
<223> OTHER INFORMATION: An artificial synthesized nucleotide sequence

<400> SEQUENCE: 14

```
atggacatgt ggaccgctct gctcatcctg caagctctgc tcctgccctc cctggctctg      60
gaagtgcaac tgcaagaatc cggtcccgat ctggtgaaac cctcccaatc cctgtccctg     120
acctgcaccg tgaccggtta ctccatcacc tccggttact cctggcactg gatcaggcag     180
ttccccgaga caagctgga gtggctgggt tacatccact cctccggtgc taccaactac     240
tcccctccc tgaagtcccg tttctccatc acccgtgaca cctccaagaa ccagttcttc     300
ctgcaactga actccgtgac caccgaagat accgctacct actactgcgc tcgtgatggt     360
tactcccccc cctacgctat ggactactgg ggtcaaggta ccaccgtgac cgtctcctcc     420
ggcggcggcg gctccggcgg tggtggctcc ggtggtggtg gttccgatat cgaactgacc     480
caatcccct cctccctggc tgtgtccgtg ggtgagaagg tgaccatgac ctgcaagtcc     540
tcccagtccc tgctctactc caccaaccag aagaactacc tggcttggta ccaacaaaaa     600
cccggtcagt cccccaagct gctcatctac tgggcttcca cccgtgaatc cggtgtgccc     660
gatcgtttca ccggttccgg ttccggtacc gacttcaccc tgaccatctc ctccgtgaag     720
gctgaggacc tgtccgtgta ctactgccag caatactact cctaccccc caccttcggt     780
tccggtacca agcttgagat caagtaa                                          807
```

<210> SEQ ID NO 15
<211> LENGTH: 268
<212> TYPE: PRT
<213> ORGANISM: Artificial
<220> FEATURE:
<223> OTHER INFORMATION: An artificial synthesized peptide sequence

<400> SEQUENCE: 15

```
Met Asp Met Trp Thr Ala Leu Leu Ile Leu Gln Ala Leu Leu Leu Pro
1               5                   10                  15

Ser Leu Ala Leu Glu Val Gln Leu Gln Glu Ser Gly Pro Asp Leu Val
                20                  25                  30

Lys Pro Ser Gln Ser Leu Ser Leu Thr Cys Thr Val Thr Gly Tyr Ser
            35                  40                  45

Ile Thr Ser Gly Tyr Ser Trp His Trp Ile Arg Gln Phe Pro Glu Asn
        50                  55                  60

Lys Leu Glu Trp Leu Gly Tyr Ile His Ser Ser Gly Ala Thr Asn Tyr
65                  70                  75                  80

Ser Pro Ser Leu Lys Ser Arg Phe Ser Ile Thr Arg Asp Thr Ser Lys
                85                  90                  95

Asn Gln Phe Phe Leu Gln Leu Asn Ser Val Thr Thr Glu Asp Thr Ala
            100                 105                 110

Thr Tyr Tyr Cys Ala Arg Asp Gly Tyr Ser Pro Pro Tyr Ala Met Asp
        115                 120                 125

Tyr Trp Gly Gln Gly Thr Thr Val Thr Val Ser Ser Gly Gly Gly Gly
    130                 135                 140

Ser Gly Gly Gly Gly Ser Gly Gly Gly Gly Ser Asp Ile Glu Leu Thr
145                 150                 155                 160

Gln Ser Pro Ser Ser Leu Ala Val Ser Val Gly Glu Lys Val Thr Met
                165                 170                 175

Thr Cys Lys Ser Ser Gln Ser Leu Leu Tyr Ser Thr Asn Gln Lys Asn
            180                 185                 190
```

```
Tyr Leu Ala Trp Tyr Gln Gln Lys Pro Gly Gln Ser Pro Lys Leu Leu
            195                 200                 205

Ile Tyr Trp Ala Ser Thr Arg Glu Ser Gly Val Pro Asp Arg Phe Thr
    210                 215                 220

Gly Ser Gly Ser Gly Thr Asp Phe Thr Leu Thr Ile Ser Ser Val Lys
225                 230                 235                 240

Ala Glu Asp Leu Ser Val Tyr Tyr Cys Gln Gln Tyr Ser Tyr Pro
                245                 250                 255

Pro Thr Phe Gly Ser Gly Thr Lys Leu Glu Ile Lys
            260                 265

<210> SEQ ID NO 16
<211> LENGTH: 1935
<212> TYPE: DNA
<213> ORGANISM: Bombyx mori

<400> SEQUENCE: 16
```

| | | | | | |
|---|---|---|---|---|---|
| gaaattctta | gctacatcta | gcccagactg | taagagtttc | ttaggagctt | tagaagttaa | 60 |
| agaagtacct | ttgtgttgct | gatccttcta | tatcatctgg | tcctagtaaa | ggtactctct | 120 |
| tataatctcc | ttcctaattc | cttacctgct | atttatcgat | tgtaggtcgt | cttggaaacc | 180 |
| agtaccactg | tacaaactcg | cgccccatta | gtaacgtgat | ttgaacggcc | aaccaattga | 240 |
| tgttttaatg | caattaatat | cgtatcttta | accccaacgt | ggttctgcgt | taactaagtg | 300 |
| ctcaccgctg | tcaacagcaa | taaaaccatt | tttgaaataa | taacatcatt | acactaacat | 360 |
| agtgagctag | tcgcaaaatg | tatgtagaga | gaaaacaaac | cttctttggg | gtgttgagag | 420 |
| gaaatcgctg | gattagaact | atcgtgaaga | ccattcactg | atcctgtgta | cttaaattcg | 480 |
| cggattcagc | attaagcgcc | ggatctcagt | tccatcgtaa | tcccagttaa | agaggtgaaa | 540 |
| ttagctatca | cttcgatatc | tgttctgaaa | gcaatgttcc | acttgtaaaa | gcataagcgg | 600 |
| tcagaaacct | tgttaaccaa | tagagccaaa | tatagttaac | acaatagaaa | tttatccaaa | 660 |
| tattattcgt | gtattgttta | tagcctttgt | caagtctttt | acaaggcaag | ataataagta | 720 |
| atattccgtg | attggacgta | acatttcccg | gaagatcctt | agccgataag | tcgaagagcc | 780 |
| gcatgtggct | agagagacgc | gggtttccga | ccactggctt | aggcgcttat | tccgccataa | 840 |
| tagatgtacg | tgttcacaat | tagcacccga | aattcgtaat | agctacgaga | agtatcgaat | 900 |
| atcaaaaatc | tatatattaa | tacgtgaagc | aaaaactttg | tatcccttt | tacgaaaatt | 960 |
| gcgaggacgg | aggagtatga | aatttcccac | acttatagag | aatacagaga | agaagtgcac | 1020 |
| aatgctaata | tttttttaaa | ataatgcata | aagatactt | taaatcaata | aagaaaacag | 1080 |
| cacacacact | acataccatg | tatttgacgc | acacacgcat | gtatactatt | tattgtcaaa | 1140 |
| cttttgttct | tgacgtctgt | gttcaaactg | agaatagatt | aaatattgtt | tgtctttatt | 1200 |
| aatatttttt | aatagtgtag | tcttggcgaa | atttgtgatt | atagaagtat | aaaatacaat | 1260 |
| cataatagtg | tacaaactta | caattcccaa | ttaattatag | tcgaatttcg | actactgcgg | 1320 |
| gacctctagt | attaataatt | ctctttaaaa | aaaaacagag | catcaaatac | tgtcacaaat | 1380 |
| gtcaagcggg | tctcaacgag | ccatgaataa | attagaaatc | aattaataac | ataaatagg | 1440 |
| caaacaaaat | aaaaccattt | acatagagaa | cgtttgttga | acaaaaacaa | taacttgtat | 1500 |
| acattgtttg | cacaaatgtt | tgaaccgaaa | atttattact | ctctacgtaa | gcttgatcaa | 1560 |
| acttcgtttt | cgtataaaac | gcgttggccc | aaccactttg | gcatagtcgt | cttatcatcg | 1620 |
| ggtctctaag | gatcaagcga | tccaaagacc | gccaacatgc | gtttcgttct | gtgctgcact | 1680 |

-continued

| | |
|---|---|
| ttgattgcgt tggctgtgag tatcattgct tcgttatcaa caatgacgta tttactaaga | 1740 |
| acactcttag atatgccttc aaattaaagc tttcaaagct ctgaagttca ccaaatgcga | 1800 |
| ctgttttagc gtaagcattt ctatccccca acagccattt agcgactacc cgaaaatcac | 1860 |
| tcgatttaac ttgggagttt ctgcaattta aaagttcaca ggtcgtctcc gattatactt | 1920 |
| ttaaacgctt cgcgc | 1935 |

<210> SEQ ID NO 17
<211> LENGTH: 2036
<212> TYPE: DNA
<213> ORGANISM: Bombyx mori

<400> SEQUENCE: 17

| | |
|---|---|
| cagaatctac cacgatcgga aacgcgaccc actgagaaga tccggcgaga aactcagtga | 60 |
| gctgtgtcta tgggttaatt tactcgtcga gccctgttta ctgtttaggg cgacgtcgac | 120 |
| tgttaccatt cggtctacag gatcgagtgt gcattcttgt atcatcgttc tattatcacg | 180 |
| agtcattttg cgttttttcg gatccctgg aagtcgtcgt ggcctaagag ataagaagtc | 240 |
| cggtgcattc gtgttgagcg atgcacctgt gttcgaatcc taggcgggta ccaattttc | 300 |
| taatgaatta cgtacccaac aaatgttcac gattgccttc cacggtgaag gaataacatc | 360 |
| gtgcaataaa agtgaaaccc gcaaaatccg gtgcttttaa gcttttcaag caccggtcac | 420 |
| catcctcgtt gaactcatcg atctacaagc gatctaatct atagacccaa tccactaaga | 480 |
| tctcaccgga tcttctcagt ggttcgcatt ccagtggtag attcaattcg ctgctcttgc | 540 |
| tagggctagt gttagcaaat tccttcgggt taagcccgag agctcaccta tccgtccgcg | 600 |
| ctaagctgga aaagccccct aagctgtttt tttttgtat agcctttatt gctaatacta | 660 |
| aacaataact aataatttta catacagtaa caaattgttt taacttaaat ctaatacatc | 720 |
| ggatttcccg gttcagtgat cagcgtgtcc tgtgacacat aggcctcttc cagctgcttt | 780 |
| cattttctc tattggtagc ttttcttgac cagattgtct ctccaatcat cttgatatcg | 840 |
| tctgtccatc ttctagcttg cctggctctt ttccttaaa ccaggggtcg tgaattcaat | 900 |
| cctcacagga agccgggatt aggtgggaga atatagttcc gatgttttga atgctttata | 960 |
| ttttctgtgg tcgaaaatga tactagagct acgcgtcgac aattgaatat tatgctaact | 1020 |
| accctctatt tattaaaaga cttttacgat tcatttcgca cagaaccaat cgactgggtt | 1080 |
| tagaggttta gcagtttgtt gaatgaactc gttttcatct tcacgattag aggatcccag | 1140 |
| gtgttaggta aaggatattc tagattgcag gagattttc ataaataatc acgcgatgga | 1200 |
| gcggtaatca gccaacatag tcgatcggca tcattattgg agaccaaaca cacttcagt | 1260 |
| tatccaagcg cgtcttaagt cgcattcgga taatcttgaa tagcctggaa gtgaattttt | 1320 |
| aaaaagtttg tctcgaacaa acatcaatta ctttgtaatt gaaccgaaaa agaggataa | 1380 |
| acattattag cattcgttgt aatgaaatat aatgttgaca cagtttgacc gacgtgcact | 1440 |
| gtcttttgtg gcaccggcta tataaaggtg gtctgtccgt tctgagccac acgagtcatc | 1500 |
| atgaagatcc catacgtctt gctgttcctt gtggtgagtt gctttcgttt tgatatgct | 1560 |
| ggttcctcag gagtctgtac taatgcttct gtttttattg tataaatgtg agcacttcac | 1620 |
| ggcctacgta accagctggt tacaatcacc gtccacgccg aaaaaatgag gcctgtatct | 1680 |
| aaattgtaac ataattttg cacatttgat tctcatccca cgatttattt tatctttcat | 1740 |
| tcattttac tggtggtagg acgtcttgtg agtccgcacg tgcaccacct cacctatttc | 1800 |
| agccgtgaag cagtaatgcg cttcggtttg aagggtgggg cagccgttgt actttataaa | 1860 |

```
cggagacctt agaactcatg tcccgagatg ggtggcagca tttacgttgc agatgtctat    1920
gggctccggt aaccacttaa cattttttt ttttcttttt tttttttttt tatcacgcta    1980
cgttaattgg tcccgtgata agttcgtaaa gaacttgtgt tacaggtacc agataa       2036
```

<210> SEQ ID NO 18
<211> LENGTH: 1027
<212> TYPE: DNA
<213> ORGANISM: Bombyx mori

<400> SEQUENCE: 18

```
gaattcaaat aacaaagtgg tgcctatccc acttttttg atccagacaa agaaaataag     60
tgttttcggt gagctgaaaa attaatttca ggaaacaaca aaataatga cgcaaaagta    120 caccggagtg aaaataaaca ctaagaaagt aatcgctaaa aattattcat ctcgtgaatt    180
gattgagcgc gataataacg cagtactatt ggagagattc tatgtttaat atattaatga    240
tatgatataa aaagggtgc gtgtacttat gtacgcgcgt aagaagttat actttatttt    300
cattaaattt atttcttttt ttttatttca attttaatca atttgaaaaa aaatcgaata    360
aacaacatcc tcaaacatgc atattggaca tccctttct tgacatcgta taaattcggt    420
aattctcggt acggttcgta aagttcacct gcggctatat tccgactcgc caagttacgt    480
cagtcgtatt gtaatgagcg atttagtggg caacttcatt ctgttaattt tgtgtcacgg    540
tgcgcgcgca tcgtaaaact tcactctcat agattttca taacgcgcct aaagaagtat    600
aacttcaata atttaaattt aaaaaaaaac atgcatagaa taattatatg aattatttaa    660
aatgtcattt accgacattg acataacaga cgacgttaac actacaaaac attttaattc    720
cacattgtta catattcaac agttaaattt gcgttaattc tcgatgcgaa caaatataag    780
aacaatcgga tcaattagat cgctttgttt cgaacaacac ttagtttaac tagaggcgta    840 caccctcaaga aatcatcttc attagaaact aaaccttaaa atcgcaataa taaagcatag    900
tcaattttaa ctgaaatgca aagtcttttg aacgttagat gctgtcagcg ttcgttggta    960
cagttgtttg atatttattt taattgtctt tttatatata aatagtggaa cattaatcac   1020
ggaatcc                                                            1027
```

<210> SEQ ID NO 19
<211> LENGTH: 1892
<212> TYPE: DNA
<213> ORGANISM: Bombyx mori

<400> SEQUENCE: 19

```
gaattcgaaa aagcaaaaac ttaaataaat aaaacattca atttattcta agtggcgca     60 tgaaaggcga ttgcatgcag cagagatgcg aatgttgcga cggatgtgtg gagtaacgag    120
aatggataga atacggaatg aatatgttag aggaagtctg aaagtggcac ctgtgacaga    180
gaagctgaga agtgcgcgct tgggattgta tggacatgtg atgagacgaa atgaaaatga    240
ggttggtaag agaatgttaa ctataaatgt ggaaggatat agaggaagag gtagacctaa    300
gaagaaatgg atggattgcg taaaagacga tatgggtaag aggggagtga gcgaagaaat    360
ggtatatgat agaagagtat ggaaggagaa acatgttcc gaccccaggt tactgggaga    420
agggcagata atgatgattc aatttattct gagcgtaagt ggaatgtttt cgacctgaac    480
gtcatcagct gctaactaca atgcaaatca tactcaagta tgcctgctgg ttaacgttaa    540
tgcgtaagtc agaaatattg gtaaatagga aacctgacaa ggttttacga atgcgattct    600
```

```
ttacattctc atgtatctgt catgaaccat tacgagttcc agcattaccc gttttagag      660 cagttccaaa gaaatcttg aagatgttac atactacata catacataca tattttttac     720
tagtggcctc ttgtgcttta atttgttaat ttgctcagga tacctttttc ggtttcggga     780
actttacctt gaatctcgct tgaagaacaa caatcgcctt tagagactcg aggttagtat     840
gaaattaaaa taataaataa taaaatatta aattgtttaa tgtttattgt tcctccctcg     900
aaaccctcca aatagaatct actggtggta ggagctcttg tgagtcctcg cgggtaggta     960
ccaccaccct gcctatttct gccgtgaagc agtaatgcgt ttcggtttga agagtggggc    1020
ggccgtggta ctgagacctt agaactcata tctgaaggtg ggtggcacat ttacgttgta    1080
gatgtctatg ggctccagta accacttaac atcaggtggg ctgtgagctc ttacacccat    1140
ctacgcaata aaaattaaa aataaatatg tttgaagtcc gtaacataga ttccgtattt    1200
ttacagttgt ttttcacgtt tttcatttct tcaccgacaa tggaaaataa tcacacacaa    1260
atacactgta tagtaacaac gagcagagcc gatttggag tttcgataaa gcgaggctac    1320
caagaatgcg gcagataaga tttacgtaca ttcaagagtc gctgataaca acttttacct    1380
ctcaaattgc ccacagtgcg atcacaagaa acatagacga acggatctgt gcgcaacgag    1440
ccgctacgat atcattatca tacagatttt tatcttttca tctagcttca gttagtgatg    1500
ctttctgatc tcttcataat tataattaaa aagaataaat tatctagtaa tatagttcta    1560
ctacggtaca cgaattttga gattaattaa ccggattttc tgggttatga tttacatcgg    1620
tacagaatct agtgaaagca cgtcgagtga aattctatga aacttcggcg ggagtcgggg    1680
agaggttaca agcgaccgcg aggtgccgct aacttaatca gttatcaagg catcgcctta    1740
tcaaaagatg cgagctgata gcgtgcgcgt taccatatat ggtgacaaaa actgagtcag    1800
cccgcgattg gtggaaaaac aaactggagc cgatactgtg taaattgtga taacggctct    1860
tttatatagt ttatcctcac gagtcggttc tc                                  1892

<210> SEQ ID NO 20
<211> LENGTH: 51
<212> TYPE: DNA
<213> ORGANISM: Mus musculus

<400> SEQUENCE: 20
atggatttac aggtgcagat tatcagcttc ctgctaatca ttgtcacagt c               51

<210> SEQ ID NO 21
<211> LENGTH: 17
<212> TYPE: PRT
<213> ORGANISM: Mus musculus

<400> SEQUENCE: 21

Met Asp Leu Gln Val Gln Ile Ile Ser Phe Leu Leu Ile Ile Val Thr
1               5                   10                  15

Val

<210> SEQ ID NO 22
<211> LENGTH: 336
<212> TYPE: DNA
<213> ORGANISM: Mus musculus

<400> SEQUENCE: 22
attgagctca cccagtctcc atcctcccta gctgtgtcag ttggagagaa ggttactatg      60
acctgcaagt ccagtcagag ccttttatat agtaccaatc aaaagaacta cttggcctgg    120
```

```
taccagcaga aaccagggca gtctcctaaa ctgctgattt actgggcatc cactagggaa    180
tctggggtcc ctgatcgctt cacaggcagt ggatctggga cagatttcac tctcaccatc    240
agcagtgtga aggctgaaga cctgtcagtt tattactgtc agcaatatta tagctatcct    300
cccacgttcg gctcgggcac caagctggaa atcaaa                              336
```

<210> SEQ ID NO 23
<211> LENGTH: 112
<212> TYPE: PRT
<213> ORGANISM: Mus musculus

<400> SEQUENCE: 23

```
Ile Glu Leu Thr Gln Ser Pro Ser Ser Leu Ala Val Ser Val Gly Glu
1               5                   10                  15

Lys Val Thr Met Thr Cys Lys Ser Ser Gln Ser Leu Leu Tyr Ser Thr
            20                  25                  30

Asn Gln Lys Asn Tyr Leu Ala Trp Tyr Gln Gln Lys Pro Gly Gln Ser
        35                  40                  45

Pro Lys Leu Leu Ile Tyr Trp Ala Ser Thr Arg Glu Ser Gly Val Pro
    50                  55                  60

Asp Arg Phe Thr Gly Ser Gly Ser Gly Thr Asp Phe Thr Leu Thr Ile
65                  70                  75                  80

Ser Ser Val Lys Ala Glu Asp Leu Ser Val Tyr Tyr Cys Gln Gln Tyr
                85                  90                  95

Tyr Ser Tyr Pro Pro Thr Phe Gly Ser Gly Thr Lys Leu Glu Ile Lys
            100                 105                 110
```

<210> SEQ ID NO 24
<211> LENGTH: 39
<212> TYPE: DNA
<213> ORGANISM: Mus musculus

<400> SEQUENCE: 24

```
tacacgttcg gagggggggac caagctggaa ataaaacgg                           39
```

<210> SEQ ID NO 25
<211> LENGTH: 13
<212> TYPE: PRT
<213> ORGANISM: Mus musculus

<400> SEQUENCE: 25

```
Tyr Thr Phe Gly Gly Gly Thr Lys Leu Glu Ile Lys Arg
1               5                   10
```

<210> SEQ ID NO 26
<211> LENGTH: 318
<212> TYPE: DNA
<213> ORGANISM: Mus musculus

<400> SEQUENCE: 26

```
gctgatgctg caccaactgt atccatcttc ccaccatcca gtgagcagtt aacatctgga     60
ggtgcctcag tcgtgtgctt cttgaacaac ttctacccca agacatcaa tgtcaagtgg     120 aagattgatg gcagtgaacg acaaaatggc gtcctgaaca gttggactga tcaggacagc    180
aaagacagca cctacagcat gagcagcacc ctcacgttga ccaaggacga gtatgaacga    240
cataacagct atacctgtga ggccactcac aagacatcta cttcacccat tgtcaagagc    300
ttcaacagga atgagtgt                                                  318
```

<210> SEQ ID NO 27
<211> LENGTH: 106
<212> TYPE: PRT
<213> ORGANISM: Mus musculus

<400> SEQUENCE: 27

Ala Asp Ala Ala Pro Thr Val Ser Ile Phe Pro Pro Ser Ser Glu Gln
1               5                   10                  15

Leu Thr Ser Gly Gly Ala Ser Val Val Cys Phe Leu Asn Asn Phe Tyr
            20                  25                  30

Pro Lys Asp Ile Asn Val Lys Trp Lys Ile Asp Gly Ser Glu Arg Gln
        35                  40                  45

Asn Gly Val Leu Asn Ser Trp Thr Asp Gln Asp Ser Lys Asp Ser Thr
    50                  55                  60

Tyr Ser Met Ser Ser Thr Leu Thr Leu Thr Lys Asp Glu Tyr Glu Arg
65                  70                  75                  80

His Asn Ser Tyr Thr Cys Glu Ala Thr His Lys Thr Ser Thr Ser Pro
                85                  90                  95

Ile Val Lys Ser Phe Asn Arg Asn Glu Cys
            100                 105

<210> SEQ ID NO 28
<211> LENGTH: 57
<212> TYPE: DNA
<213> ORGANISM: Mus musculus

<400> SEQUENCE: 28
atgggatgga gctggatctt tctctttctc ctgtcaggaa ctgcaggtgt cctctct      57

<210> SEQ ID NO 29
<211> LENGTH: 19
<212> TYPE: PRT
<213> ORGANISM: Mus musculus

<400> SEQUENCE: 29

Met Gly Trp Ser Trp Ile Phe Leu Phe Leu Leu Ser Gly Thr Ala Gly
1               5                   10                  15

Val Leu Ser

<210> SEQ ID NO 30
<211> LENGTH: 357
<212> TYPE: DNA
<213> ORGANISM: Mus musculus

<400> SEQUENCE: 30
gtccagctgc aggagtcggg acctgacctg gtgaaacctt ctcagtcact ttcactcacc      60
tgcactgtca ctggctactc catcaccagt ggttatagct ggcactggat ccggcagttt     120
ccagaaaaca aactggaatg ctgggctac atacactcca gtggtgccac taactacagc      180
ccatctctca aaagtcgatt ctctatcact cgagacacat ccaagaacca gttcttcctg     240
cagttgaatt ctgtgactac tgaggacaca gccacatatt actgtgcaag ggatggttac     300
tccccctccct atgctatgga ctattggggc caagggacca cggtcaccgt ctcctca       357

<210> SEQ ID NO 31
<211> LENGTH: 119
<212> TYPE: PRT
<213> ORGANISM: Mus musculus

<400> SEQUENCE: 31

Val Gln Leu Gln Glu Ser Gly Pro Asp Leu Val Lys Pro Ser Gln Ser
1               5                   10                  15

Leu Ser Leu Thr Cys Thr Val Thr Gly Tyr Ser Ile Thr Ser Gly Tyr
            20                  25                  30

Ser Trp His Trp Ile Arg Gln Phe Pro Glu Asn Lys Leu Glu Trp Leu
        35                  40                  45

Gly Tyr Ile His Ser Ser Gly Ala Thr Asn Tyr Ser Pro Ser Leu Lys
    50                  55                  60

Ser Arg Phe Ser Ile Thr Arg Asp Thr Ser Lys Asn Gln Phe Phe Leu
65                  70                  75                  80

Gln Leu Asn Ser Val Thr Thr Glu Asp Thr Ala Thr Tyr Tyr Cys Ala
                85                  90                  95

Arg Asp Gly Tyr Ser Pro Pro Tyr Ala Met Asp Tyr Trp Gly Gln Gly
                100                 105                 110

Thr Thr Val Thr Val Ser Ser
            115

<210> SEQ ID NO 32
<211> LENGTH: 291
<212> TYPE: DNA
<213> ORGANISM: Mus musculus

<400> SEQUENCE: 32
gccaaaacga cacccccatc tgtctatcca ctggcccctg gatctgctgc ccaaactaac      60
tccatggtga ccctgggatg cctggtcaag ggctatttcc ctgagccagt gacagtgacc     120
tggaactctg gatccctgtc cagcggtgtg cacaccttcc cagctgtcct ggagtctgac     180
ctctacactc tgagcagctc agtgactgtc ccctccagcc ctcggcccag cgagaccgtc     240
acctgcaacg ttgcccaccc ggccagcagc accaaggtgg acaagaaaat t              291

<210> SEQ ID NO 33
<211> LENGTH: 97
<212> TYPE: PRT
<213> ORGANISM: Mus musculus

<400> SEQUENCE: 33

Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
            20                  25                  30

Phe Pro Glu Pro Val Thr Val Thr Trp Asn Ser Gly Ser Leu Ser Ser
        35                  40                  45

Gly Val His Thr Phe Pro Ala Val Leu Glu Ser Asp Leu Tyr Thr Leu
    50                  55                  60

Ser Ser Ser Val Thr Val Pro Ser Ser Pro Arg Pro Ser Glu Thr Val
65                  70                  75                  80

Thr Cys Asn Val Ala His Pro Ala Ser Ser Thr Lys Val Asp Lys Lys
                85                  90                  95

Ile

<210> SEQ ID NO 34
<211> LENGTH: 39
<212> TYPE: DNA
<213> ORGANISM: Mus musculus

<400> SEQUENCE: 34
gtgcccaggg attgtggttg taagccttgc atatgtaca                             39

<210> SEQ ID NO 35
<211> LENGTH: 13
<212> TYPE: PRT
<213> ORGANISM: Mus musculus

<400> SEQUENCE: 35

Val Pro Arg Asp Cys Gly Cys Lys Pro Cys Ile Cys Thr
1               5                   10

<210> SEQ ID NO 36
<211> LENGTH: 321
<212> TYPE: DNA
<213> ORGANISM: Mus musculus

<400> SEQUENCE: 36

```
gtcccagaag tatcatctgt cttcatcttc cccccaaagc ccaaggatgt gctcaccatt      60
actctgactc ctaaggtcac gtgtgttgtg gtagacatca gcaaggatga tcccgaggtc     120
cagttcagct ggtttgtaga tgatgtggag gtgcacacac tcagacgca accccgggag      180
gagcagttca acagcacttt ccgctcagtc agtgaacttc ccatcatgca ccaggactgg     240
ctcaatggca aggagttcaa atgcagggtc aacagtgcag ctttccctgc ccccatcgag     300
aaaaccatct ccaaaaccaa a                                               321
```

<210> SEQ ID NO 37
<211> LENGTH: 107
<212> TYPE: PRT
<213> ORGANISM: Mus musculus

<400> SEQUENCE: 37

Val Pro Glu Val Ser Ser Val Phe Ile Phe Pro Pro Lys Pro Lys Asp
1               5                   10                  15

Val Leu Thr Ile Thr Leu Thr Pro Lys Val Thr Cys Val Val Val Asp
                20                  25                  30

Ile Ser Lys Asp Asp Pro Glu Val Gln Phe Ser Trp Phe Val Asp Asp
            35                  40                  45

Val Glu Val His Thr Ala Gln Thr Gln Pro Arg Glu Glu Gln Phe Asn
        50                  55                  60

Ser Thr Phe Arg Ser Val Ser Glu Leu Pro Ile Met His Gln Asp Trp
65                  70                  75                  80

Leu Asn Gly Lys Glu Phe Lys Cys Arg Val Asn Ser Ala Ala Phe Pro
                85                  90                  95

Ala Pro Ile Glu Lys Thr Ile Ser Lys Thr Lys
            100                 105

<210> SEQ ID NO 38
<211> LENGTH: 321
<212> TYPE: DNA
<213> ORGANISM: Mus musculus

<400> SEQUENCE: 38

```
ggcagaccga aggctccaca ggtgtacacc attccacctc ccaaggagca gatggccaag      60
gataaagtca gtctgacctg catgataaca gacttcttcc ctgaagacat tactgtggag     120
tggcagtgga atgggcagcc agcggagaac tacaagaaca ctcagcccat catgaacacg     180
aatggctctt acttcgtcta cagcaagctc aatgtgcaga gagcaactg ggaggcagga      240
aatactttca cctgctctgt gttacatgag ggcctgcaca ccaccatac tgagaagagc      300
```
ctctcccact ctcctggtaa a                                              321

<210> SEQ ID NO 39
<211> LENGTH: 107
<212> TYPE: PRT
<213> ORGANISM: Mus musculus

<400> SEQUENCE: 39

Gly Arg Pro Lys Ala Pro Gln Val Tyr Thr Ile Pro Pro Lys Glu
1               5                   10                  15

Gln Met Ala Lys Asp Lys Val Ser Leu Thr Cys Met Ile Thr Asp Phe
            20                  25                  30

Phe Pro Glu Asp Ile Thr Val Glu Trp Gln Trp Asn Gly Gln Pro Ala
        35                  40                  45

Glu Asn Tyr Lys Asn Thr Gln Pro Ile Met Asn Thr Asn Gly Ser Tyr
    50                  55                  60

Phe Val Tyr Ser Lys Leu Asn Val Gln Lys Ser Asn Trp Glu Ala Gly
65                  70                  75                  80

Asn Thr Phe Thr Cys Ser Val Leu His Glu Gly Leu His Asn His His
                85                  90                  95

Thr Glu Lys Ser Leu Ser His Ser Pro Gly Lys
            100                 105

<210> SEQ ID NO 40
<211> LENGTH: 21
<212> TYPE: DNA
<213> ORGANISM: Artificial
<220> FEATURE:
<223> OTHER INFORMATION: An artificially synthesized primer sequence

<400> SEQUENCE: 40
gcagattatc agcttcctgc t                                              21

<210> SEQ ID NO 41
<211> LENGTH: 21
<212> TYPE: DNA
<213> ORGANISM: Artificial
<220> FEATURE:
<223> OTHER INFORMATION: An artificially synthesized primer sequence

<400> SEQUENCE: 41
gacaggtctt cagccttcac a                                              21

<210> SEQ ID NO 42
<211> LENGTH: 20
<212> TYPE: DNA
<213> ORGANISM: Artificial
<220> FEATURE:
<223> OTHER INFORMATION: An artificially synthesized primer sequence

<400> SEQUENCE: 42
ggaactgcag gtgtcctctc                                                20

<210> SEQ ID NO 43
<211> LENGTH: 20
<212> TYPE: DNA
<213> ORGANISM: Artificial
<220> FEATURE:
<223> OTHER INFORMATION: An artificially synthesized primer sequence

<400> SEQUENCE: 43
aggggagtaa ccatcccttg                                                20

<210> SEQ ID NO 44
<211> LENGTH: 21
<212> TYPE: DNA
<213> ORGANISM: Artificial
<220> FEATURE:
<223> OTHER INFORMATION: An artificially synthesized primer sequence

<400> SEQUENCE: 44
ctcgtccttc agtgatagca g                                         21

<210> SEQ ID NO 45
<211> LENGTH: 22
<212> TYPE: DNA
<213> ORGANISM: Artificial
<220> FEATURE:
<223> OTHER INFORMATION: An artificially synthesized primer sequence

<400> SEQUENCE: 45
cgcttaacat gatggagcat cg                                        22

<210> SEQ ID NO 46
<211> LENGTH: 19
<212> TYPE: DNA
<213> ORGANISM: Artificial
<220> FEATURE:
<223> OTHER INFORMATION: An artificially synthesized primer sequence

<400> SEQUENCE: 46
tacaatgagc tgcgtgtcg                                            19

<210> SEQ ID NO 47
<211> LENGTH: 19
<212> TYPE: DNA
<213> ORGANISM: Artificial
<220> FEATURE:
<223> OTHER INFORMATION: An artificially synthesized primer sequence

<400> SEQUENCE: 47
cgggcgtgtt gaatgtttc                                            19

<210> SEQ ID NO 48
<211> LENGTH: 744
<212> TYPE: DNA
<213> ORGANISM: Mus musculus

<400> SEQUENCE: 48
atggatttac aggtgcagat tatcagcttc ctgctaatca ttgtcacagt cattgagctc      60
acccagtctc catcctccct agctgtgtca gttggagaga aggttactat gacctgcaag     120
tccagtcaga ccttttata tagtaccaat caaaagaact acttggcctg gtaccagcag     180
aaaccagggc agtctcctaa actgctgatt tactgggcat ccactaggga atctggggtc     240
cctgatcgct tcacaggcag tggatctggg acagatttca ctctcaccat cagcagtgtg     300
aaggctgaag acctgtcagt ttattactgt cagcaatatt atagctatcc tcccacgttc     360
ggctcgggca ccaagctgga aatcaaatgg acgttcggtg gaggcaccaa gctggaaatc     420
aaacgggctg atgctgcacc aactgtatcc atcttccac catccagtga gcagttaaca     480
tctggaggtg cctcagtcgt gtgcttcttg aacaacttct accccaaaga catcaatgtc     540
aagtggaaga ttgatggcag tgaacgacaa aatggcgtcc tgaacagttg gactgatcag     600
gacagcaaag acagcaccta cagcatgagc agcaccctca cgttgaccaa ggacgagtat     660
gaacgacata acagctatac ctgtgaggcc actcacaaga catctacttc acccattgtc     720

```
aagagcttca acaggaatga gtgt                                            744
```

<210> SEQ ID NO 49
<211> LENGTH: 248
<212> TYPE: PRT
<213> ORGANISM: Mus musculus

<400> SEQUENCE: 49

```
Met Asp Leu Gln Val Gln Ile Ile Ser Phe Leu Leu Ile Ile Val Thr
1               5                   10                  15

Val Ile Glu Leu Thr Gln Ser Pro Ser Ser Leu Ala Val Ser Val Gly
            20                  25                  30

Glu Lys Val Thr Met Thr Cys Lys Ser Ser Gln Ser Leu Leu Tyr Ser
        35                  40                  45

Thr Asn Gln Lys Asn Tyr Leu Ala Trp Tyr Gln Lys Pro Gly Gln
    50                  55                  60

Ser Pro Lys Leu Leu Ile Tyr Trp Ala Ser Thr Arg Glu Ser Gly Val
65                  70                  75                  80

Pro Asp Arg Phe Thr Gly Ser Gly Ser Gly Thr Asp Phe Thr Leu Thr
                85                  90                  95

Ile Ser Ser Val Lys Ala Glu Asp Leu Ser Val Tyr Tyr Cys Gln Gln
            100                 105                 110

Tyr Tyr Ser Tyr Pro Pro Thr Phe Gly Ser Gly Thr Lys Leu Glu Ile
        115                 120                 125

Lys Trp Thr Phe Gly Gly Gly Thr Lys Leu Glu Ile Lys Arg Ala Asp
    130                 135                 140

Ala Ala Pro Thr Val Ser Ile Phe Pro Pro Ser Ser Glu Gln Leu Thr
145                 150                 155                 160

Ser Gly Gly Ala Ser Val Val Cys Phe Leu Asn Asn Phe Tyr Pro Lys
                165                 170                 175

Asp Ile Asn Val Lys Trp Lys Ile Asp Gly Ser Glu Arg Gln Asn Gly
            180                 185                 190

Val Leu Asn Ser Trp Thr Asp Gln Asp Ser Lys Asp Ser Thr Tyr Ser
        195                 200                 205

Met Ser Ser Thr Leu Thr Leu Thr Lys Asp Glu Tyr Glu Arg His Asn
    210                 215                 220

Ser Tyr Thr Cys Glu Ala Thr His Lys Thr Ser Thr Ser Pro Ile Val
225                 230                 235                 240

Lys Ser Phe Asn Arg Asn Glu Cys
                245
```

<210> SEQ ID NO 50
<211> LENGTH: 1386
<212> TYPE: DNA
<213> ORGANISM: Mus musculus

<400> SEQUENCE: 50

```
atgggatgga gctggatctt tctctttctc ctgtcaggaa ctgcaggtgt cctctctgtc     60
cagctgcagg agtcgggacc tgacctggtg aaaccttctc agtcactttc actcacctgc    120
actgtcactg gctactccat caccagtggt tatagctggc actggatccg gcagtttcca    180
gaaaacaaac tggaatggct gggctacata cactccagtg gtgccactaa ctacagccca    240
tctctcaaaa gtcgattctc tatcactcga gacacatcca agaaccagtt cttcctgcag    300
ttgaattctg tgactactga ggacacagcc acatattact gtgcaaggga tggttactcc    360
```

```
cctccctatg ctatggacta ttggggccaa gggaccacgg tcaccgtctc ctcagccaaa    420
acgacacccc catctgtcta tccactggcc cctggatctg ctgcccaaac taactccatg    480
gtgaccctgg gatgcctggt caagggctat ttccctgagc cagtgacagt gacctggaac    540
tctggatccc tgtccagcgg tgtgcacacc ttcccagctg tcctggagtc tgacctctac    600
actctgagca gctcagtgac tgtcccctcc agccctcggc cagcgagac cgtcacctgc    660 aacgttgccc acccggccag cagcaccaag gtggacaaga aaattgtgcc cagggattgt    720
ggttgtaagc cttgcatatg tacagtccca gaagtatcat ctgtcttcat cttccccca    780 aagcccaagg atgtgctcac cattactctg actcctaagg tcacgtgtgt tgtggtagac    840
atcagcaagg atgatcccga ggtccagttc agctggtttg tagatgatgt ggaggtgcac    900
acagctcaga cgcaaccccg ggaggagcag ttcaacagca ctttccgctc agtcagtgaa    960
cttcccatca tgcaccagga ctggctcaat ggcaaggagt tcaaatgcag ggtcaacagt   1020
gcagctttcc ctgcccccat cgagaaaacc atctccaaaa ccaaaggcag accgaaggct   1080
ccacaggtgt acaccattcc acctcccaag gagcagatgg ccaaggataa agtcagtctg   1140
acctgcatga taacagactt cttccctgaa gacattactg tggagtggca gtggaatggg   1200
cagccagcgg agaactacaa gaacactcag cccatcatga cacgaatgg ctcttacttc   1260 gtctacagca agctcaatgt gcagaagagc aactgggagg caggaaatac tttcacctgc   1320
tctgtgttac atgagggcct gcacaaccac catactgaga gagcctctc ccactctcct   1380 ggtaaa                                                              1386
```

<210> SEQ ID NO 51
<211> LENGTH: 462
<212> TYPE: PRT
<213> ORGANISM: Mus musculus

<400> SEQUENCE: 51

```
Met Gly Trp Ser Trp Ile Phe Leu Phe Leu Leu Ser Gly Thr Ala Gly
  1               5                  10                  15

Val Leu Ser Val Gln Leu Gln Glu Ser Gly Pro Asp Leu Val Lys Pro
             20                  25                  30

Ser Gln Ser Leu Ser Leu Thr Cys Thr Val Thr Gly Tyr Ser Ile Thr
         35                  40                  45

Ser Gly Tyr Ser Trp His Trp Ile Arg Gln Phe Pro Glu Asn Lys Leu
     50                  55                  60

Glu Trp Leu Gly Tyr Ile His Ser Ser Gly Ala Thr Asn Tyr Ser Pro
 65                  70                  75                  80

Ser Leu Lys Ser Arg Phe Ser Ile Thr Arg Asp Thr Ser Lys Asn Gln
                 85                  90                  95

Phe Phe Leu Gln Leu Asn Ser Val Thr Thr Glu Asp Thr Ala Thr Tyr
            100                 105                 110

Tyr Cys Ala Arg Asp Gly Tyr Ser Pro Pro Tyr Ala Met Asp Tyr Trp
        115                 120                 125

Gly Gln Gly Thr Thr Val Thr Val Ser Ser Ala Lys Thr Thr Pro Pro
    130                 135                 140

Ser Val Tyr Pro Leu Ala Pro Gly Ser Ala Ala Gln Thr Asn Ser Met
145                 150                 155                 160

Val Thr Leu Gly Cys Leu Val Lys Gly Tyr Phe Pro Glu Pro Val Thr
                165                 170                 175

Val Thr Trp Asn Ser Gly Ser Leu Ser Ser Gly Val His Thr Phe Pro
            180                 185                 190
```

-continued

```
Ala Val Leu Glu Ser Asp Leu Tyr Thr Leu Ser Ser Ser Val Thr Val
            195                 200                 205

Pro Ser Ser Pro Arg Pro Ser Glu Thr Val Thr Cys Asn Val Ala His
            210                 215                 220

Pro Ala Ser Ser Thr Lys Val Asp Lys Lys Ile Val Pro Arg Asp Cys
225                 230                 235                 240

Gly Cys Lys Pro Cys Ile Cys Thr Val Pro Glu Val Ser Ser Val Phe
                245                 250                 255

Ile Phe Pro Pro Lys Pro Lys Asp Val Leu Thr Ile Thr Leu Thr Pro
            260                 265                 270

Lys Val Thr Cys Val Val Val Asp Ile Ser Lys Asp Asp Pro Glu Val
            275                 280                 285

Gln Phe Ser Trp Phe Val Asp Asp Val Glu Val His Thr Ala Gln Thr
            290                 295                 300

Gln Pro Arg Glu Glu Gln Phe Asn Ser Thr Phe Arg Ser Val Ser Glu
305                 310                 315                 320

Leu Pro Ile Met His Gln Asp Trp Leu Asn Gly Lys Glu Phe Lys Cys
                325                 330                 335

Arg Val Asn Ser Ala Ala Phe Pro Ala Pro Ile Glu Lys Thr Ile Ser
            340                 345                 350

Lys Thr Lys Gly Arg Pro Lys Ala Pro Gln Val Tyr Thr Ile Pro Pro
            355                 360                 365

Pro Lys Glu Gln Met Ala Lys Asp Lys Val Ser Leu Thr Cys Met Ile
    370                 375                 380

Thr Asp Phe Phe Pro Glu Asp Ile Thr Val Glu Trp Gln Trp Asn Gly
385                 390                 395                 400

Gln Pro Ala Glu Asn Tyr Lys Asn Thr Gln Pro Ile Met Asn Thr Asn
                405                 410                 415

Gly Ser Tyr Phe Val Tyr Ser Lys Leu Asn Val Gln Lys Ser Asn Trp
                420                 425                 430

Glu Ala Gly Asn Thr Phe Thr Cys Ser Val Leu His Glu Gly Leu His
            435                 440                 445

Asn His His Thr Glu Lys Ser Leu Ser His Ser Pro Gly Lys
    450                 455                 460
```